(12) United States Patent
Henderson et al.

(10) Patent No.: US 8,478,604 B2
(45) Date of Patent: Jul. 2, 2013

(54) CLOSED LOOP MEDICATION USE SYSTEM AND METHOD

(75) Inventors: Dwight Henderson, Montgomery, AL (US); Richard Lunak, Pittsburgh, PA (US); Eugene Markiewicz, Alpharetta, GA (US); Caren C Tobin, Allison Park, PA (US)

(73) Assignees: McKesson Technologies Inc., Alpharetta, GA (US); McKesson Automation Inc., Cranberry, PA (US)

( * ) Notice: Subject to any disclaimer, the term of this patent is extended or adjusted under 35 U.S.C. 154(b) by 2189 days.

(21) Appl. No.: 10/465,197

(22) Filed: Jun. 19, 2003

(65) Prior Publication Data

US 2003/0236683 A1 Dec. 25, 2003

Related U.S. Application Data

(60) Provisional application No. 60/390,833, filed on Jun. 21, 2002.

(51) Int. Cl.
   *G06Q 40/00* (2012.01)
(52) U.S. Cl.
   USPC .................................................. 705/2; 705/3
(58) Field of Classification Search
   USPC ........................................................ 705/2, 3
   See application file for complete search history.

(56) References Cited

U.S. PATENT DOCUMENTS

| | | | |
|---|---|---|---|
| 4,766,542 A | 8/1988 | Pilarczyk | 364/413 |
| 4,814,759 A | 3/1989 | Gombrich et al. | 340/771 |
| 4,818,850 A | 4/1989 | Gombrich et al. | 235/494 |
| 4,835,372 A | 5/1989 | Gombrich et al. | 235/375 |
| 4,847,764 A | 7/1989 | Halvorson | 364/413.02 |
| 4,850,009 A | 7/1989 | Zook et al. | 379/96 |
| 4,857,716 A | 8/1989 | Gombrich et al. | 235/462 |
| 4,916,441 A | 4/1990 | Gombrich | 340/712 |
| 5,179,569 A | 1/1993 | Sawyer | 375/1 |
| 5,299,121 A | 3/1994 | Brill et al. | 364/413.01 |
| 5,319,543 A | 6/1994 | Wilhelm | 364/401 |
| 5,347,453 A | 9/1994 | Maestre | 364/413 |
| 5,408,443 A * | 4/1995 | Weinberger | 368/10 |
| 5,537,313 A | 7/1996 | Pirelli | 364/403 |
| 5,611,051 A | 3/1997 | Pirelli | 395/210 |

(Continued)

OTHER PUBLICATIONS

International Search Report, dated Feb. 6, 2004, from PCT/US03/19274, filed Jun. 19, 2003.

(Continued)

*Primary Examiner* — Valerie Lubin
*Assistant Examiner* — Reginald R Reyes
(74) *Attorney, Agent, or Firm* — Alston & Bird LLP

(57) ABSTRACT

A closed loop medication use system and method includes selecting a medication to prescribe to a patient based on patient information, such as laboratory results, radiology results, and patient allergies, healthcare industry practices, patient-care site specific guidelines, and medication information. The selected medication is prescribed on an unverified prescription order that is then transcribed. Transcribing includes performing multiple crosschecks of the prescription order to real-time patient information, healthcare industry practices, and medication information to generate a verified prescription order. After transcribing, the appropriate dispensing method is determined for the prescription order and dispensed. The dispensed medication is administered after confirmation by the administering clinician of the right patient, right medication, right dosage, right route, and right time. The whole process of medication use described above is monitored continuously in real-time. The monitored information is communicated to the prescribing, transcribing, dispensing and administering parts of the system.

73 Claims, 43 Drawing Sheets

U.S. PATENT DOCUMENTS

| | | | | |
|---|---|---|---|---|
| 5,640,301 A | 6/1997 | Roecker et al. | ............... | 361/686 |
| 5,666,492 A | 9/1997 | Rhodes et al. | .................... | 705/3 |
| 5,713,485 A | 2/1998 | Liff et al. | .......................... | 221/2 |
| 5,737,539 A | 4/1998 | Edelson et al. | ............... | 395/203 |
| 5,752,235 A | 5/1998 | Kehr et al. | ......................... | 705/3 |
| 5,758,095 A * | 5/1998 | Albaum et al. | ................... | 705/2 |
| 5,758,096 A | 5/1998 | Barsky et al. | ................. | 395/203 |
| 5,774,865 A | 6/1998 | Glynn | ............................ | 705/2 |
| 5,832,449 A | 11/1998 | Cunningham | .................... | 705/3 |
| 5,845,255 A | 12/1998 | Mayaud | ............................ | 705/3 |
| 5,845,264 A | 12/1998 | Nellhaus | ........................ | 705/28 |
| 5,867,821 A | 2/1999 | Ballantyne et al. | ............... | 705/2 |
| 5,883,370 A | 3/1999 | Walker et al. | ..................... | 235/375 |
| 5,884,273 A | 3/1999 | Sattizahn et al. | ................... | 705/3 |
| 5,907,493 A | 5/1999 | Boyer et al. | ............. | 364/479.01 |
| 5,950,630 A | 9/1999 | Portwood et al. | ............. | 128/897 |
| 5,970,462 A | 10/1999 | Reichert | ........................... | 705/2 |
| 5,971,594 A | 10/1999 | Sahai et al. | ............. | 364/479.12 |
| 5,991,731 A | 11/1999 | Colon et al. | ...................... | 705/3 |
| 5,993,046 A | 11/1999 | McGrady et al. | ........ | 364/479.01 |
| 5,995,938 A | 11/1999 | Whaley | .............................. | 705/3 |
| 5,996,889 A | 12/1999 | Fuchs et al. | .................... | 235/375 |
| 6,000,828 A | 12/1999 | Leet | ................................ | 364/401 |
| 6,003,006 A | 12/1999 | Colella et al. | .................... | 705/2 |
| 6,014,631 A | 1/2000 | Teagarden et al. | ............... | 705/3 |
| 6,021,392 A | 2/2000 | Lester et al. | ..................... | 705/2 |
| 6,026,363 A | 2/2000 | Shepard | ............................ | 705/3 |
| 6,032,155 A | 2/2000 | De la Huerga | ................ | 707/104 |
| 6,055,507 A | 4/2000 | Cunningham | .................... | 705/3 |
| 6,067,524 A | 5/2000 | Byerly et al. | ..................... | 705/3 |
| 6,068,156 A | 5/2000 | Liff et al. | .......................... | 221/7 |
| 6,112,182 A | 8/2000 | Akers et al. | ...................... | 705/2 |
| 6,112,502 A | 9/2000 | Frederick et al. | ............... | 53/411 |
| 6,161,095 A | 12/2000 | Brown | .............................. | 705/2 |
| 6,175,779 B1 | 1/2001 | Barrett | .......................... | 700/242 |
| 6,206,829 B1 | 3/2001 | Iliff | ............................... | 600/300 |
| 6,219,587 B1 | 4/2001 | Ahlin et al. | ................... | 700/233 |
| 6,240,394 B1 | 5/2001 | Uecker et al. | ....................... | 705/3 |
| 6,289,656 B1 | 9/2001 | Wangu et al. | .................... | 53/507 |
| 6,294,999 B1 | 9/2001 | Yarin et al. | ................. | 340/573.1 |
| 6,311,163 B1 | 10/2001 | Sheehan et al. | .................... | 705/2 |
| 6,317,719 B1 | 11/2001 | Schrier et al. | ...................... | 705/2 |
| 6,330,491 B1 | 12/2001 | Lion | ................................ | 700/237 |
| 6,332,100 B1 | 12/2001 | Sahai et al. | .................... | 700/242 |
| 6,497,342 B2 | 12/2002 | Zhang et al. | .................. | 221/265 |
| 6,671,579 B2 | 12/2003 | Spano, Jr. et al. | | |
| 7,427,002 B2 * | 9/2008 | Liff et al. | .......................... | 221/13 |
| 2001/0001144 A1 | 5/2001 | Kapp | ................................ | 705/3 |
| 2001/0009398 A1 | 7/2001 | Sekura et al. | ................. | 340/573.1 |
| 2001/0025246 A1 | 9/2001 | Haines et al. | ...................... | 705/3 |
| 2001/0034613 A1 | 10/2001 | Rubsamen | ........................ | 705/2 |
| 2001/0037060 A1 | 11/2001 | Thompson et al. | ........... | 600/365 |
| 2001/0037217 A1 | 11/2001 | Abensour et al. | ................... | 705/2 |
| 2001/0037218 A1 | 11/2001 | Kaker et al. | ....................... | 705/2 |
| 2001/0044730 A1 | 11/2001 | D'Silva | ............................. | 705/3 |
| 2001/0044731 A1 | 11/2001 | Coffman et al. | ................... | 705/3 |
| 2001/0047281 A1 | 11/2001 | Keresman, III et al. | .......... | 705/2 |
| 2001/0049608 A1 | 12/2001 | Hochman | ........................ | 705/3 |
| 2001/0056358 A1 | 12/2001 | Dulong et al. | ..................... | 705/2 |
| 2002/0002472 A1 | 1/2002 | Abraham-Fuchs | ............... | 705/3 |
| 2002/0002473 A1 | 1/2002 | Schrier et al. | ...................... | 705/3 |
| 2002/0010595 A1 | 1/2002 | Kapp | ................................ | 705/2 |
| 2003/0149599 A1 * | 8/2003 | Goodall et al. | ..................... | 705/2 |
| 2004/0078231 A1 * | 4/2004 | Wilkes et al. | ...................... | 705/2 |
| 2004/0158507 A1 | 8/2004 | Meek, Jr. et al. | | |
| 2006/0149587 A1 * | 7/2006 | Hill et al. | .......................... | 705/2 |

OTHER PUBLICATIONS

Written Opinion for International Application No. PCT/US03/19274 mailed Oct. 4, 2004.
Notification of Transmittal of International Preliminary Examination Report for International Application No. PCT/US03/19274 mailed Feb. 3, 2005.

\* cited by examiner

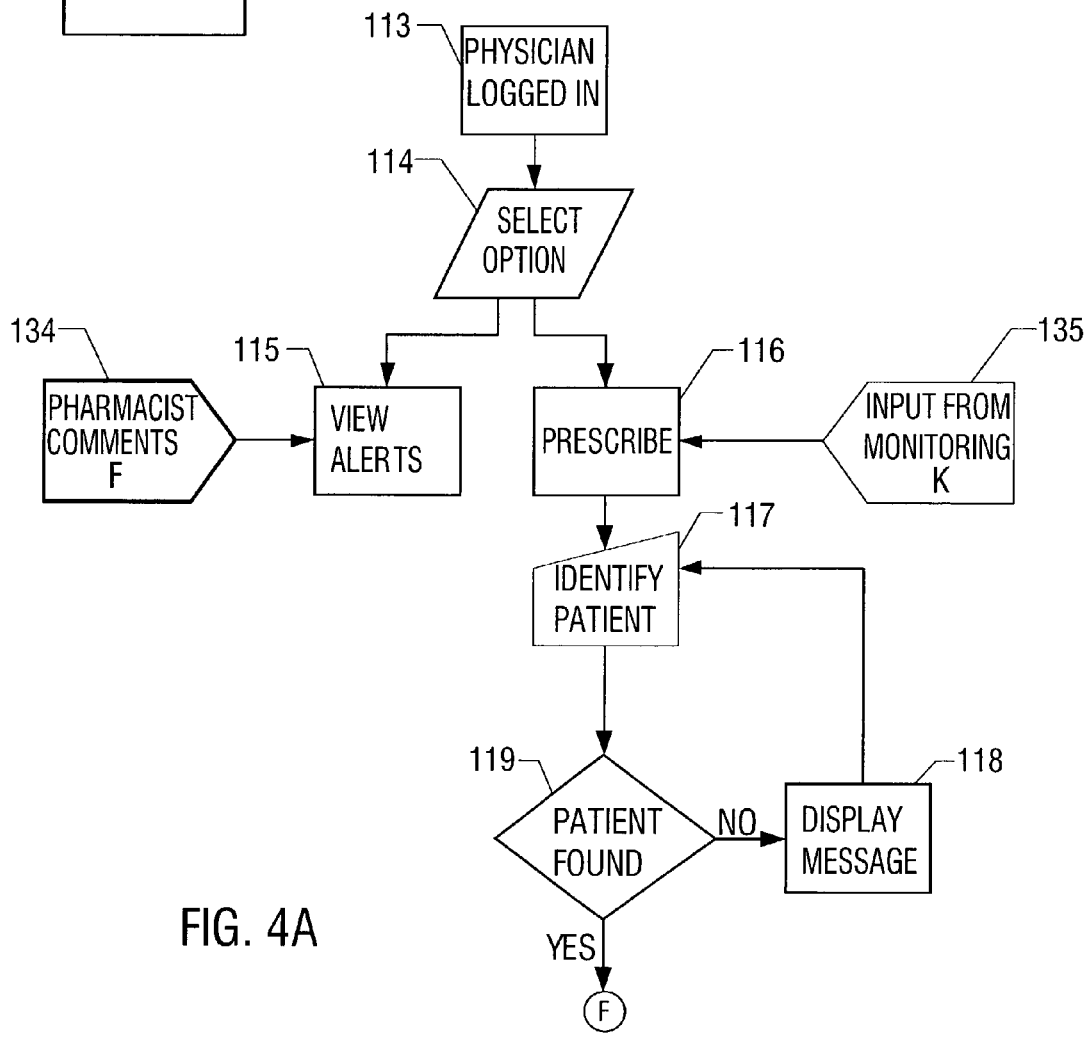

ADC VAAN DISML display

Admission
- admit as inpatient 1 north
- weight: 70.000kg/154lb; height: 180cm/71.0in; bsa: 1.89m2;

Diagnosis
- pneumonia, organism unspecified (486)

Condition
- fair

Vital signs
- vital signs q8h

Activity/limitations

Allergies
- allergy: sulfa-drug class

Nursing instructions
- intake and output qualifier:record

Diet

Medications
=Scheduled medications
- aspirin baby: 81 mg po qam 10

IV fluids

TPN orders

Respiratory therapy
- o2 per nasal cannula 4 lpm
- pulse oximeter, spot check x72h 1. pneumonia pathway orders (Peds) »
2. Pneumonia Pathway Orders - Phase 1(MICU) »
3. Pneumonia Pathway Orders - Phase 2 (Floor) »
4. pneumonia admission orders(Powers) »
5. pneumococcal 7-valent conjugate vaccine (Prevnar)
6. pneumonectomy pathway postoperative orders (adult CT surgery) »
7. legionella pneumo 1-14 (reference lab)
8. pneumococcal ab titer (reference lab)
9. pneumococcal vaccine injection:
10. pcp prophylaxis »
11. peds hem/onc antimicrobial orders (Janco) »
12. pneumocystis &/or fungal stain (lab)
13. Thoracic Surgery post op: SICU pathway orders (CT) »
14. Cystic fibrosis w/ Pneumonia Pathway orders (adult) »
15. cystic fibrosis w/ pneumonia pathway orders (Peds) »
16. chlamydia pneumoniae abs (reference lab)
17. mycoplasma pneumoniae abs (reference lab)

Select an item from the list or enter another order
or press END to return to the previous list antbio

— 610

Guidelines for Weight-Based Dose Adjustments of IV heparin for confirmed DVT/PE Patient Weight = 77 kgs, Current Heparin Drip = 1390 U/Hr. Recommendations based on these values (indicated below in red) require a PTT which was obtained at least 4-6 hours after the last change in the heparin drip.

| PTT (seconds) | Dose Change (U/kg/hr) | Additional Action | Next PTT (hours) | Click To Use |
|---|---|---|---|---|
| <50 | +4 (1390 + 310 = 1700 U/Hr) | Rebolus with 80 U/kg (80 x 77 kg = 6200 Units) | 6 | A |
| 50-64 | +2 (1390 + 150 = 1540 U/Hr) | Rebolus with 40 U/kg (40 x 77 kg = 3100 Units) | 6 | B |
| 65-110 | 0 | None | 6 | C |
| 111-160 | -2 (1390 - 150 = 1240 U/Hr) | None | 6 | |
| >160 | -3 (1390 - 230 = 1160 U/Hr) | Stop infusion one hour | 6 | D |

Four orders you may wish to consider (check to order)

☑ stop heparin for 1 hour

☑ change heparin infusion to (U/hr) [1160]

☐ Rebolus heparin IV (U) [ ]

☐ continue heparin infusion without change

If any of the above recommendations are inappropriate, please explain [ ]

| Current Date and Time: 04/18/2001 09:16 AM | | |
|---|---|---|
| Anticoag Meds | Dose | Date |
| Heparin drip | 1390 U/hr | 04/18/2001 09:10 AM |
| Heparin bolus | 6200 U | 04/18/2001 09:10 AM |
| Warfarin | 2.5 mg QHS | 04/18/2001 10:00 PM |
| Labs | Value | Date |
| PTT | None available | |
| INR | None available | |
| Platelet Count | None available | |
| PCV | None available | |

Nosocomial sepsis syndrome

Severe beta-lactam allergy? No
Staph is major concern? Yes
High renal risk? Yes

| Regimen | Daily cost | |
|---|---|---|
| Ceftazidime 1000mg q8h IV<br>Levofloxacin 500mg q24h IV<br>Vancomycin 1000mg q12h IV<br>Vancomycin trough level before fourth dose<br>Vancomycin peak level after fourth dose | $ 86.74 | order it |
| Piperacillin 4000mg q6h IV<br>Levofloxacin 500mg q24h IV<br>Vancomycin 1000mg q12h IV<br>Vancomycin trough level before fourth dose<br>Vancomycin peak level after fourth dose | $ 108.26 | order it |
| Ceftazidime 1000mg q8h IV<br>Ciprofloxacin 400mg q12h IV<br>Vancomycin 1000mg q12h IV<br>Vancomycin trough level before fourth dose<br>Vancomycin peak level after fourth dose | $ 114.26 | order it |
| Imipenem 500mg q6h IV<br>Vancomycin 1000mg q12h IV<br>Vancomycin trough level before fourth dose<br>Vancomycin peak level after fourth dose | $ 124.14 | order it |
| Piperacillin 4000mg q6h IV<br>Ciprofloxacin 400mg q12h IV<br>Vancomycin 1000mg q12h IV<br>Vancomycin trough level before fourth dose<br>Vancomycin peak level after fourth dose | $ 135.78 | order it |

IV heparin for Confirmed PE in Adults

Guidelines for the treatment of Confirmed PE are listed below with calculated values in RED based on the patient's weight (60 kg).

- Bolus with heparin 80 U/kg I.V. [CONTRAINDICATIONS]
- Begin maintenance infusuion of heparin at 18 U/kg/hr [CONTRAINDICATIONS] [LMW HEPARIN]
- check PTT at 6 hour intervals to keep PTT in range of 65 to 110 seconds
- check platelet count daily [INFO ON HEPARIN INDUCED THROMBOCYTOPENIA]
- start warfarin therapy on day 1 at 5 mg and adjust to give INR of 2-3 [CONTRAINDICATIONS]
- stop heparin therapy after at least 4-5 days of combined therapy when INR is > 2.0 for 2 consecutive days
- continue warfarin treatment for at least 3 months at INR of 2.0 - 3.0 [DURATION]

Orders you may wish to consider (check to order) - Order only necessary items (duplicate order checking not done on this page).

- ☑ Bolus/rebolus with I.V. heparin (U) [4800]   (80 x 60 kg = 4800 IU)
- ☑ Begin continuous infusion of I.V. heparin (U/hr) [1080]   (18 x 60 kg = 1080 IU/hr)
- ☑ Check PTT q6 (starting 6 hours after bolus)
- ☑ Check platelet count qAM
- ☑ Begin warfarin p.o at (mg/day) [5] on (mm/dd/yy) [08/11/00]
- ☑ check PT/INR qAM I am not doing some/all suggestions above because [                    ]

[Order the selected items] [Clear selections] [Cancel]

Current Date and Time: 08/11/2000 03:21 PM

| Anticoag Meds | Dose | Date |
|---|---|---|
| No Anticoagulant Meds | | |

| Labs | Value | Date |
|---|---|---|
| PTT | None available | |
| INR | None available | |
| Platelet Count | None available | |
| PCV | None available | |

[Print]

FIG. 10

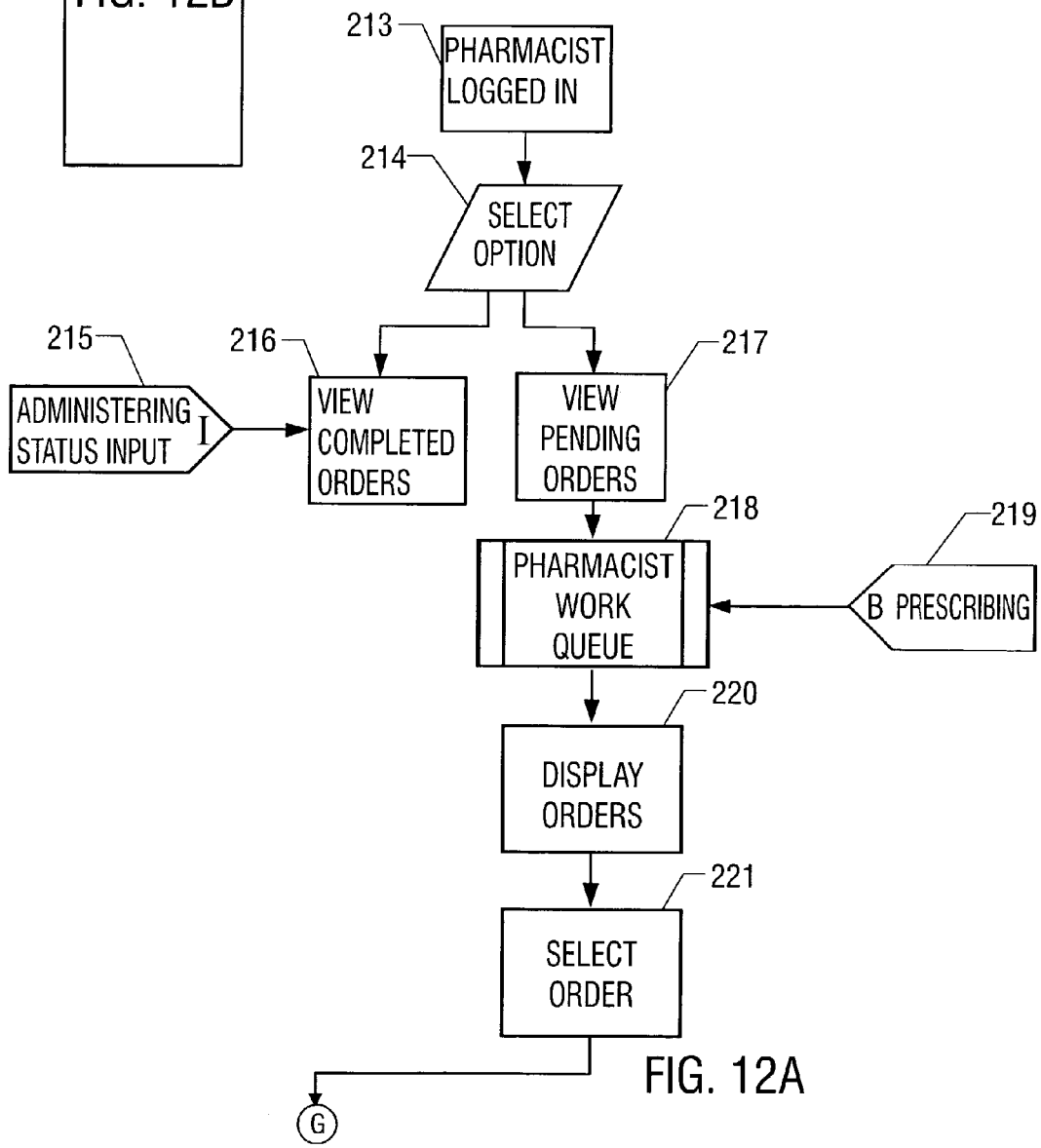

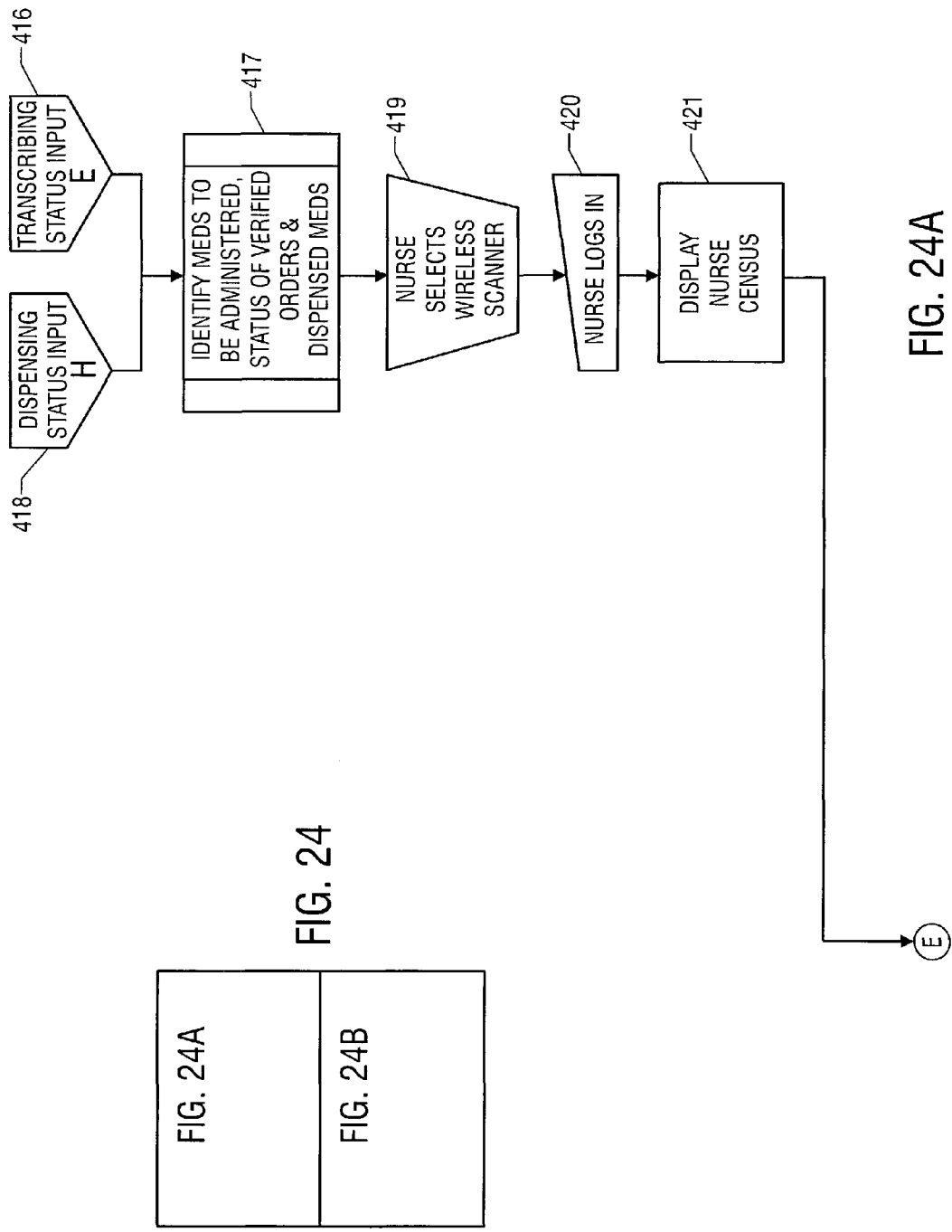

CLOSED LOOP MEDICATION USE SYSTEM AND METHOD

CROSS-REFERENCE TO RELATED APPLICATIONS

This application claims the benefit under 35 U.S.C. §119 (e) of U.S. provisional application Ser. No. 60/390,833 entitled "CLOSED LOOP MEDICATION USE SYSTEM AND METHOD" filed on Jun. 21, 2002, by Dwight Henderson et al., which application is incorporated in its entirety by reference herein.

BACKGROUND OF THE INVENTION

1. Field of the Invention

The present invention generally relates to a system and method for use of medication in a patient-care environment. More particularly, the invention relates to a closed loop medication use system and method containing computer hardware and software connected to facilitate communication and perform tasks to assist medical professionals in patient care.

2. Background of the Invention

In a medical care environment, care providers such as physicians order medications for patients on a routine basis. This important task in the practice of medicine requires the physician to draw upon a huge base of information in their choice of medications for the patient. The physician's choice of medications must take into account the patient's condition and medical history, knowledge of medications and pharmacology, and clinical and therapeutic data.

In a paper-based care environment, physicians order medications for patients by writing an order in a chart or by writing a drug prescription on a paper prescription blank. The physician typically relies on personal knowledge supplemented by available reference sources together with an in depth understanding of the patient's medical condition when deciding what medication to order for the patient. In addition, the physician may have access to a stand-alone clinical information technology system containing the patient's data and lab results. However, much of this information may be outdated and the physician may not have ready access to the most current patient data. Key information may get lost in the shuffle of papers or not be reported in time.

Pharmacists and nurses who dispense and administer the physician's medication orders in a paper-based care environment are also forced to fill the prescription or care for patients based on a static view of information that may be several hours or even days old. Old information may lead to errors in the treatment of the patient and violate the "five rights" (right patient, right medication, right dosage, right route, and right time of administration) of the patient. In addition, because of handwriting issues, the physician medication order may not be properly interpreted and filled by the pharmacist or nurse.

Furthermore, in a paper-based care environment after the patient receives the medication, the patient's medical condition and response to treatment is not available to the physician on an instantaneous basis. The delay in the physician receiving information on the patient's condition may have harmful consequences for the patient's treatment because of adverse medication events and other errors resulting from treatment. Thus, an interconnected computer hardware and software system and method is required that will allow the physician prescribing the medication, the pharmacist filling the medication order, the nurse administering the medication and monitoring the patient's condition after receiving the medication to transmit and receive instantaneous up-to-date information in a closed loop.

SUMMARY OF THE INVENTION

The deficiencies of the prior art described above are solved in large part by a closed loop medication use system and method ("CLMUSM") in accordance with the present invention. The CLMUSM includes a physician using a computer device connected to a network, such as a personal digital assistant ("PDA"), laptop, local terminal within the patient-care site, or personal computer at a remote location, to select a medication to be prescribed for a patient. The patient-care site may be a hospital, nursing home, ambulatory care facility, physician's office, home care environment, or other alternate care site. In selecting the medication, the physician, via the computer device, is provided clinical data including real-time patient specific information, specific hospital standards of care, and recommended healthcare industry practices, procedures and treatments. The clinical data provides the physician with alerts concerning patient allergies and possible medication interactions. In a further aspect of this invention, the clinical data provides the physician with alternative treatments and a comparison cost of the treatments. In another aspect of the invention, the physician is allowed to input a search string, to search for a medication to prescribe. Once the physician has determined the medication to be prescribed, using the computer device, the physician prescribes the medication in the form of an unverified prescription order.

In a further aspect of an embodiment of the present invention, the physician may prescribe the medication by handwriting the prescription, or by using a pre-printed form (e.g. a form that has check boxes and medications typically prescribed by the physician). In this aspect, the physician, an assistant to the physician, or another designated person, scans or faxes the prescription, which uses an imaging technology to convert the prescription into electronic form. In this aspect, the physician's unverified prescription order is electronically communicated to the transcribing portion of the CLMUSM.

Next, the unverified prescription order is submitted to the transcribing portion of the CLMUSM. The unverified prescription order is placed into a pharmacist work queue that may contain other unverified prescription orders. A scheduling technique is used to prioritize a new unverified prescription order into the list of pre-existing unverified prescription orders in the pharmacist's work queue. In one embodiment of the present invention, the unverified prescription order is placed in the pharmacist work queue on a first in first out basis. In an alternative embodiment, the unverified order is placed in a pharmacist work queue based on its priority. For example, if an unverified order is tagged as a STAT (fill with highest priority) medication, the unverified order would be placed in the work queue to precede lower priority orders. In another embodiment, the unverified orders are placed in the pharmacist work queue based on the required administration time. In a further aspect of this embodiment, an expert system determines the work queue order based on several factors, such as floor location of patient, and the estimated time required for the pharmacist to verify the order.

The transcribing portion of the CLMUSM includes pharmacist or nurse review of the appropriateness of the unverified prescription order, by examining real-time patient information, such as allergies, diet, laboratory data, and medications the patient is taking, and by examining medication information for possible adverse medication interactions and any administering guidelines or requirements. Once the clinician has reviewed the unverified prescription order, the clinician can use the transcribing portion to verify the order, modify the order, and/or send a communication alert to the prescribing portion with messages regarding the unverified order.

Once the order is verified, the transcribing portion determines the best dispensing method for the verified order. In one embodiment the dispensing method is determined based on the patient's location, the medication administered, and location and quantity of the medication at a dispensing location. In a further aspect of this embodiment, the dispensing portion of the CLMUSM includes a robotic medication system that automatically dispenses verified prescription orders received from the transcribing portion. In yet another aspect of this embodiment, the dispensing portion of the CLMUSM may include an automated storage and retrieval system product. This system dispenses bar-coded product through the use of pick-to-light technology for use in both fulfilling patient orders received from the transcribing portion, as well as for processing replenishment orders for medication dispensing cabinets and remote pharmacy locations. In still a further aspect of this embodiment, the dispensing portion of the CLMUSM may include unit-based medication-dispensing cabinets (UBCS) that can be located at numerous locations around a patient-care site. In this embodiment, UBCs have computer systems that receive verified orders from the transcribing portion of the CLMUSM. Access to medications contained in the UBC is restricted to specific users, such as the administering clinician, and to only those medications contained within the UBC for which verified prescription orders from the transcribing portion of the CLMUSM exist.

In a further aspect of this embodiment, the medication housed within the UBC is contained in bar-coded packets. The bar-coded packets can be supplied via the use of specialized packaging systems, which provides both bulk and unit-dose packaging and bar coding of medication. Upon retrieval of a medication packet, the clinician is prompted to scan the packet's bar code using a scanner in communication with the UBC's computer system. The dispensing portion of the CLMUSM verifies that the clinician has selected the correct medication, using data from a patient information database (DB) and a prescription order database (DB). In a further aspect of this embodiment, the scanning of the bar-coded medication the clinician has retrieved may be used as a tracking system, which tracks the dispensed medications. The system may generate data representative of the dispensed medication.

Once the medication is dispensed, the administering clinician proceeds to administer the medication. In one embodiment of the present invention, the administering clinician uses a computer device, such as a wireless scanning device having a graphical user interface, or in another embodiment a laptop having a scanning device attached, or in another embodiment a computing device having a scanning device attached that is located in the patient's room, to select a patient to administer medication. In a further aspect of this embodiment, the computer device indicates to the clinician a list of patients requiring medication administration. The clinician selects the patient from the list, and a list of verified prescription orders for the selected patient can be displayed to the clinician, indicating the administering time of each medication. In still a further aspect of this embodiment, the status of the verified order is also displayed, such as whether or not the prescription order has been dispensed.

Using the computer device, the administering clinician scans the medication to be administered and scans the receiving patient's bar code. The bar code may be located on a wristband, ankle band or attached to another part of the patient using an attachment device. The patient may also be identified to the administering clinician by an electronic chip, integrated circuit, or other unique identifier. The administering portion of the CLMUSM performs several crosschecks to determine if this is the right patient, right medication, right dosage, right route and right timing of administration. These crosschecks access real-time patient information, such as laboratory test results, patient allergies, medication the patient is currently taking, as well as the timing of previous administered medication, in order to assist the administering clinician in the determination of the five rights of medication administration. Once the medication is administered to the patient, the administration is recorded and stored in the patient's information record. In addition, observations and patient data such as blood pressure, pain scale, sugar level, etc., related to the administering of the medication are recorded as part of the administering event.

The CLMUSM also includes a monitoring portion, which continuously collects information received from all parts of the CLMUSM, and communicates this patient information in real-time to all parts of the CLMUSM. This real-time patient information includes laboratory results, radiology results, unverified and verified prescription orders, scheduled tests, administered medication, adverse medication reactions, allergies, patient observations, vital signs, intravenous ("IV") infusion rates and the cost of the patient's treatment. The monitoring portion also includes the monitoring in real-time of clinically recommended standards of care and patient-care site charges.

In a further embodiment of the present invention, the CLMUSM, using the real-time patient information provided by the monitoring portion, automatically generates and provides to the clinician specific patient information based on health care industry recommended medication practices and/or facility specific information regarding specific patient data that should be considered when prescribing a medication. In this embodiment the generated data can also be displayed to present the physician with specific patient information considered by the prescribing portion in recommending a method of treatment or medication to the physician. The generated data can be in various forms, such as graphs, charts, tabular data, or text.

Further embodiments of the CLMUSM of the present invention include, the prescribing, transcribing, dispensing, administering, and monitoring steps being connected over a network, the World Wide Web ("WWW"), or an Intranet. In a further aspect of this embodiment, multiple patient-care sites are connected over a Wide Area Network ("WAN"), in order to allow physicians and pharmacists to prescribe and transcribe medication, respectively, using the CLMUSM at a variety of patient-care sites. This WAN connection of multiple patient-care sites will allow a pharmacist at one patient-care site to transcribe and verify unverified prescription orders at a second patient-care site, providing a more efficient and less costly use of patient-care site resources.

In still a further aspect of this invention, the CLMUSM allows communication and message sharing between the prescribing, transcribing, dispensing, administering, and monitoring modules using any suitable interfacing protocol, such as a Health Level Seven ("HL7") interface. The interfacing between two or more modules can be a direct interface or data communication between the modules using network-interfacing methods. In a further aspect of this embodiment, multiple, dissimilar interfacing protocols and methods are used to allow communication between the various modules of the CLMUSM.

In another embodiment of the present invention, the CLMUSM provides a significant amount of feedback, error checking, and clinical cross checking by performing multiple checking of medication interaction data and real-time patient information in each of the prescribing, transcribing, dispensing, administering, and monitoring modules, in order to help assure appropriate medication use at each module. In a further aspect of this embodiment, the feedback and clinical cross checking are used to reduce medical costs caused by repeating medical tests or administering medication, that based on the real-time patient information, are no longer required. In still a further aspect of this embodiment, the continuously monitored real-time patient information is continuously compared with predetermined alert values; and upon a predetermined result value of the comparison an alert is communicated to the appropriate prescribing, transcribing, dispensing, administering, and monitoring modules.

In another embodiment of the present invention, healthcare best practice guidelines for decision making and diagnosis, and detailed medication information are provided as inputs to the prescribing step of the CLMUSM. In this embodiment, based on medically specific patient condition information a list of medication treatments for the patient is generated. In a further aspect of this embodiment, the healthcare best practice guidelines for decision making and diagnosis are nationally or locally provided and updated for the caregiver. In still a further aspect of this embodiment, the healthcare best practice guidelines for decision making and diagnosis implement the knowledge of experts, including the results of medical studies, white papers, research, and lectures. In still a further aspect of this embodiment, the healthcare best practice guidelines are provided on a real-time basis to the physician during decision making and diagnosis.

In still another embodiment of the present invention, the CLMUSM allows computerized prescription order entry using text recognition and subsequent conversion of the next into Unified Medical Language System ("UMLS").

BRIEF DESCRIPTION OF THE DRAWINGS

FIGS. 4, 4A and 4B are flow diagrams of the prescribing portion of the closed loop medication use method showing prescription order entry and clinical decision support;

FIG. 5 shows the physician inputting a search string to find a medication match an patient information that is available to the physician in the prescribing portion of the CLMUSM;

FIG. 6 shows a screen shot of recommended medication orders based on the patient's condition in the prescribing portion of the CLMUSM;

FIG. 7 shows a screen shot of algorithms for determination of appropriate medication dosages in the prescribing portion of the CLMUSM;

FIG. 8 shows a screen shot of a list of recommended medication treatment regimens along with the cost of each regimen in the prescribing portion of the CLMUSM;

FIG. 9 shows a screen shot of an alert that includes patient-care site specific recommendations to use the medication Cefepime over the medication Ceftazidime in the prescribing portion of the CLMUSM;

FIG. 10 shows a screen shot of healthcare industry and patient-care site specific guidelines for the treatment of Confirmed PE in Adults in the prescribing portion of the CLMUSM;

FIGS. 12, 12A and 12B are flow diagrams of the transcribing portion of the closed loop medication use method showing the receiving and processing of prescription orders;

FIG. 13 shows a screen shot of a pharmacist work queue in the transcribing application that identifies a patient, pharmacist action needed and description of prescribed medication;

FIGS. 14-15 show screen shots of the pharmacist's selection and verification of a prescription order;

FIG. 16 shows the tasks in the pharmacist work queue prioritized based on the scheduled administration of the medication;

FIGS. 18, 18A and 18B are flow diagrams of the dispensing portion of the closed loop medication use method showing dispensing of medicine to a Nurse;

FIGS. 19-20 show a screen shot depicting patients queued for dispensing from system;

FIGS. 24, 24A and 24B are flow diagrams of the administering portion of the closed loop medication use method showing administration of medicine to a patient;

FIG. 25 shows a screen shot from a wireless scanner display of a nurse's census;

FIG. 26 shows a screen shot from a wireless scanner display of the administration time, type of medication, and dosage to be administered to a patient;

NOTATION AND NOMENCLATURE

Certain terms are used throughout the following description and claims to refer to a particular system components and processes. As one skilled in the art will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ". Also, the term "couple" or "couples" is intended to mean either an indirect or direct electrical connection. Thus, if a first device couples to a second device, that connection may be through a direct electrical connection, or through an indirect electrical connection via other devices and connections.

DESCRIPTION OF ILLUSTRATIVE EMBODIMENTS

Figure 1:
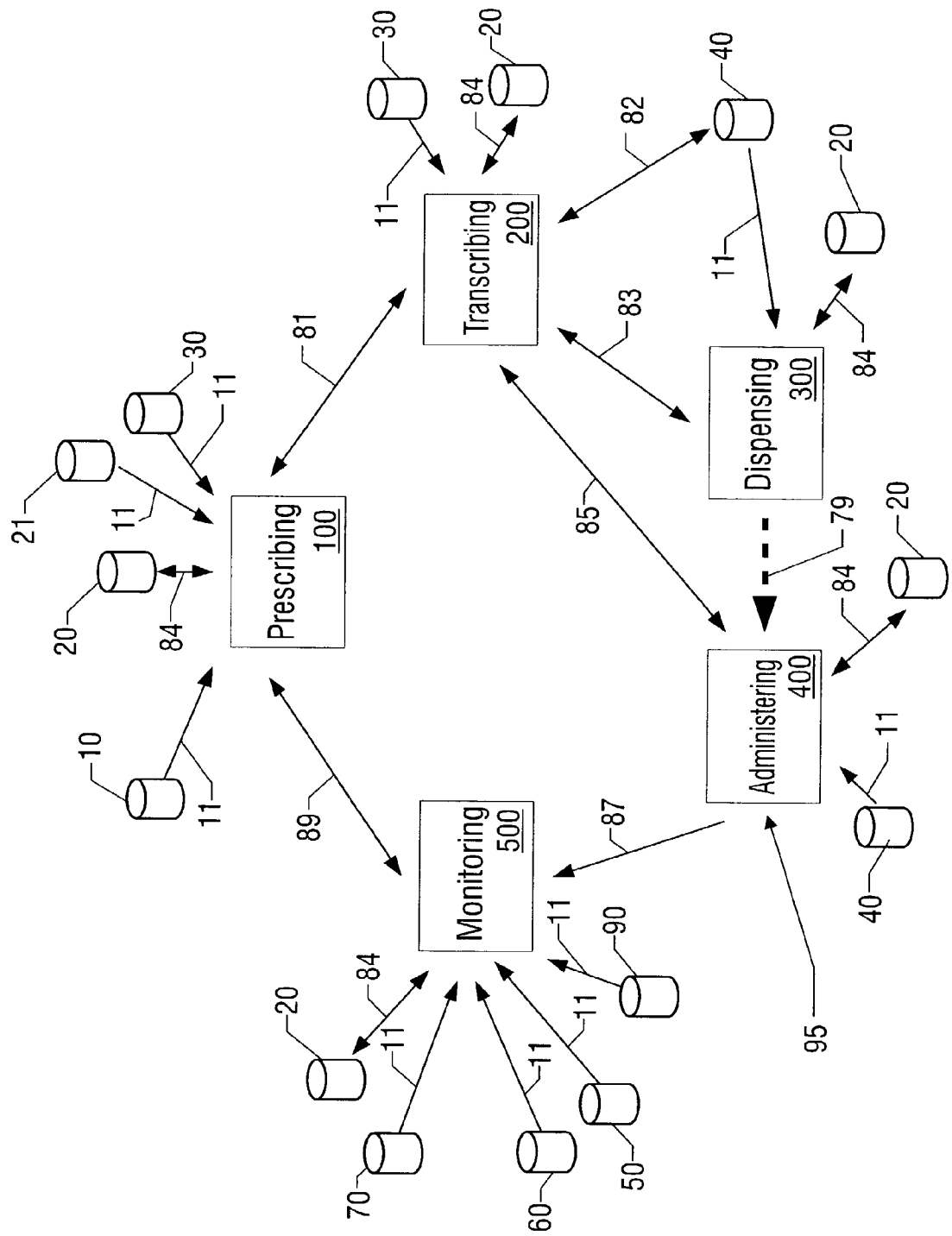
FIG. 1 is a block diagram of a closed loop medication use system in accordance with an embodiment of the present invention.

FIG. 1 is an illustrative embodiment of the CLMUSM in accordance with one embodiment of the invention. As illustrated, the CLMUSM includes a prescribing module 100, a transcribing module 200, a dispensing module 300, an administering module 400, and a monitoring module 500. Each module includes hardware devices and software to perform various functions required of that module. These modules can be interconnected over any suitable networking system such as a LAN, WAN, Intranet, or Internet. Additionally, the modules in the various embodiments can be interfaced using a HL7 messaging protocol, a SQL direct access interface, or any suitable interfacing protocol. It can also be appreciated that communication between the various modules 100-500 can be done using a combination of interfacing protocols. For example, in an embodiment of the present invention shown in FIG. 1, the prescribing-transcribing interface 81 between the prescribing 100 and transcribing 200 modules can be implemented using a HL7 protocol. In the same embodiment, the transcribing-dispensing interface 83 between the transcribing 200 and dispensing 300 modules can be implemented using a SQL direct access interface. Although specific communication protocols have been referenced herein, it should be understood that any suitable communication protocol or combination of communication protocols can be used, and are within the scope of the present invention.

In one aspect, the prescribing module 100 is a prescription order entry and clinical decisions support module that allows users, such as physicians, to prescribe medication based on patient specific information. Furthermore, prescribing module 100 allows users to communicate messages to other modules within the CLMUSM, document patient care, and interact with treatment advisors and healthcare industry guidelines at the point of care, typically the patients bedside. In an embodiment of the invention shown in FIG. 1, the prescribing module 100 gives the physician access to a myriad of information in order to provide expert clinical support for the physician's patient medication decisions. The information provided to the physician can include patient specific information, such as demographics, known allergies, and insurance data received from a patient information DB 20. The physician also receives specific medication or medication information, such as medication interaction data, medication side effects, and generic equivalents from a medication information DB 30 and a variety of patient laboratory and radiology results from databases 50 and 60 respectively. In this aspect, the physician receives standard of care information from the monitoring module 500 and verified prescription orders and/or alerts from the transcribing module 200. Further, the physician also receives healthcare industry recommended prescribing and treatment information from a clinical knowledge DB 10.

In an embodiment of the invention shown in FIG. 1, the transcribing module 200 is a pharmacy information system that performs a number of functions. Transcribing module 200 receives prescription orders from the prescribing module 100 and prioritizes the prescription orders. Furthermore, transcribing module 200 provides the pharmacist with relevant patient information received from the patient information DB 20 and medication information from the medication information DB 30. Transcribing module 200, provides the pharmacist with medication dispensing information from the dispensing module 300, such as available medication, dispensing location nearest patient, etc. and allows the pharmacist to verify prescription orders and submit verified orders to a prescription order DB 40 and to the dispensing module 300. In FIG. 1, transcribing module 200 submits alerts and the status of prescription orders to the prescribing module 100 and tasks associated with verified prescription orders to the administering module 400. In addition, transcribing module 200 receives alerts and the administering status of verified prescription orders from the administering module 400.

As shown in FIG. 1, the dispensing module 300 receives tasks associated with the verified prescription orders from the transcribing module 200. Dispensing module 300 pulls verified prescription orders from the prescription orders DB 40 and receives patient information from the patient information DB 20. In FIG. 1, dispensing module 300 also submits dispensing information to the transcribing module 200, such as the availability of medication at various dispensing locations, and a timestamp and identification of the clinician that received the dispensed medication.

FIG. 1 also includes a medication-administering module 400 that assists in the clinician's verification of the five "rights" of medication administration. The five "rights" of medication administration requires verification prior to the administration of the medication to the patient that the right patient receives the right medication in the right dosage through the right route at the right time of administration. In one aspect, administering module 400 includes a clinician, such as a nurse, physically receiving and/or retrieving medication 79 dispensed via the dispensing module 300. The administering module 400 can also receive a medication administration task from the transcribing module 200, based on a verified prescription order. In FIG. 1, administering module 400 retrieves verified prescription orders from the prescription order DB 40 and patient information from the patient information DB 20. Further, administering module 400 submits and receives alerts, comments, and the administering status of verified prescription orders from and/or to the transcribing module 200 and monitoring module 500.

In FIG. 1, monitoring module 500 continuously monitors and evaluates patient information, such as laboratory and radiology test results, allergy information, and prescribed and administered medication. Monitoring module 500 provides real-time medication prescribing information to the physician. Monitoring module 500 evaluates a myriad of information in order to send alerts, and relational, relevant and requested data to the prescribing module 100 and/or other modules within the CLMUSM. The information used for evaluation may include patient information received from the patient information DB 20 and recommended healthcare industry practices and standard of care from database 70. Test results of laboratory and radiology testing from databases 50 and 60 respectively, medication administration information from the administering module 400, and information associated with prescription orders received from the prescribing module 100 may also be evaluated by the monitoring module 500 to send alerts and data to other modules.

One embodiment of the invention as illustrated in FIG. 1 shows several databases that are accessed by each of the individual modules 100-500. For example, patient information DB 20 may be accessed by and updated from all of the individual modules 100-500 over a network connection 84. Other embodiments of the invention may include the information stored on each of the databases 10, 20, 21, 30, 40, 50, 60, 70, and 90 shown in FIG. 1 combined into one database located on a hardware storage medium such as a disk array. Another embodiment may include the database information stored together in any combination of databases (i.e. radiology DB 60 and laboratory DB 50 combination, patient information DB 20 and patient-care site cost factor DB 90 combination), each combination located on a separate hardware storage medium. More details shown in FIG. 1 will be discussed below in reference to the additional figures.

Figure 2:
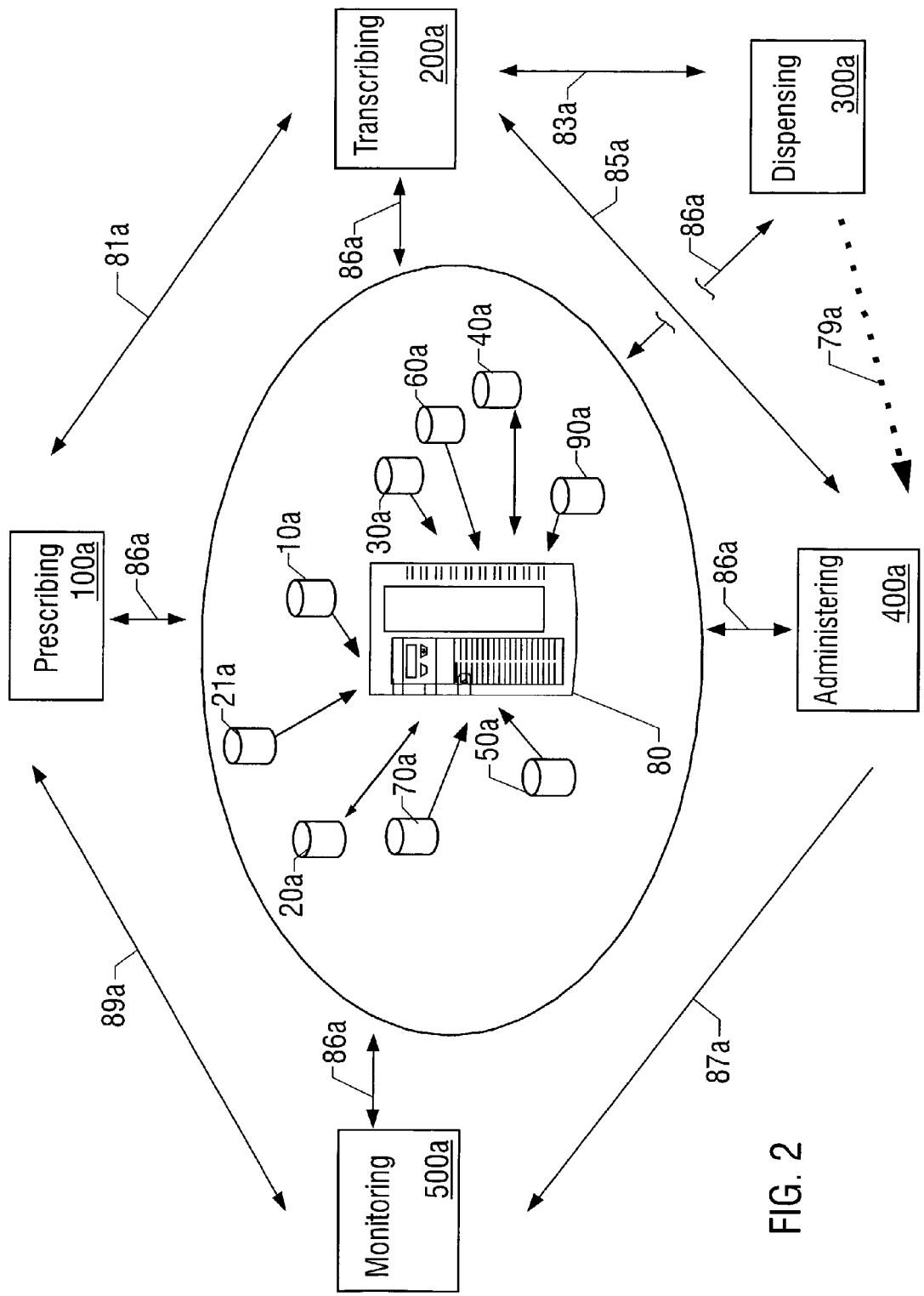
FIGS. 2-2A are block diagrams of alternative embodiments of the closed loop medication use system.

An alternative embodiment of the present invention is shown in FIG. 2. In this embodiment, the prescribing 100a, transcribing 200a, dispensing 300a, administering 400a and monitoring 500a modules connect over a network using interfaces 81a, 83a, 85a, 87a, 89a for direct communication between the modules 100a-500a, respectively. However, all of the databases 10a, 20a, 21a, 30a, 40a, 50a, 60a, 70a, 90a, are coupled through a database server 80 to the various parts of the modules 100a-500a, over network connections 86a. Database server 80 in alternative embodiments may be Intel Pentium®, Intel Xeon®, RISC, PowerPC®, or DEC Alpha® based processor server, a mid-range server such as IBM AS400® or compatible or a high-end server such as IBM Enterprise System 9000® or compatible. It should be understood that any high performance computer server system can be used for database server 80 and is within the scope of the present invention.

Figure 2A:
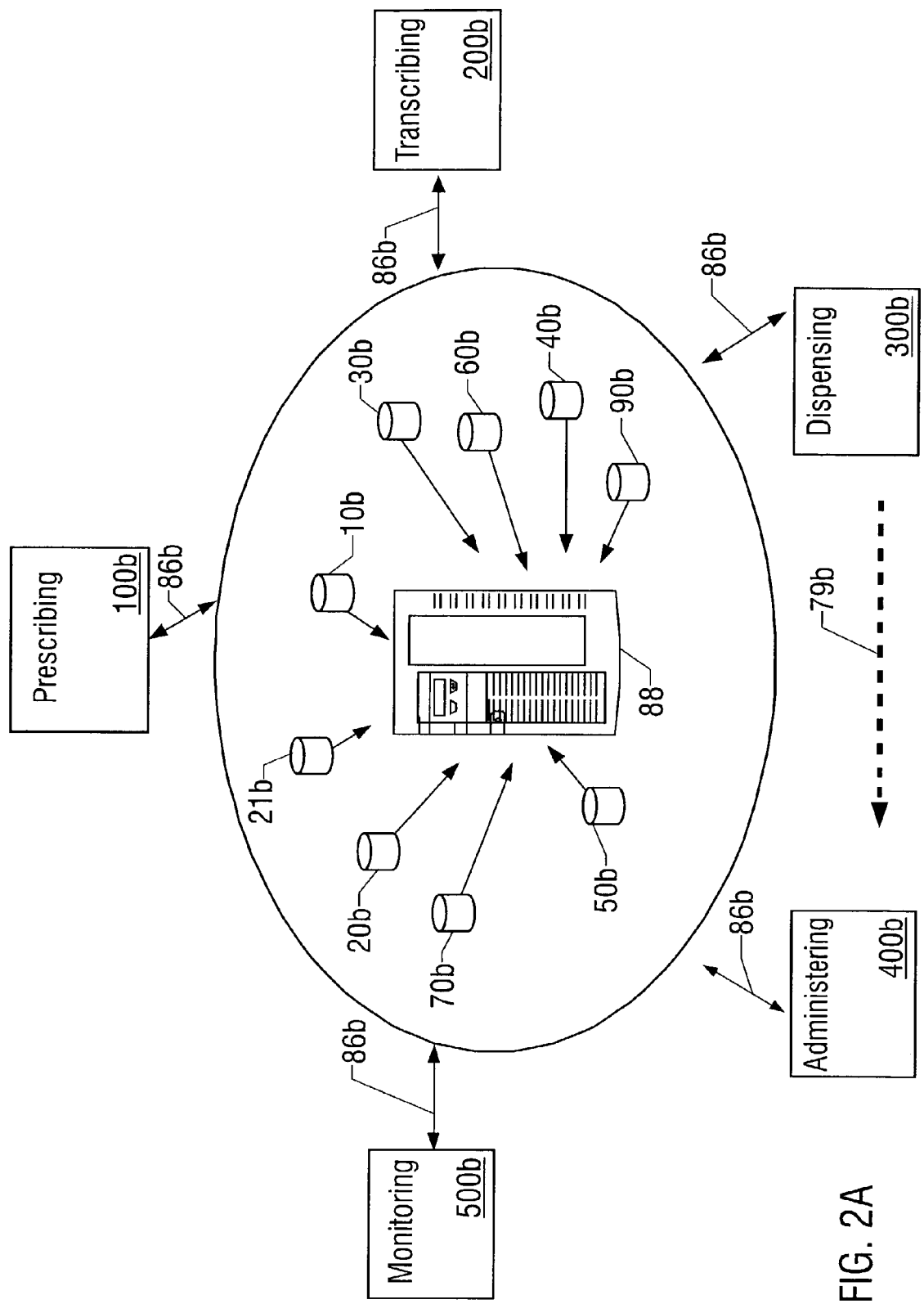

Still another alternative embodiment of the present invention is shown in FIG. 2A. In this centralized server embodiment, all of the databases 10b, 20b, 21b, 30b, 40b, 50b, 60b, 70b, 90b are connected to an application server 88. The prescribing 100b, transcribing 200b, dispensing 300b, administering 400b, and monitoring 500b modules do not have direct interface communication. Rather, the modules 100b-500b are connected to the network via network connections 86b and all communications between the modules are processed using one or more application servers 88. Likewise, communication and transferring of data between the databases 10b, 20b, 30b, 40b, 50b, 60b, 70b, 90b is also channeled through one or more application servers 88. Application server 88 in alternative embodiments may be Intel Pentium®, Intel Xeon®, RISC, PowerPC®, or DEC Alpha® based processor server, a mid-range server such as IBM AS400® or compatible or a high-end server such as IBM Enterprise System 9000® or compatible. It should be understood that any high performance computer server system can be used for application server 88 and is within the scope of the present invention. It can be appreciated that several networking and interfacing configurations can be constructed without departing from the scope of the invention. In reference to the succeeding discussion, the networking and interfacing connection of the prescribing 100, transcribing 200, dispensing 300, administering 400, and monitoring 500 modules as shown in FIG. 1 will be discussed in relation to FIGS. 3 through 46.

Figure 3:
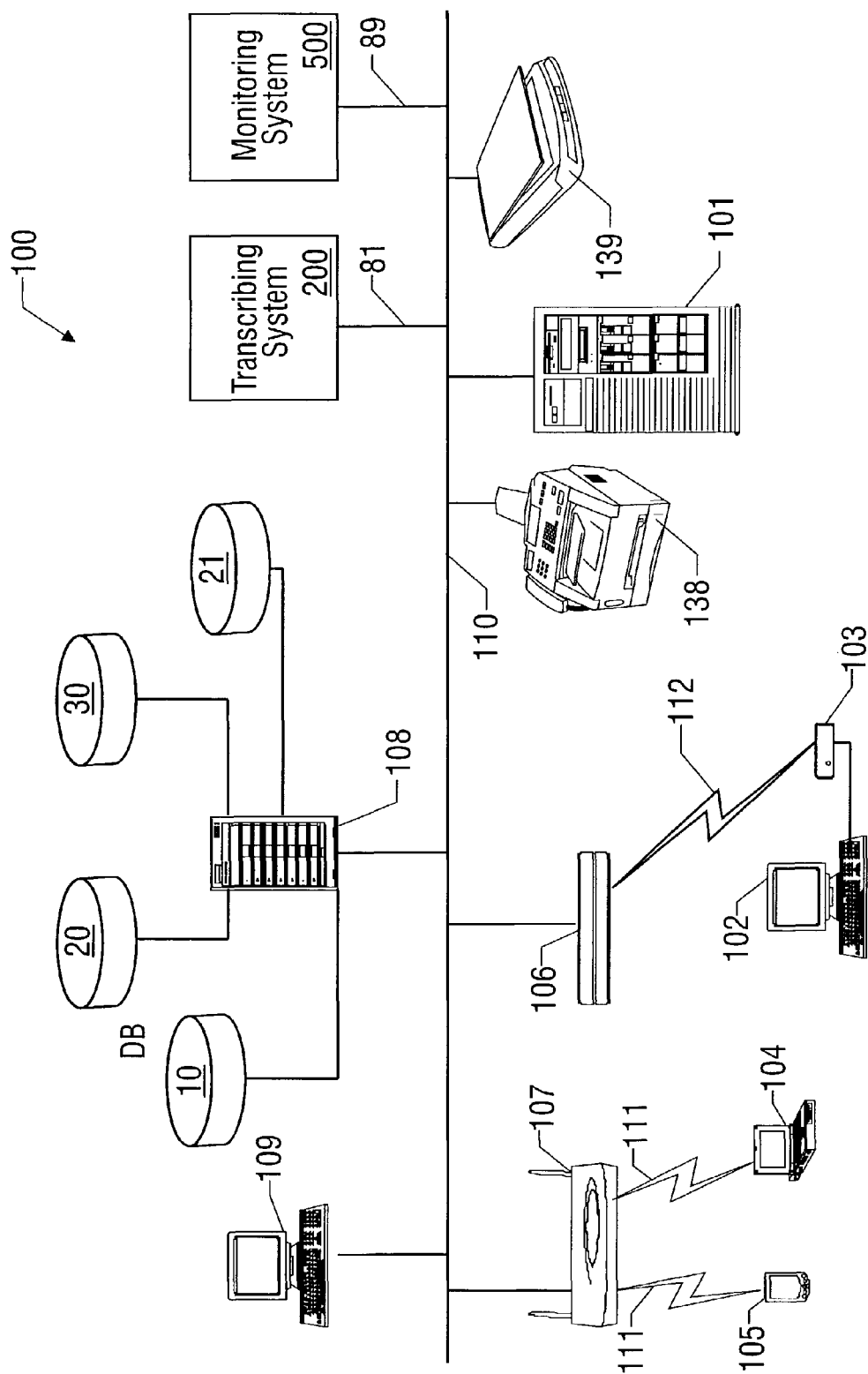
FIG. 3 shows an embodiment of the hardware interconnection of the prescribing portion of the closed loop medication use system.

Turning now to FIG. 3 and referring back to FIG. 1, in one embodiment of the invention, prescribing module 100 is connected to a LAN 110, and includes application server 101 and database server 108. The servers receive data from and transmits data to the patient information database 20, the medication information database 30, the physician database 21, and/or the recommended healthcare industry practices/clinical knowledge database 10. Prescribing module 100 also receives data from and transmits data to both the transcribing module 200 and monitoring module 500 through communications interface 81 and 89, respectively.

The prescribing module 100 provides the physician or clinician authorized to prescribe medications with relevant patient information at the point of care, typically, the patient's bedside. A physician may use a device such as a laptop 104, PDA 105, local terminal in the patient-care site 109, or even a computer at a remote location 102, such as his office or home to log in to the prescribing module 100 and begin the process of prescribing medication to patients. As shown in FIG. 3, a wireless access point 107 is connected to the patient-care site's LAN 110. Using a wireless card in both the PDA 105 and laptop 104 to establish communication links 111, allows the physician to connect to the LAN 110, without the need for cumbersome connection cables (e.g. Ethernet cables or Token Ring cables) and provides increased flexibility for the physician. For even greater flexibility, a prescribing physician at a remote location, utilizing a computer 102 and a modem 103 can connect to the LAN 110 via communication link 112 and remote server 106.

In another aspect illustrated in FIG. 3, the CLMUSM is capable of receiving a medication order from a physician or other clinician via fax machine 138 and scanner 139. In this aspect, the physician or clinician prescribes the medication by handwriting the prescription, or by using a pre-printed form (e.g. a form that has check boxes and medications typically prescribed by the physician). Next, the physician or clinician, or another designated person scans via scanner 139 or faxes via fax machine 138 the prescription. In this aspect, the scanner 139 and fax machine 138 along with a PC for example use an imaging technology to convert the prescription into electronic form. In this aspect, the physician's unverified prescription order is electronically communicated to the transcribing portion of the CLMUSM.

Figure 4B:
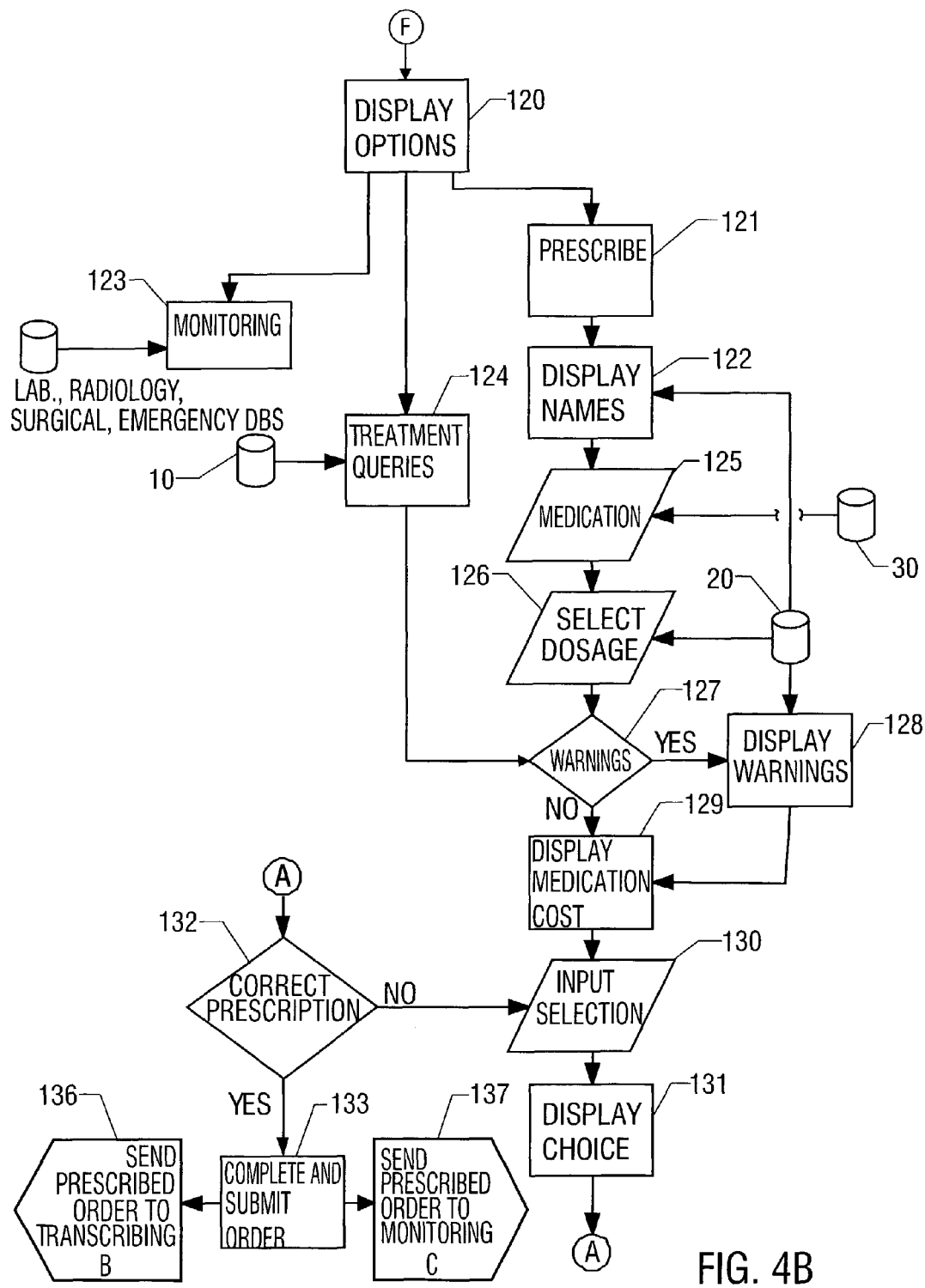

Turning now to FIGS. 4, 4A and 4B, a detailed flowchart of the prescribing module 100 is shown for one embodiment of the invention. Using a processor-based device, such as the PDA 105 shown in FIG. 3, the physician logs into the patient-care site network 113. Next, the physician is given the option 114 to either view alerts 115 or prescribe medication 116. Message alerts to the physician can be in various forms, such as a change in the prescription order by the pharmacist from the transcribing module 200, a message from the monitoring module 500 as to a change in the patient's condition, or test results that should be reviewed prior to prescribing medication. As shown in FIG. 4, pharmacist comments 134 are shown as an input to the view alerts step 1115. In another embodiment of the prescribing module 100, message alerts are immediately presented to the physician after he logs into the patient-care site network 113.

If the physician chooses the prescribe option 1116, the physician is asked to identify the patient 117. Identification of the patient can be done by several methods, such as scanning the patient's bar code or other unique identifier, selecting the patient's name from a stored list, or manually entering the name into the prescribing module. In one embodiment, based on the physician's login information or distinct physician code field in the physician's DB 21, the prescribing module 100 pulls from the patient information DB 20 the names of the physician's patients within the patient-care site's system and generates a list of the physician's patients. From this list, the physician selects a patient 117.

In an alternative embodiment, the physician enters a patient's name 117. Once the patient is identified, the application performs a decisional query 119 to determine if the patients name is found in the prescribing module 110 based on information received from the patient information DB 20. If the name is not found, a message is displayed 118 and the physician is prompted to identify the patient again. In one embodiment, if the patient's name is found, a list of options is displayed 120. The options include retrieving monitoring data 123, which receives input from various databases (laboratory, radiology), as shown in FIG. 1. Other options presented to the physician include viewing recommended treatment methods 124 based on a previously entered patient diagnosis received from the healthcare clinical knowledge DB 10 or prescribing medication 121.

In one embodiment of the invention, if the physician chooses to prescribe medication 121, after the application displays the names of medication 122, the physician can select the desired medication 125. Alternative embodiments for input of the desired medication 125 include input of a medication search string in order to perform a system search of potential medication matches or selecting a medication from a displayed list based on real-time data about the patients condition.

Figure 5:
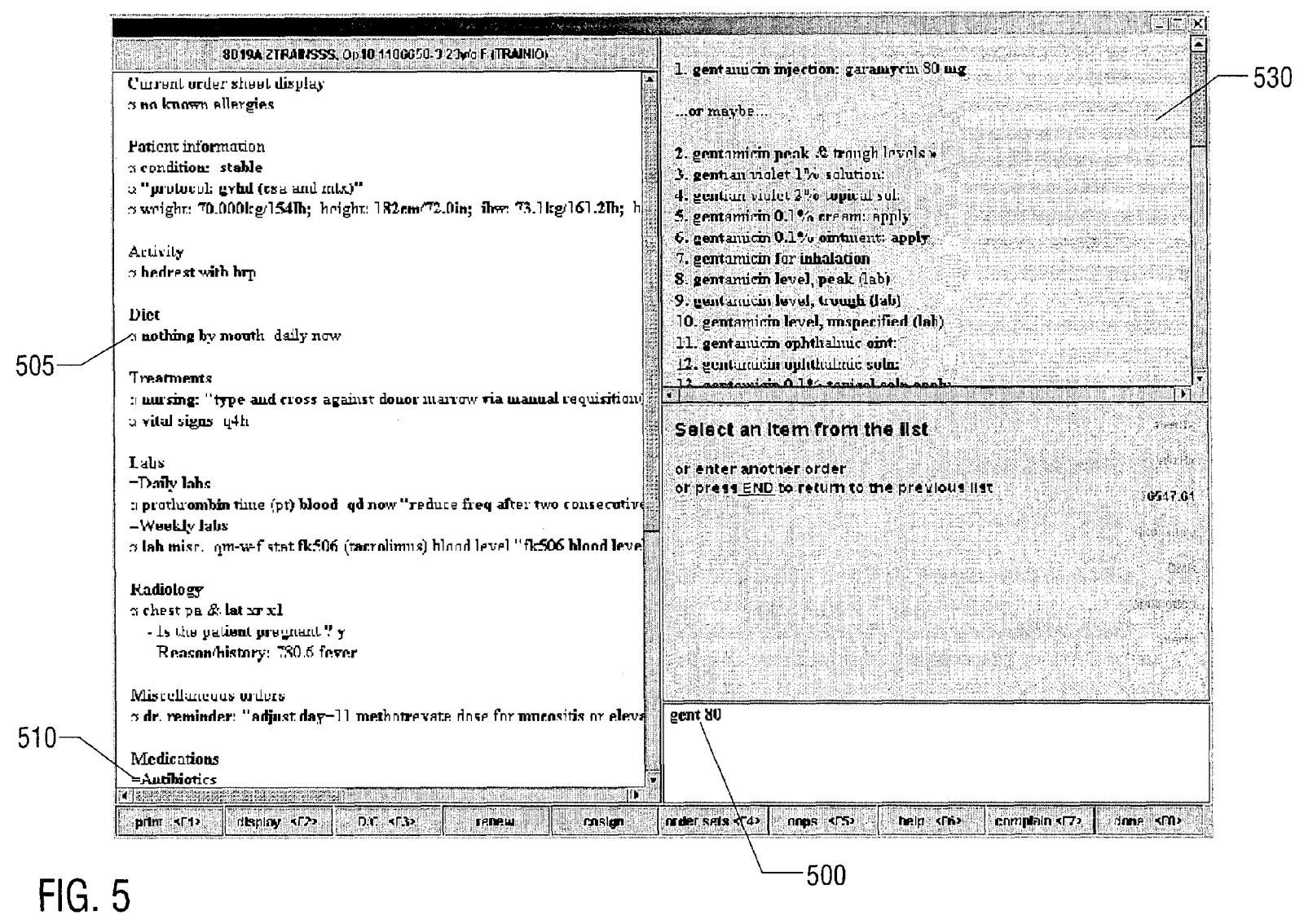

An example of the physician inputting a search string 500 to find a medication match is shown in FIG. 5. FIG. 5 also depicts a screen shot of patient information that is available to the physician in the prescribing module 100. For example, the screen shot shown in FIG. 5 has information 505 regarding any known patient allergies, laboratory, radiology and dietary orders for the patient, the patients weight and height, patient observations, and vital signs of the patient. This screen shot also illustrates the ability of the physician to enter a medication search string 500 by inputting the type of medication to be prescribed and a portion of the medication's name.

As shown in FIG. 5, the physician has selected an antibiotic 510 as the type of medication to be prescribed. A search window 500 in the bottom right hand side of the screen allows the physician to input a search expression. This search expression can be a BOOLEAN type search, or any other suitable search method. As shown, the physician inputs the search string "gent 80". In one embodiment of the invention, the prescribing module 100 searches the medication information DB 30 for possible hits and indicates the most probable match first, and sorts other potential medication matches based on a predetermined criteria. In this instance, the screen shot shown in FIG. 5 indicates that the prescribing module 100, returned "1. gentamicin injection: garamycin 80 mg" 530 as the most probable match. Gentamicin is the generic name of the antibiotic medication and Garamycin® is the brand name of the medication.

In one embodiment of the present invention, the medication matches are sorted based on the most commonly prescribed medication. The prescribing module 100 may be an expert system that can generate several different determinations of the most commonly prescribed medication. One determination is based on the overall healthcare industry's most commonly prescribed medication that is closest to the search string entered by the physician. In order to provide a sorted list based on this criteria, the prescribing module 100 queries the medication information DB 30 and/or the clinical knowledge DB 10.

Another determination of the most commonly prescribed medication is based on the specific patient-care site's most commonly prescribed medication that is closest to the physician's search string. In this instance, the prescribing module 100 transmits a query to the monitoring module 500 that extracts from the patient-care site's standard of care DB 70 and medication information DB 30 the patient-care site's most commonly prescribed medication that is closest to the search string entered by the physician.

In another embodiment, the most commonly prescribed medication can be based on the individual physician's or the individual patient's most commonly prescribed medication, based on information from the physician's DB 21, or the patient information DB 20, respectively. Still other determinations of the most commonly prescribed medication closest to the physician's search string can be based on a combination of information from the healthcare industry DB 10, medication information DB 30, physician's DB 21, patient information DB 20, and the patient-care site's standard of care DB 70.

In another embodiment of this invention, rather than being based on the most common type of medication, the medication matches are sorted based on the patient's real time information, such as the patient's inability to ingest medication in the form of solid oral dosage forms, thereby requiring a liquid dosage, injected dosage, or a dosage administered by IV fluids. The real-time patient information is updated by the monitoring module 500 for storage into the patient information DB 20. After an initial sort by the expert system rule set based on the patient's real-time monitoring information, a secondary expert system sort based on one or more of the previously mentioned commonality features can also be performed. For example, if the patients real-time monitoring information indicates the patients inability to ingest solid oral dosage forms, the prescribing module 100 will sort the list of potential medication matches for the search string, based on a primary criteria of the available routes of medication (i.e. ingestion of a liquid dosage, injection by needle, or dosage by IV fluids). The prescribing module 100, in one embodiment, will then perform a secondary sort on the list of non-solid oral dosage forms route potential medication matches using a secondary criteria of the physician's most commonly prescribed medication for the search string, received from the physician information DB 21. Still other real-time information that provides primary criteria for a medication search string includes patient allergies and potential conflicts between any medication patient is currently taking, which is received from the patient information DB 20.

Referring back to FIGS. 4, 4A and 4B, once a list of medication names 122 is displayed, the physician is prompted to input the desired medication choice 125. In the next step of one aspect of the invention, the physician is prompted to select the dosage 126, the application then determines if there are any associated warnings with the selection and dosage of the medication 127. Warnings can include, allergic reaction information based on information from the patient information DB 20, medication interaction warnings based on data from the patient information DB 20 and the medication information DB 30. If warnings are required, these warnings are displayed to the physician in step 128. If there are no warnings, a cost comparison of comparable medication is performed and a list with the costs of the proposed medication and the comparable medication is displayed 129. Next the physician selects the final medication choice 130, the medication choice is displayed 131, verified with the correct prescription 132, and the prescription order is submitted 133 to the transcribing module 200 and monitoring module 500, as shown by outputs 136, 137 respectively.

In addition to providing the physician with a list of medication to prescribe to the patient, the prescribing module 100 as shown in the screen shot of FIG. 6 also provides the physician with recommended prescription orders 610 based on the patient's condition and algorithms 710 for determination of appropriate medication dosages as shown in the screen shot of FIG. 7.

In another embodiment of the invention, the prescribing module 100 also allows the physician to view recommended healthcare industry practices associated with a patient's disease, and provides the physician with complete medication order regimens as shown in FIG. 8. Based on patient information received from the patient information DB 20 and healthcare industry practices received from the clinical knowledge DB 10, a list of recommended medication treatment regimens 820 is displayed along with the cost of each regimen 830 as shown in FIG. 8. This cost comparison allows the prescribing physician the ability to control the cost of the patient's medication treatment. Although the clinical knowledge DB 10 provides the physician with recommended medication orders, the specific patient-care site may have additional practices, procedures, and recommendations with regard to specific medication, based on information in the patient-care site's standard of care DB 70, as shown in FIG. 9.

Figure 9:
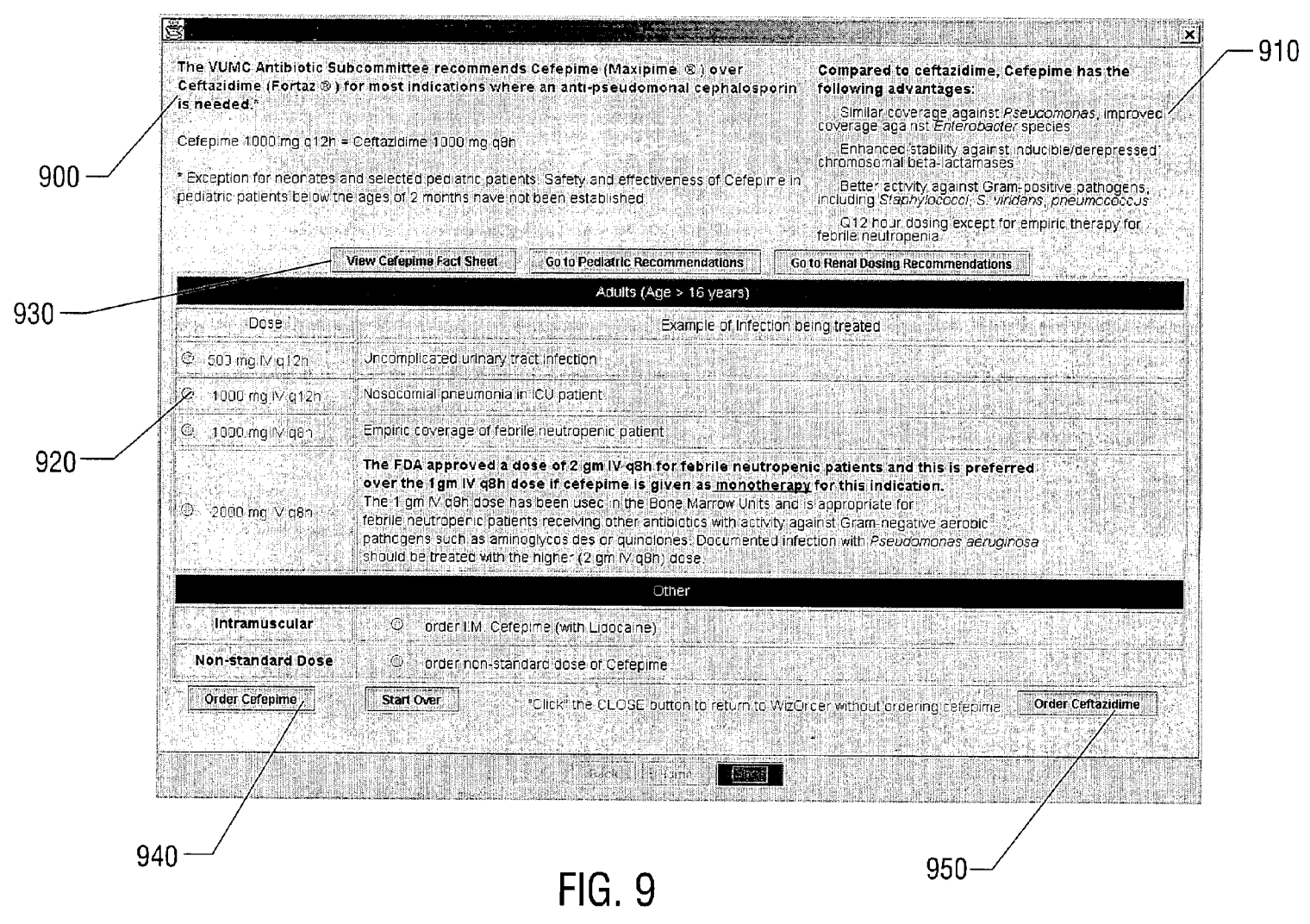

If the physician selects the first recommended medication regimen depicted in FIG. 8, which includes a dosage of 1000 mg of Cefiazidime an alert is displayed as is shown in FIG. 9. In FIG. 9, patient-care site specific information indicates that a subcommittee within the patient-care site recommends the medication Cefepime over the medication Ceftazidime 900. In this embodiment, the prescribing module 100, gives a comparison of the medications 910, gives any exceptions to its recommendations, provides recommended dosage of the suggested medication based on the patients symptom or particular illness being treated 920, and gives the physician the option to view a complete fact sheet for the medication 930.

Although the prescribing module 100 provides the physician with recommended medication practices, specific to the patient-care site, the prescribing module 100 allows the physician to make the final medication decision. As shown in FIG. 9, the physician has the option to order the recommended Cefepime 940 and also has the option to select the Ceftazidime 950.

Turning now to FIG. 10, in another embodiment of the present invention, the prescribing module 100 also provides the physician with healthcare industry and patient-care site specific guidelines for the treatment of patient medical conditions. Once the physician has selected a medication, any special treatment guidelines associated with the medication are displayed. In the exemplary screen shot illustrated in FIG. 10, guidelines 1010 and a checklist 1020 for the treatment of Confirmed PE in adults using the medication heparin intravenously is shown. As shown, the prescribing module 100 displays relevant clinical data such as medication and lab values that should be specifically checked when prescribing this medication. Since the final decision remains with the physician, should the physician choose to decline any recommended orders, an input box 1040 allows the physician to indicate his/her reason for not adhering to the suggestions.

Figure 11:
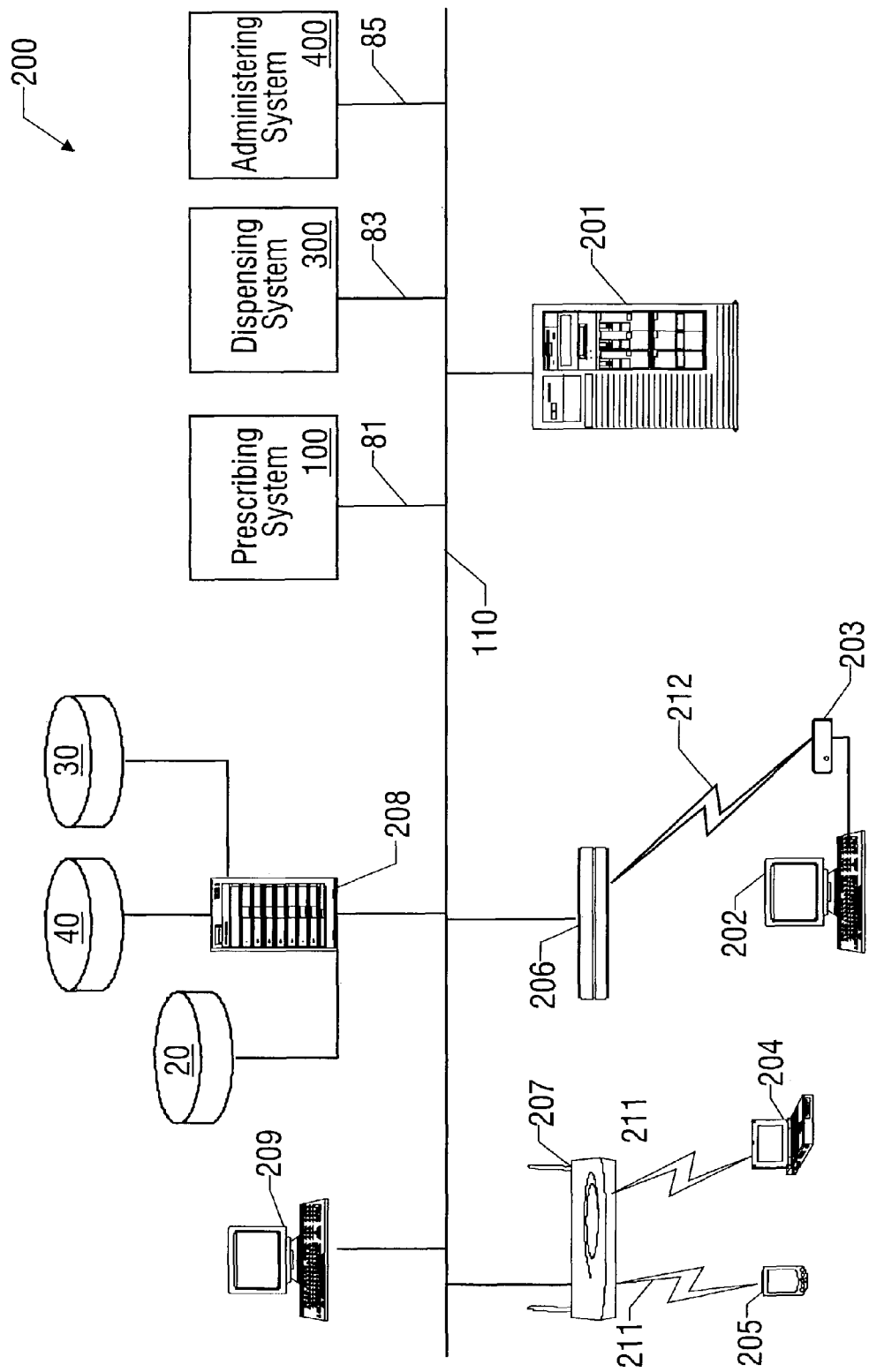
FIG. 11 shows an embodiment of the hardware interconnection of the transcribing portion of the closed loop medication use system.

Turning now to FIG. 11 and referring also to FIG. 1, once the physician has entered a prescription order, the prescribing module 100 transmits the prescription order to the transcribing module 200. The transcribing module 200 is connected to the patient-care site's LAN 110, and includes application server 201 and database server 208, which receives data from and transmits data to the patient information DB 20, the medication information DB 30, and/or to the prescription order DB 40. The transcribing module 200 also receives data from and transmits data to the prescribing 100, dispensing 300, and administering 400 modules through communication interfaces 81, 83, and 85, respectively.

The transcribing module 200 provides the transcribing pharmacist with relevant patient information from the patient information DB 20, such as allergies, and the patient's medication therapy. The pharmacist uses a computer such as a laptop 204, PDA 205, local terminal in the patient-care site 209, or even a computer at a remote location 202, such as his office or home in order to log in to the transcribing module 200 and begin the process of verifying prescription orders received from the prescribing module 100. As shown in FIG. 11, a wireless access point 207 is connected to the patient-care site's LAN 110. Using a wireless card in both the PDA 205 and laptop 204 to establish communication links 211, allows the pharmacist to be connected to the LAN 110 without the need for cumbersome connection cables (e.g. Ethernet cables or Token Ring cables) and provides increased flexibility for the pharmacist. Although FIG. 11, identifies the wireless access point 207 as a separate access point from the wireless access point 107 shown in FIG. 3, in the typical networking environment, the physician and pharmacist could be in a relatively close vicinity, whereby both the pharmacist and the physician are connected to the patient-care site's LAN 110, via the same wireless access point. For even greater flexibility, in an alternative embodiment, the pharmacist can be at a remote location, utilizing a computer 202 and a modem 203 can connect to the LAN 110 via communication link 212 and remote server 206.

Figure 12B:
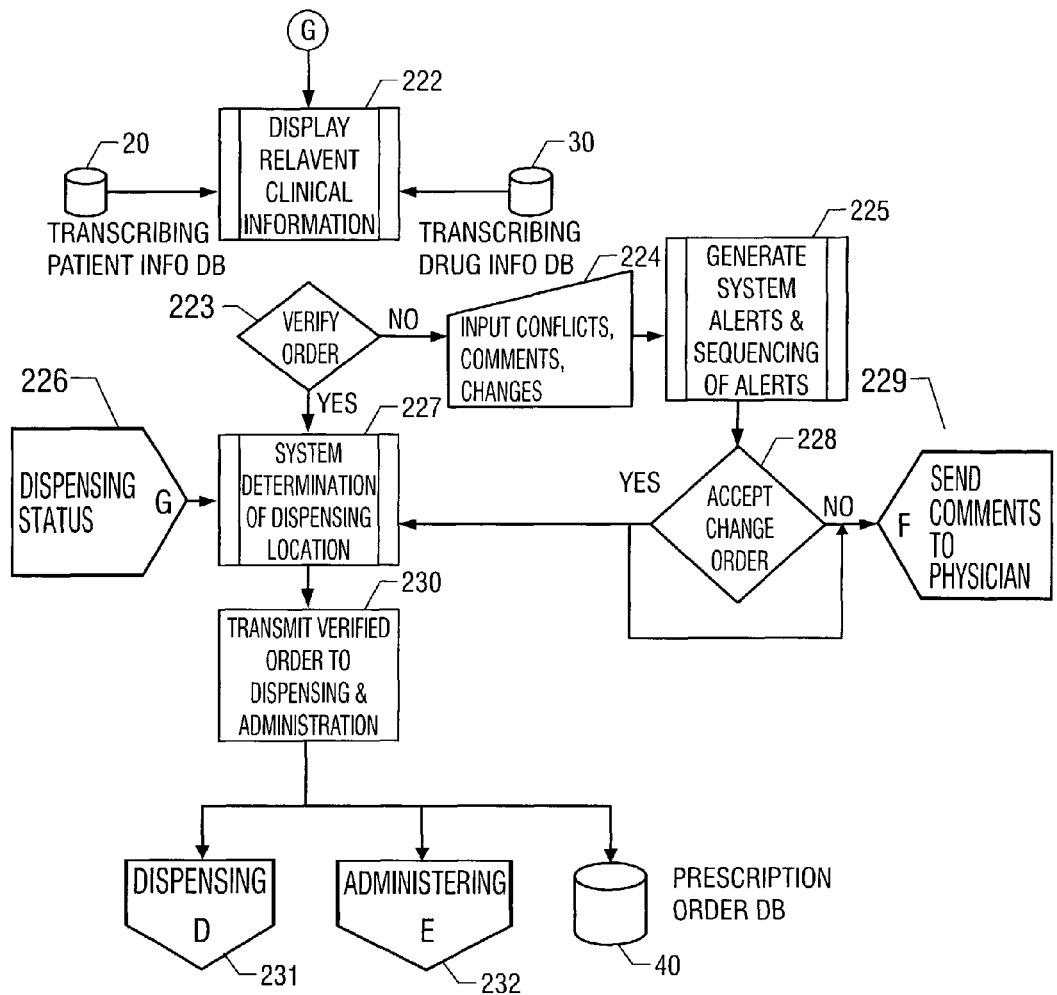
Figure 13:
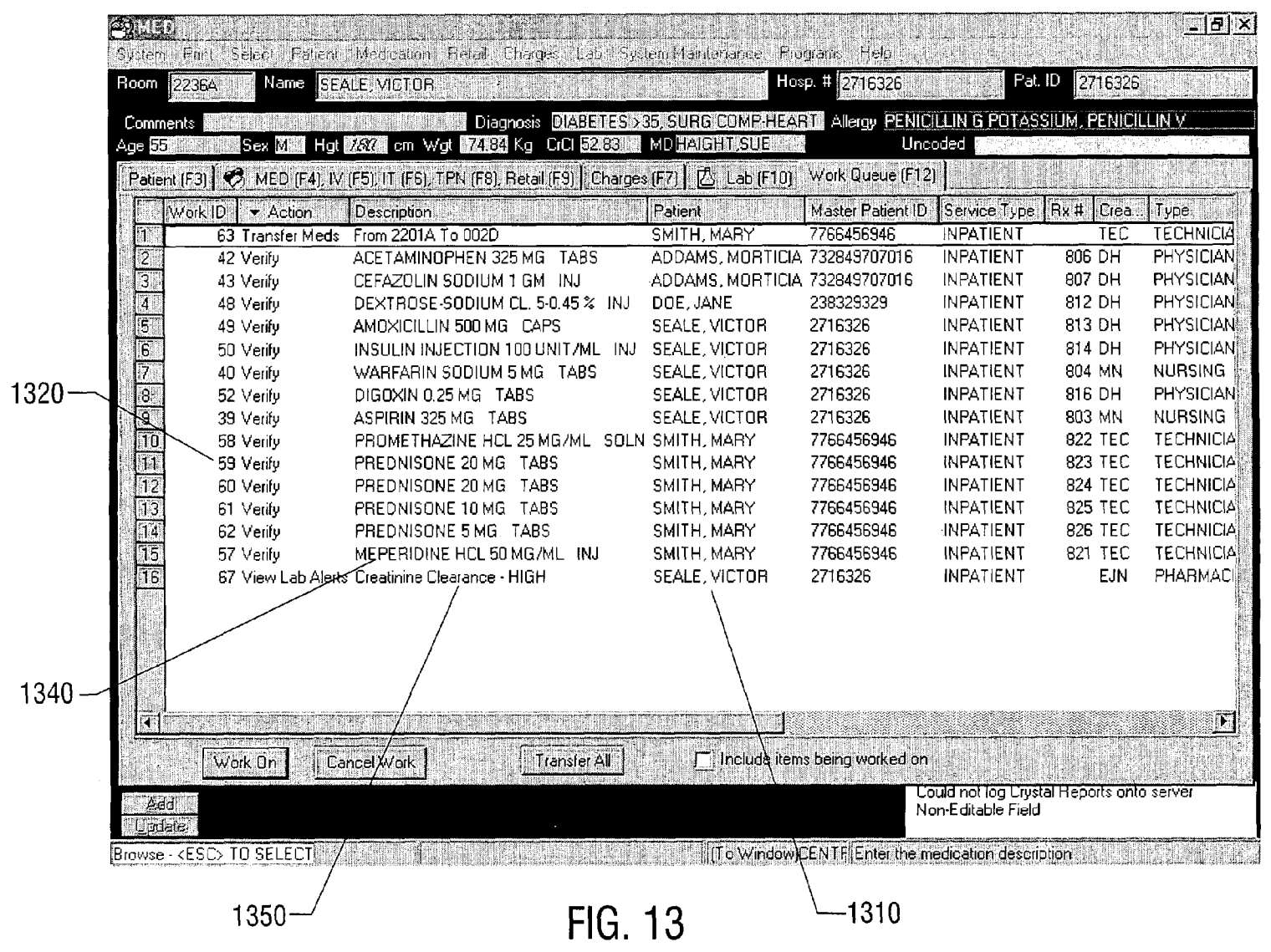
Figure 14:
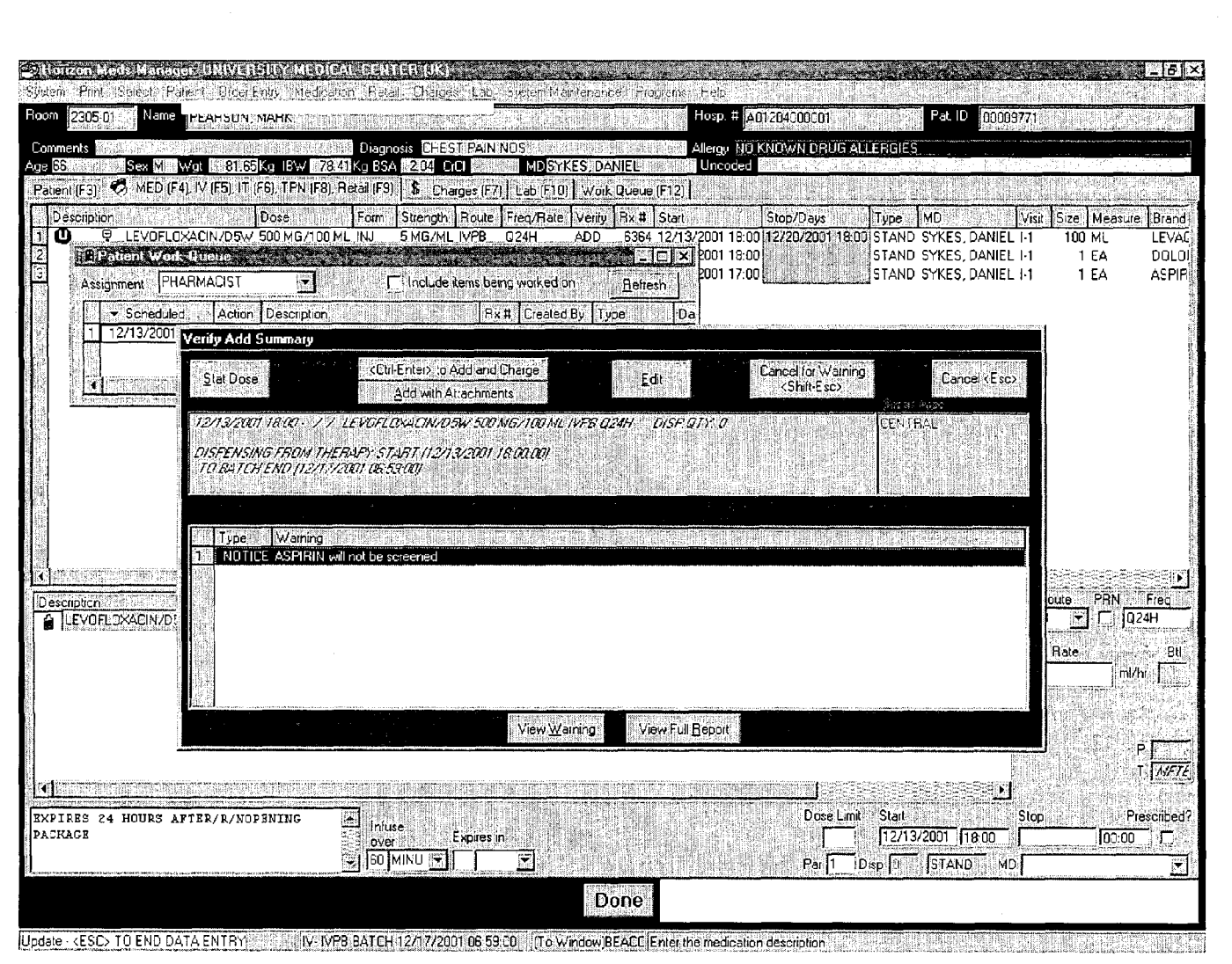
Figure 15:
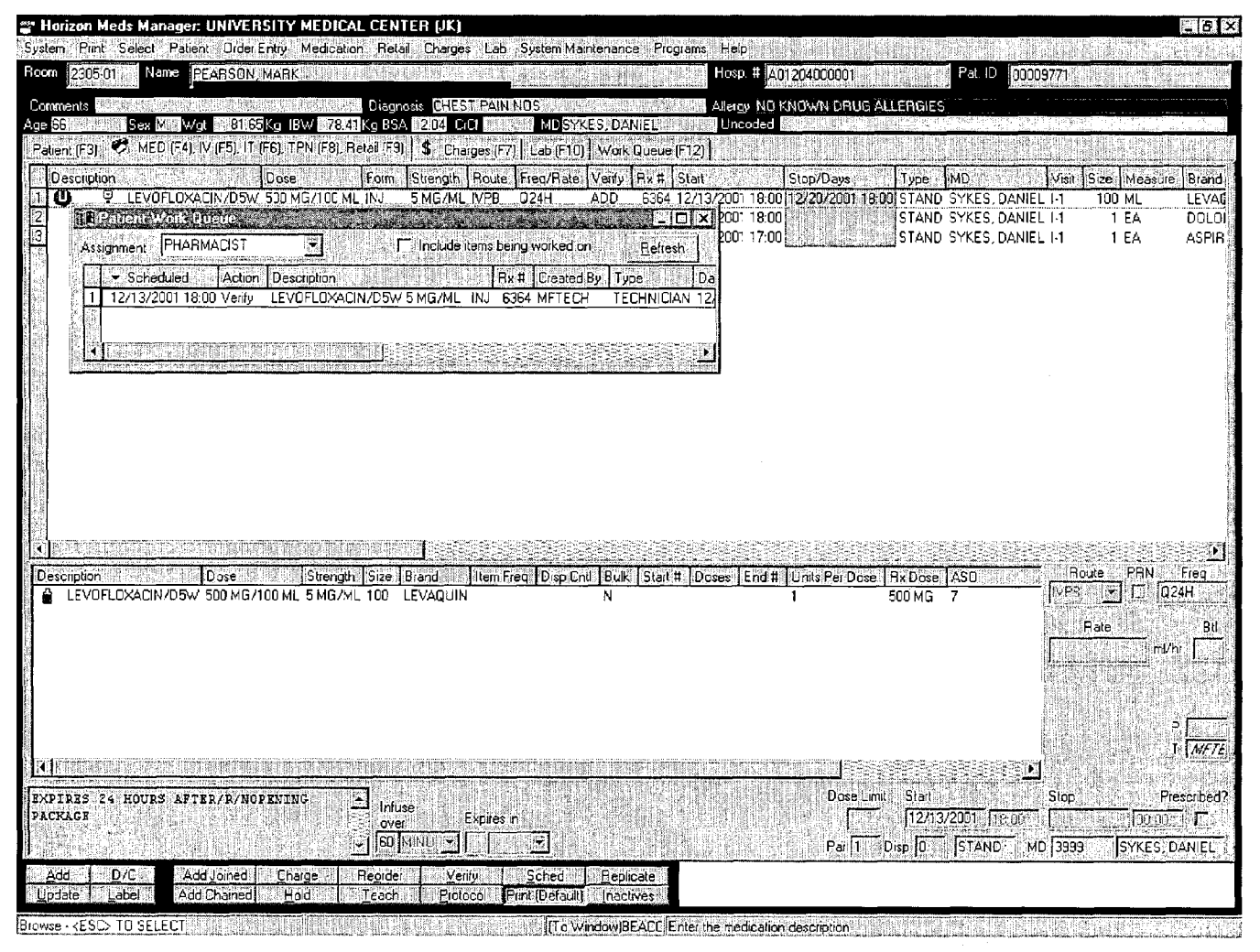
Figure 16:
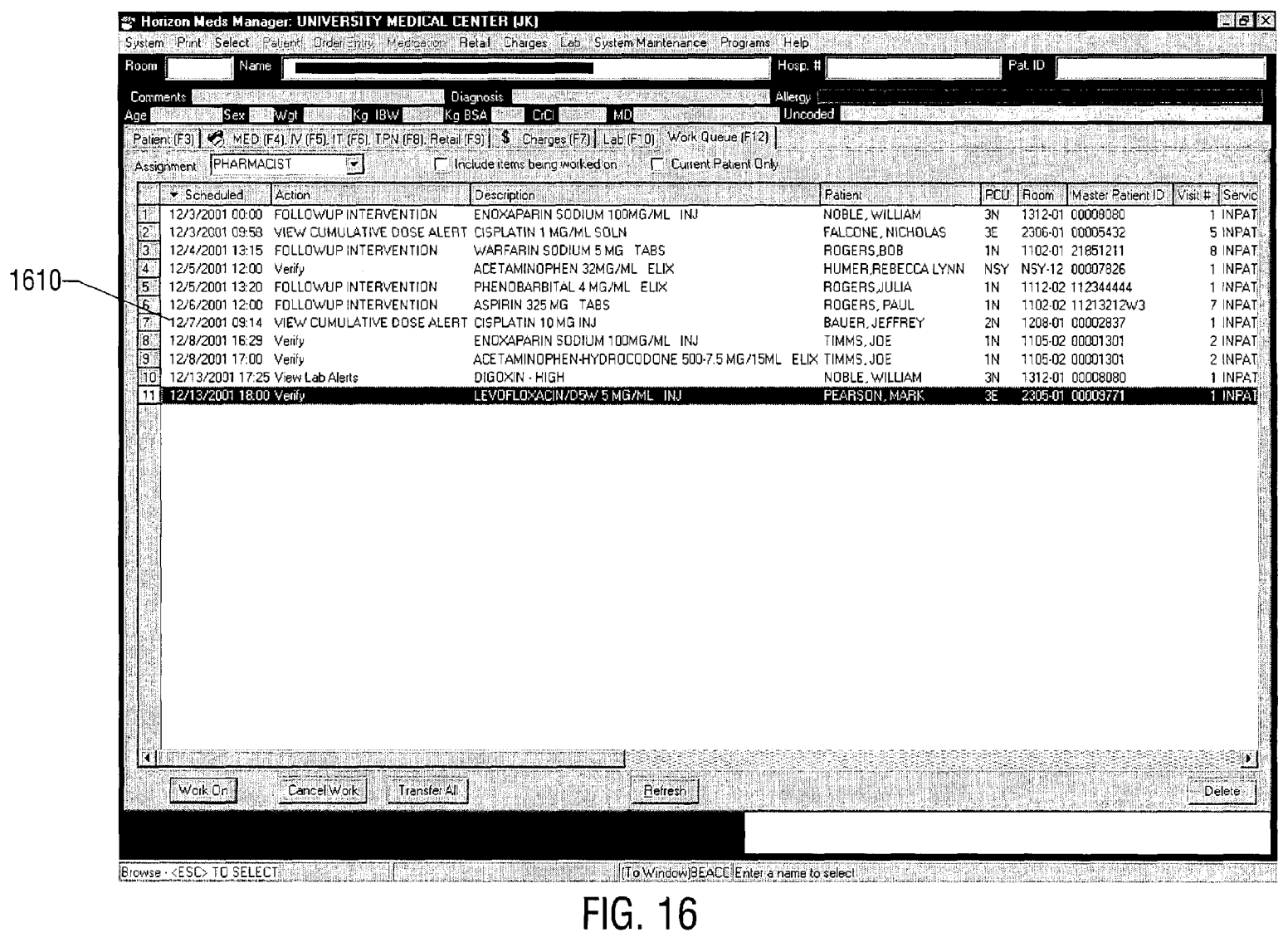

Turning now to FIG. 12, the operation of the transcribing system 200 is shown in FIGS. 12, 12A and 12B and the screen shots of FIGS. 13-16 for one embodiment of the invention. As shown in FIG. 12A, the pharmacist logs in to the system 213 and then selects an option 214 to either view completed orders 216 and their status or view pending orders 217. If the pharmacist chooses to view completed orders 216, an input 215 from the administering module 400 indicates to the pharmacist the status of previously verified orders. If the pharmacist chooses to view pending orders 217, a screen shot similar to FIG. 13 or 16 is displayed. As shown in FIG. 13 and also FIG. 16, each row of the pharmacist work queue includes a patient name 1310, the action that needs to be performed by the pharmacist 1320, and a description of the prescribed medication 1340. The transcribing module 200 generates and maintains a pharmacist work queue 218 that prioritizes the pharmacist tasks, based on pre-defined parameters and input 219 received from the prescribing module 100. In one embodiment of the invention, the pre-defined parameters can include prescription orders that need to be filled with highest priority (STAT) and can include prioritization based on the time the order was received from the prescribing module 100. A high priority medication order 1350 requiring the pharmacist to view laboratory alerts because of a high level of Creatinine ("Creatinine Clearance—HIGH") is shown in FIG. 13 for patient "Victor Seale."

Turning now to FIGS. 12, 12A, 12B and 16, the pharmacist work queue 218 is prioritized based on a scheduled task list. As shown in FIG. 16, the pharmacist work queue prioritizes the pharmacist activities based on the scheduled administration of the medication 1610, and scheduled follow-up medication interventions, and displays a prioritized list 220. The time indicated in the scheduled column 1610 of FIG. 16 can indicate the scheduled time for administration of the medication. In an alternative embodiment, the scheduled time 1610 can indicate the calculated time at which the pharmacist has to have the order verified to assure the dispensing and administration of the medication within a predetermined time period.

After the prioritized orders are displayed 220, the pharmacist selects an order 221. FIG. 16 illustrates the pharmacist's selection of line item 11 for patient "Mark Pearson". Once the pharmacist selects the order to be verified, as shown in FIGS. 14 and 15, a display 222 of relevant clinical information based upon communication from the patient information DB 20 and the medication information DB 30 is displayed. The information displayed assists the pharmacist in assessing and verifying the appropriateness of the physician prescription orders. Once the pharmacist reviews the prescription order, he or she can either verify the order as depicted in the screen shots shown in FIGS. 14 and 15, or enter comments and/or changes to the physician's prescription order as illustrated by decisional block 223.

If the pharmacist declines to verify the order, the pharmacist is requested to input any medication conflicts, comments and/or changes 224. The transcribing module 200 generates any alerts 225 input by the pharmacists and communicates the alerts in the form of feedback to the prescribing module 100. In one embodiment, the transcribing module 200 gives the pharmacist some leeway in the ability to change certain orders 228. If the requested change does not fall within the criterion allowing a pharmacist change in the order, the physician's order is placed on hold and an alert 229 is sent to the prescribing physician. If the requested change does fall within the criterion allowing a pharmacist change in the physician prescribed order, comments 229 are sent to the physician via the prescribing module 100 informing the physician of the prescription order change.

Once an order has been verified 223 or a change in the physician's prescription order accepted 228, the transcribing module 200 determines the dispensing method of the medication 227. The determination of the location that will dispense verified prescription orders is based on the patient's location in relation to the dispensing location and the availability of medication inventory at the various dispensing locations. The available medication inventory of the various dispensing locations is input to the transcribing module 200 from the dispensing module 300 as is indicated by input 226 in FIG. 12. After a dispensing location has been chosen, the pharmacist's verified order is transmitted 230 to dispensing module 300 as an input 231, the administering module 400 as an input 232, and the prescription order DB 40.

Figure 17:
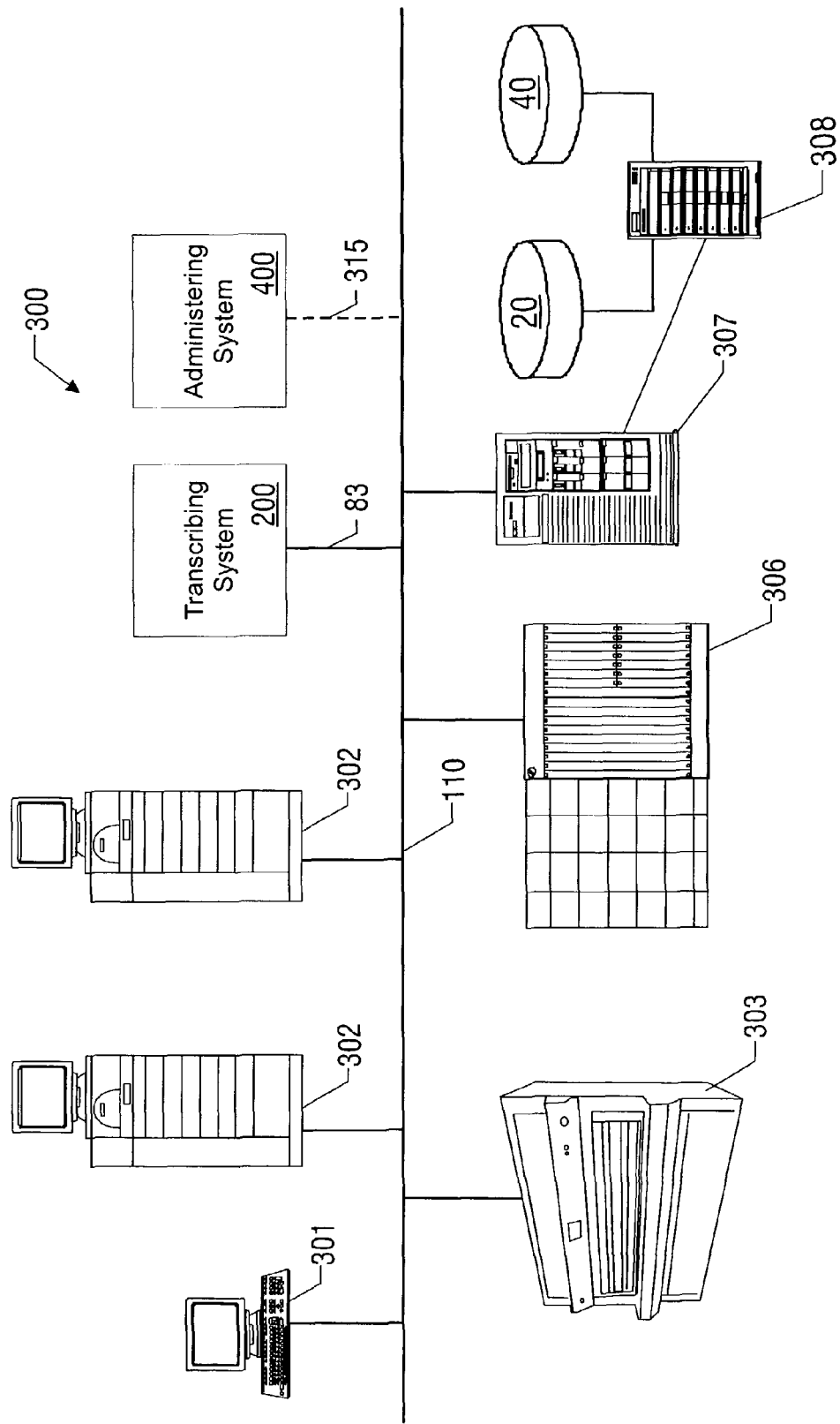
FIG. 17 shows an embodiment of the hardware interconnection of the dispensing portion of the closed loop medication use system.
Figure 19:
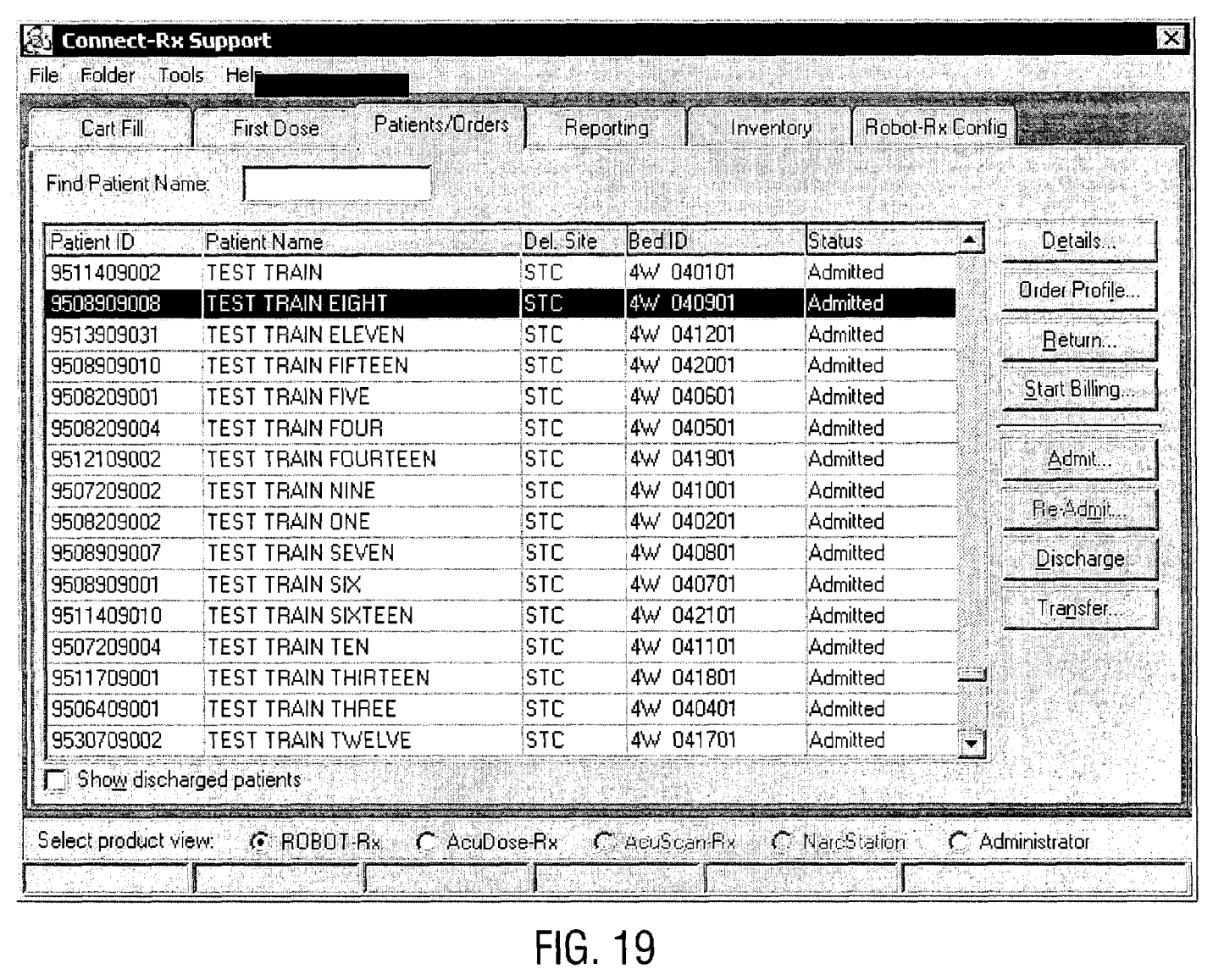
Figure 20:
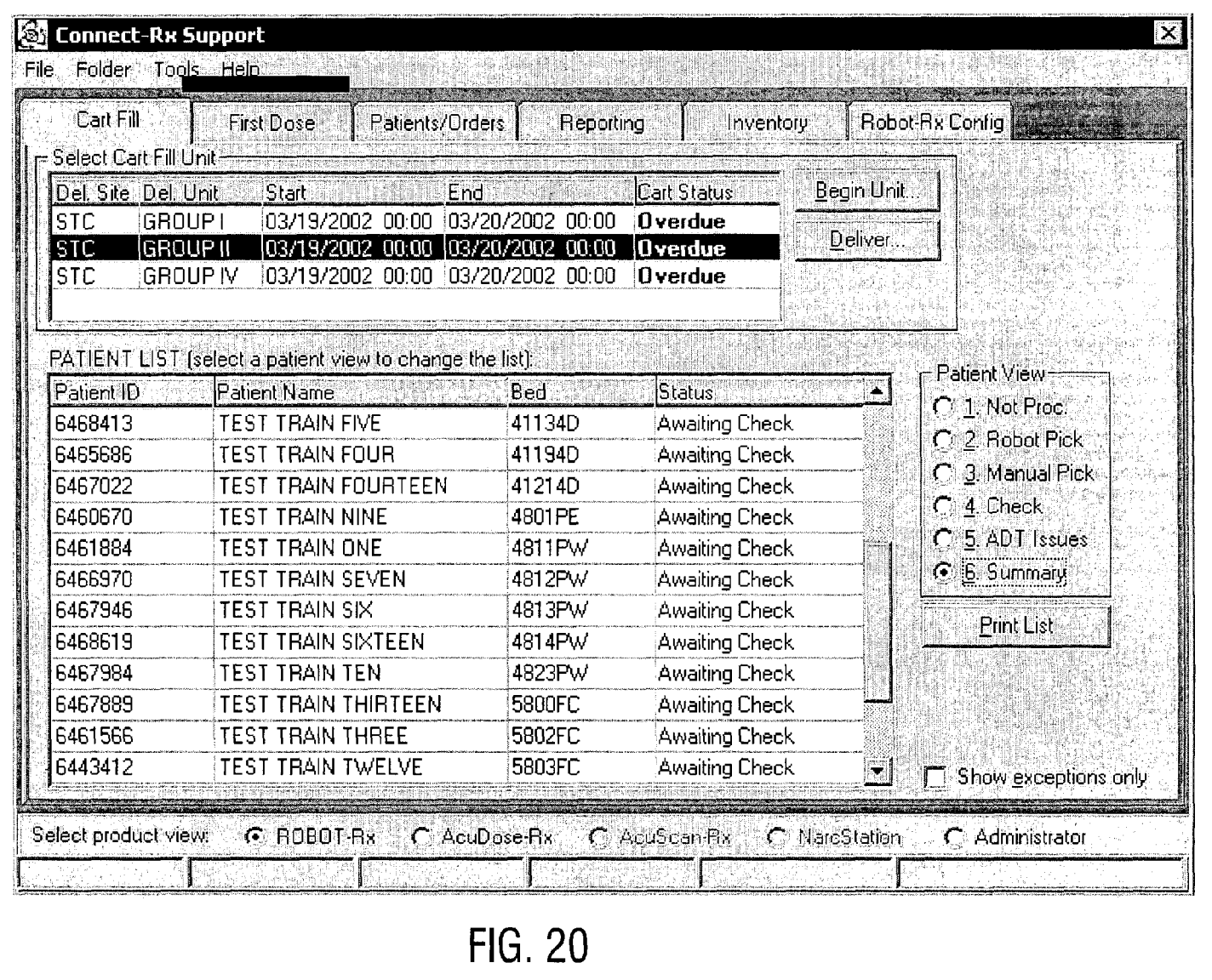
Figure 21:
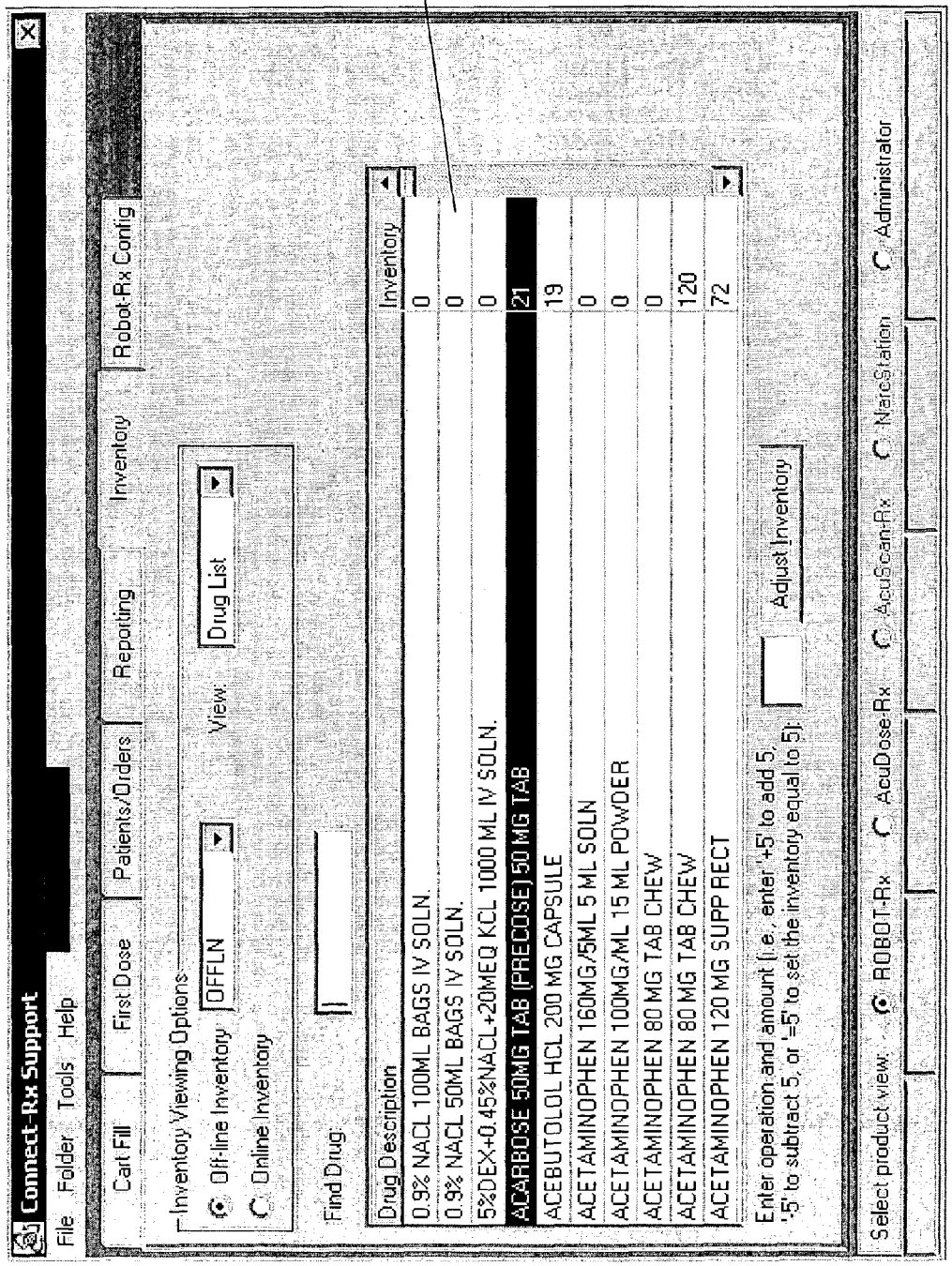
FIG. 21 shows a screen from the dispensing application that allows a pharmacy technician to view the available off-line inventory for the system.
Figure 22:
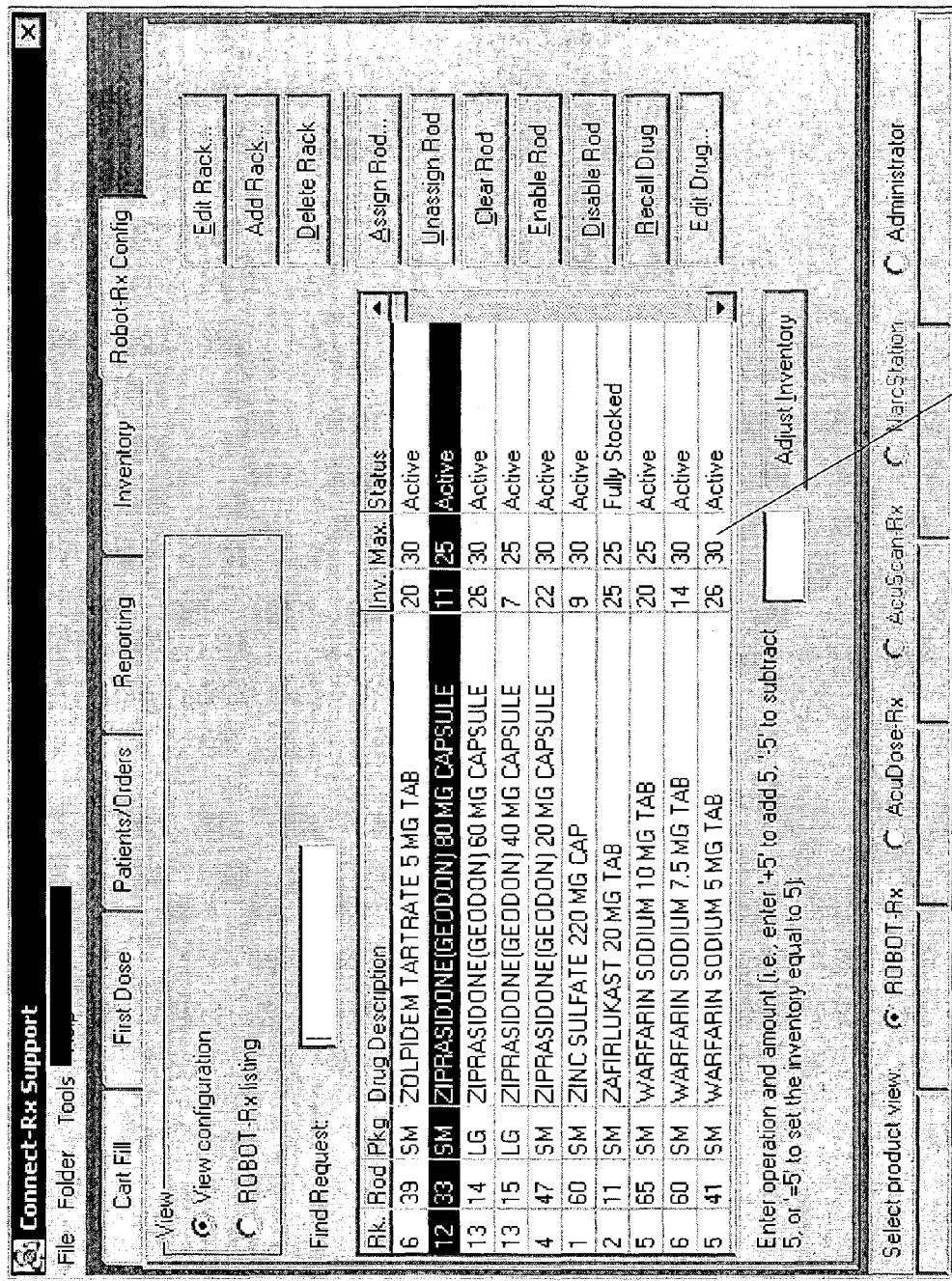
FIG. 22 shows a screen from the dispensing application that allows the pharmacy technician to view the system configuration and medication inventory status for the system.

Turning now to FIG. 17, hardware associated with the dispensing module 300 for one embodiment of the invention is shown. As part of the dispensing module, the medication is bar-coded and placed in a variety of unit-based medication dispensing cabinets ("UBCs") 302 located at different points around the patient-care site. In another embodiment, the medication is packaged, bar-coded and dispensed using a robotic medication dispenser 306. In still another embodiment, the medication is packaged, bar-coded and dispensed from an automated storage and retrieval device 303 product, which dispenses bar-coded product through the use of pick-to-light technology for use in both fulfilling patient orders received from the transcribing portion, as well as processing replenishment orders for medication dispensing cabinets and remote pharmacy locations. The bar-coded medicine is identified by type and medication dosage. The bar-coded packets can be supplied via the use of specialized packaging systems, which provide unit-dose packaging and bar coding of medication. FIGS. 19 through 22 illustrate various screen shots from a specialized packaging system. For example, FIGS. 19 and 20 depict patient information and location. Also, FIGS. 21 and 22 are screen shots that show the specialized packaging system's offline inventory and configuration.

Additional packaging and bar coding systems can be utilized. For instance, a general disclosure of packaging systems implementing bar coding is provided in U.S. Pat. No. 6,289,656 issued on Sep. 18, 2001 and U.S. Pat. No. 6,497,342 issued on Dec. 24, 2002, both of which are incorporated by reference herein in their entireties.

The UBCs 302, robotic medication dispenser 306, and the automated storage and retrieval device 303 are all connected to the patient-care site's LAN 110. The dispensing module 300 receives notification of verified prescription orders from the transcribing module 200 via communication interface 83. The dispensing module 300 also includes a dispensing application server 307 that receives information from the prescription order DB 40 and the patient information DB 20, through dispensing DB server 308.

Figure 18A:
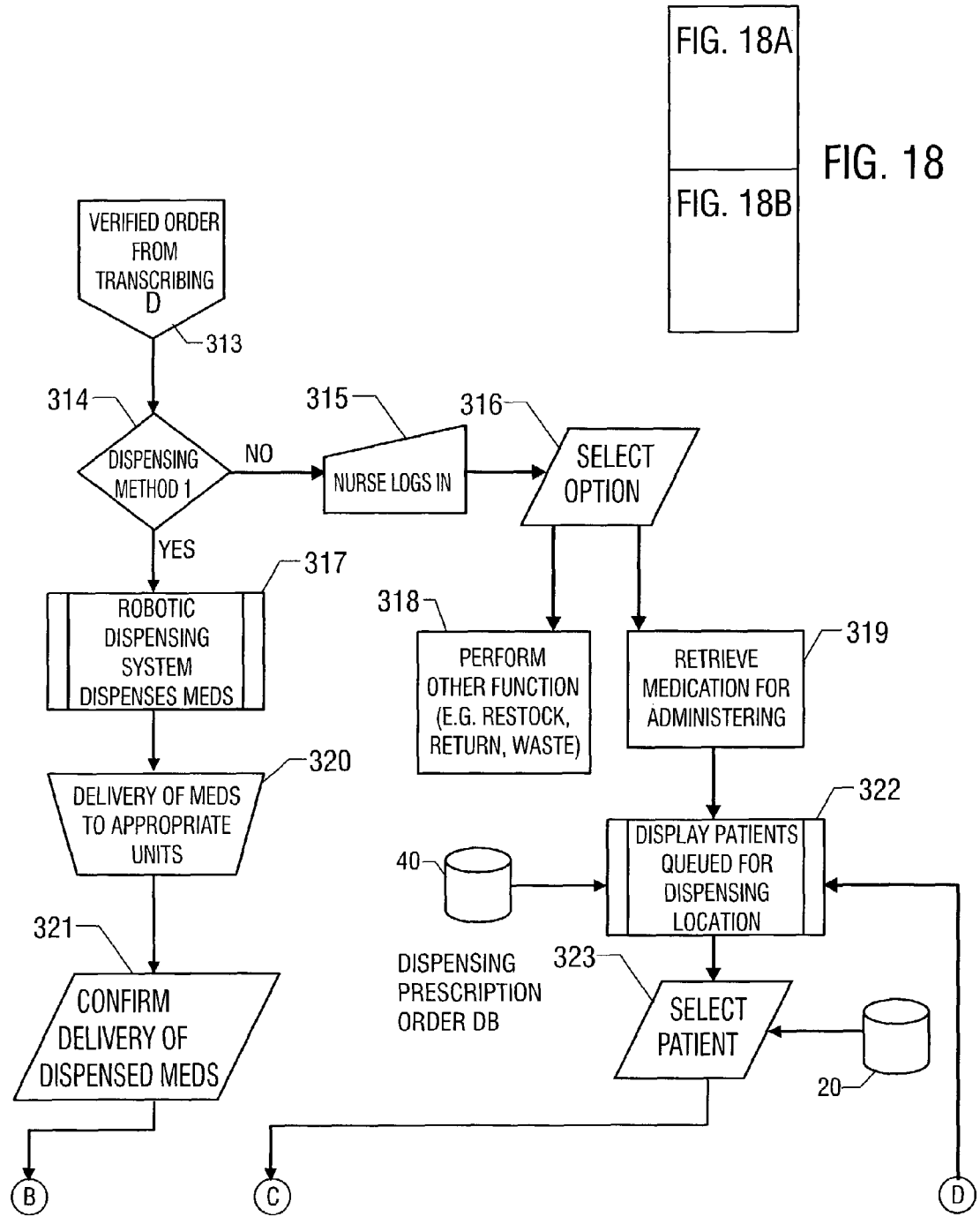
Figure 18B:
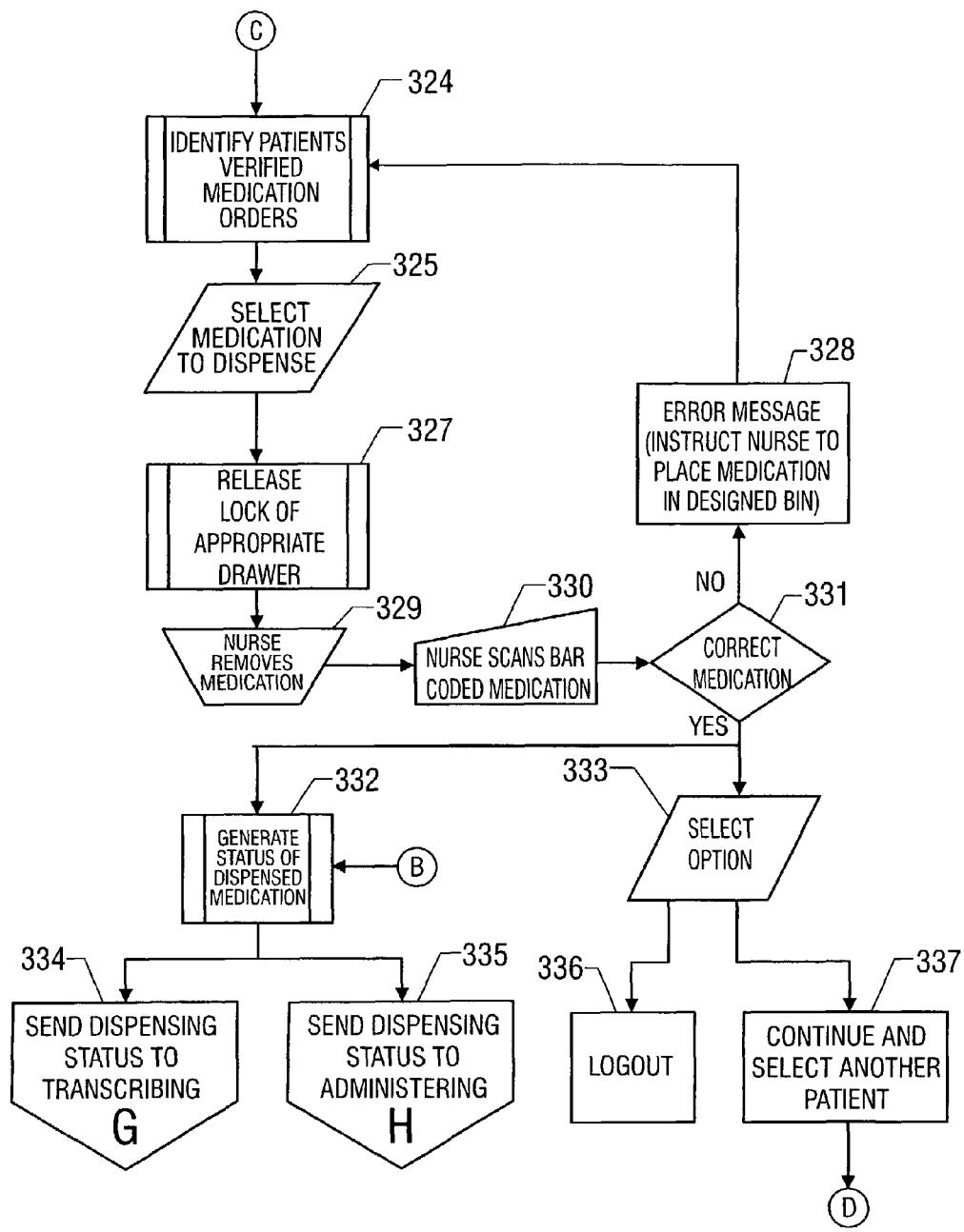

Referring to FIGS. 18, 18A and 18B, and to FIG. 17, in one embodiment, based on the verified prescription orders received from the transcribing module 200 as shown by step 313 and the dispensing method 314, the robotic medication dispenser 306 pulls all of the medication to be administered for a specific patient and dispenses the medications 317. The medications are then delivered 320 to the appropriate nursing unit. The robotic medication dispenser 306 and the automated storage and retrieval device 303 are capable of arranging for delivery of the medication to the appropriate nursing unit. The nurse confirms receipt of the medications 321 and a status update of the dispensed medication is generated 332 and communicated to the transcribing module 200 and administering module 400, as shown in steps 334 and 335, respectively.

In another embodiment of the invention, the administering nurse logs into the patient-care site's LAN 110 using a nurse station terminal 301 in order to view administering tasks. Based on the nurse's administering tasks, the nurse proceeds to the appropriate UBC 302 locations indicated in his or her task list. Once at the UBC 302 locations, the nurse logs into 315 the dispensing module 300. Various UBC 302 functions 318 (e.g. Dispense, Restock, Return, Waste) may be available to the nurse depending on specific access and security settings determined by the system administrator. After successfully logging into 315 the UBC 302, the nurse can select whether to perform specified functions 318, or the nurse can select to retrieve medication 319, which presents the nurse 322 with a list of patients for whom medications may be removed from the UBC 302 based on an input from the prescription order DB 40 and the patient information DB 20. By default, the nurse is presented with the "Dispense" screen, which permits medications to be removed from the UBC 302.

The nurse then selects a patient 323 and the dispensing module 300 identifies the patient's verified prescription orders 324. In step 325 the nurse selects a medication to dispense and enters a dispense quantity. The dispensing module 300 releases the lock of the appropriate UBC drawer 327, and the nurse removes the medication 329.

The dispensing module then prompts the nurse to scan the bar codes selected medication 330. If the nurse has selected the correct medication 331 based on the bar code, the status of dispensed medication is sent to the transcribing 200 and administering 400 modules, as depicted by output steps 334 and 335, respectively. In addition, if the nurse has selected the correct medication 331, the nurse is then prompted to either logout of the system 336 or continue to dispense medication 337. If the scanned medication's bar code is not correct, an error message is generated, that instructs the nurse to place the incorrect medication in a designated bin 328, and allows the nurse to attempt to retrieve the correct medication. After a predetermined number of incorrect medication retrievals, the system can be configured to lock the nurse out of the dispensing system and instruct the nurse to contact the appropriate personnel.

Figure 23:
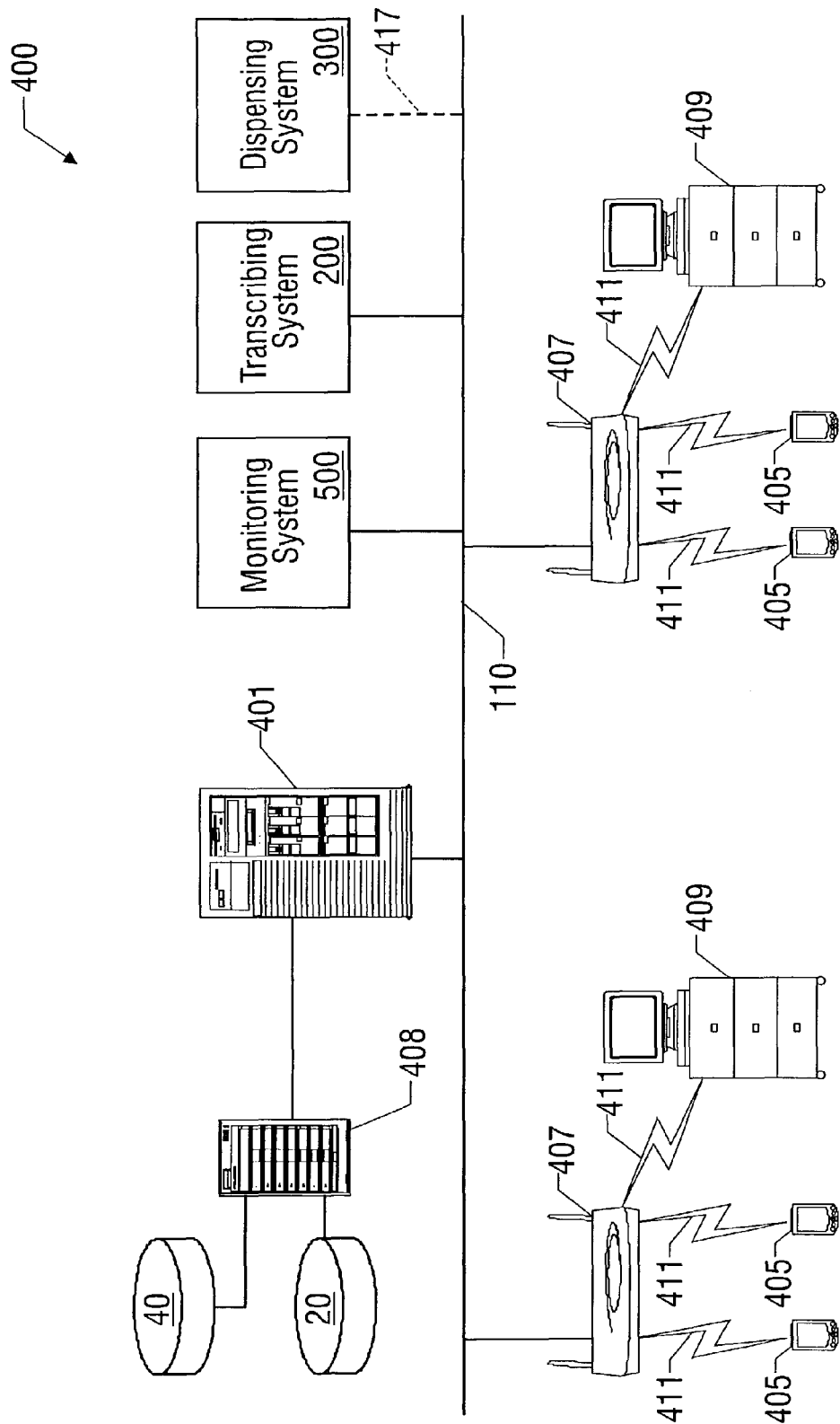
FIG. 23 shows an embodiment of the hardware interconnection of the administering portion of the closed loop medication use system.

Turning now to FIG. 23, hardware associated with the administering module 400 for an embodiment of the invention is shown. In one embodiment, once the medication has been physically dispensed 79 as shown in FIG. 1, the transcribing module 200 and dispensing module 300 communicate over LAN 110 to the administering module 400 the medication to be administered. In an alternative embodiment as shown in FIG. 23, after the medication has been dispensed, the dispensing module 300 transmits through communication interface 417 over LAN 110 to administering module 400 the medication to be administered. The administering module 400 is connected to the patient-care site's LAN 110, and includes administering application server 401 and administering database server 408. These servers receive data from and transmit data to the patient information DB 20 and/or to the prescription order DB 40.

As shown in FIG. 23, an administering nurse may use a computer device with a scanner, such as a laptop with wireless communication cards, mounted to a rolling medication cart 409 or wireless bar code scanner 405 that communicate through communication links 411 to wireless access points 407. The wireless access points are connected to the patient-care site's LAN 110. In an alternative embodiment of the invention, wireless access points 407 in FIG. 23, 107 in FIG. 3, and 207 in FIG. 11 connected to proper peripheral devices may interchangeably be used by prescribing physicians, transcribing pharmacists, and administering nurses.

Figure 24B:
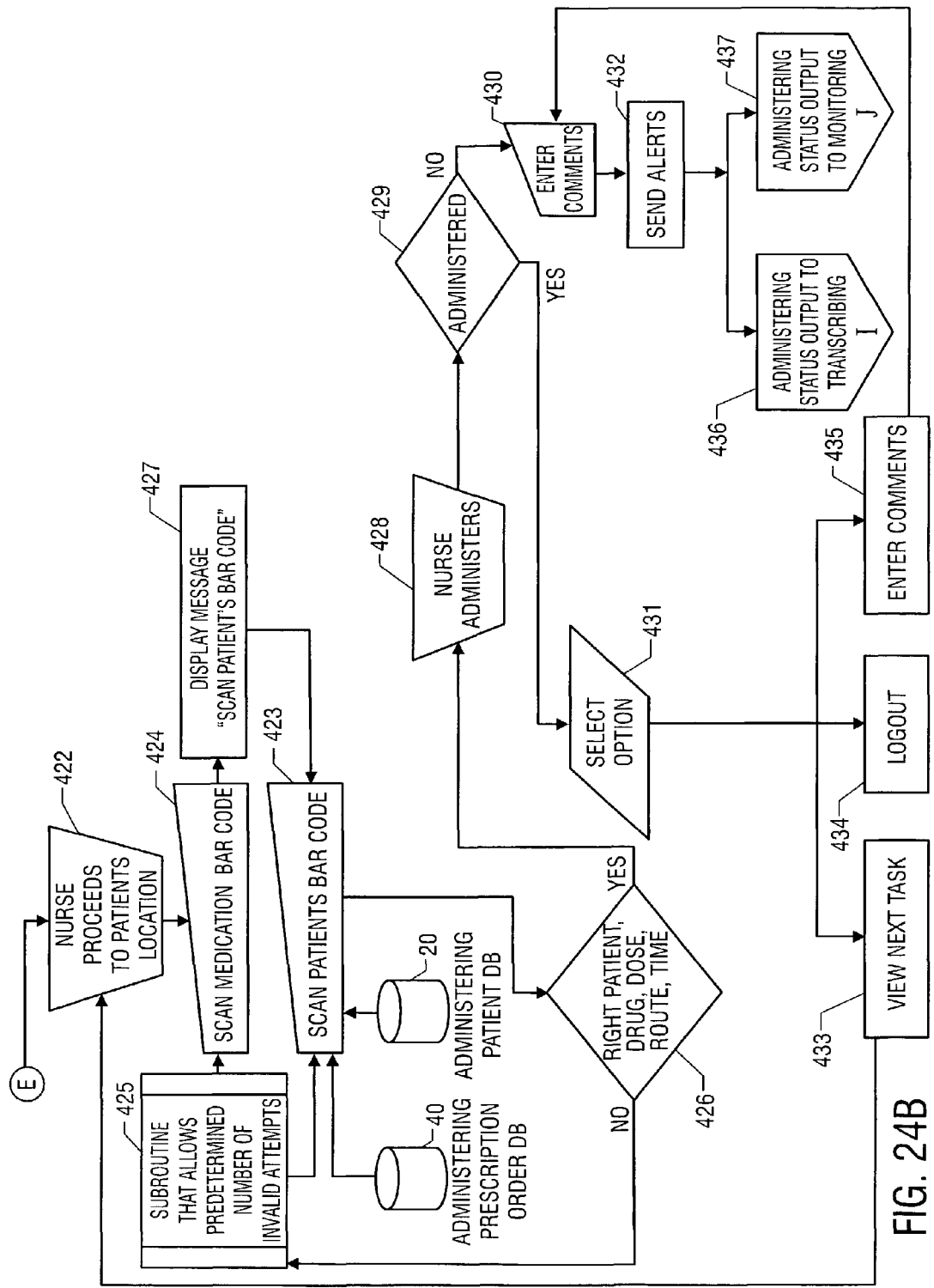
Figures 25, 26:
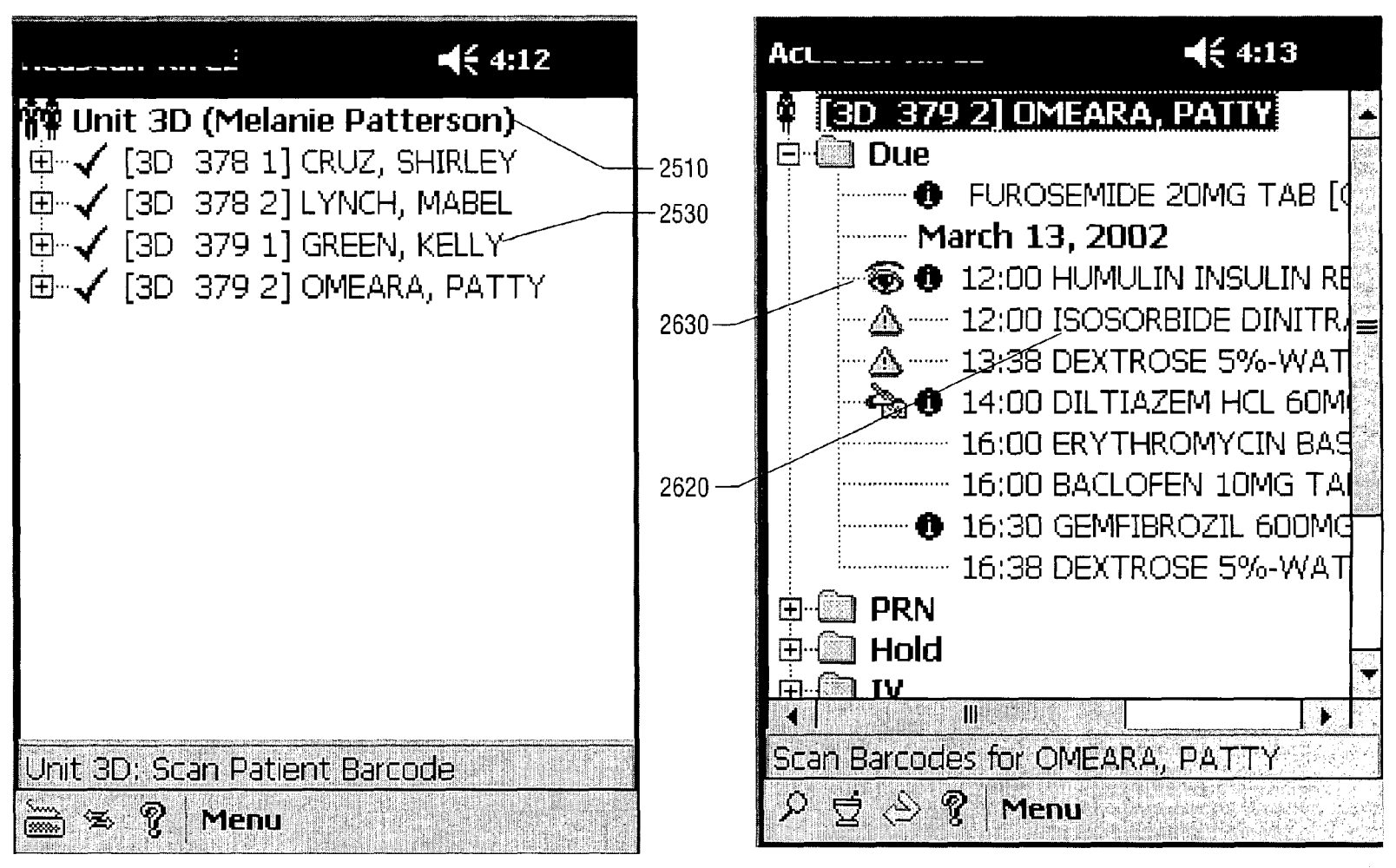

Turning now to FIGS. 24, 24A and 24B, the operation of the administering module 400 for an embodiment of the invention is shown. The operation of the administering module 400 is also illustrated by the screens shots shown in FIGS. 25-31. Transcribing module 200 and dispensing module 300 transmit information to administering module 400 through inputs 416 and 418 respectively as shown in FIG. 24A. In step 417, the transcribing and dispensing module identify to the administering module the medication to be administered and the status of verified orders and dispensed medications. Next, in step 419, the nurse selects whether to use wireless scanner 405 or mobile laptop 409 as shown in FIG. 23. Assuming the nurse decides to use wireless scanner 405, in step 420, the nurse logs in to the system, the scanner 405 displays the nurses census 421 as depicted in the screen shot shown in FIG. 25. In FIG. 25, the administering nurse is "Melanie Patterson" 2510 and she is a member of hospital unit 3D. The scanner 405 displays a list of patients 2530 assigned to "Melanie Patterson", the list includes patients "Shirley Cruz" in room 378, bed 1, and "Patty Omeara", located in room 379, bed 2.

In one embodiment, the nurse then selects a patient, and a display as shown in FIG. 26 listing the administration time, type of medication, and dosage for the medication to be administered to the patient 2620. In one embodiment of the invention, symbols to represent medication alerts (e.g. requiring comments upon administration, requiring a witness upon administration, or requiring the use of extreme caution when administering) are indicated 2630 next to the corresponding medication. For example, the nurse has chosen to administer 4 units of humulin insulin regular type, which as shown in FIG. 26 requires a witness, indicated by using an eye symbol 2630.

Figure 30:
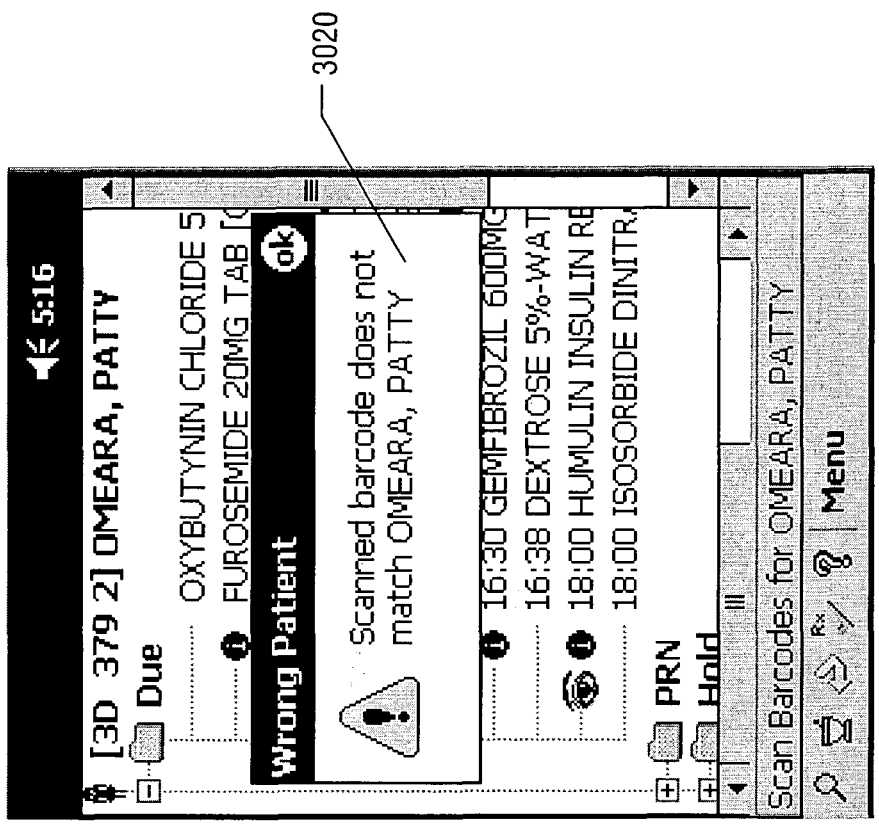
FIG. 30 shows a screen shot from a wireless scanner display warning the nurse administrator that the medication bar code scanned is not for this patient.
Figure 29:
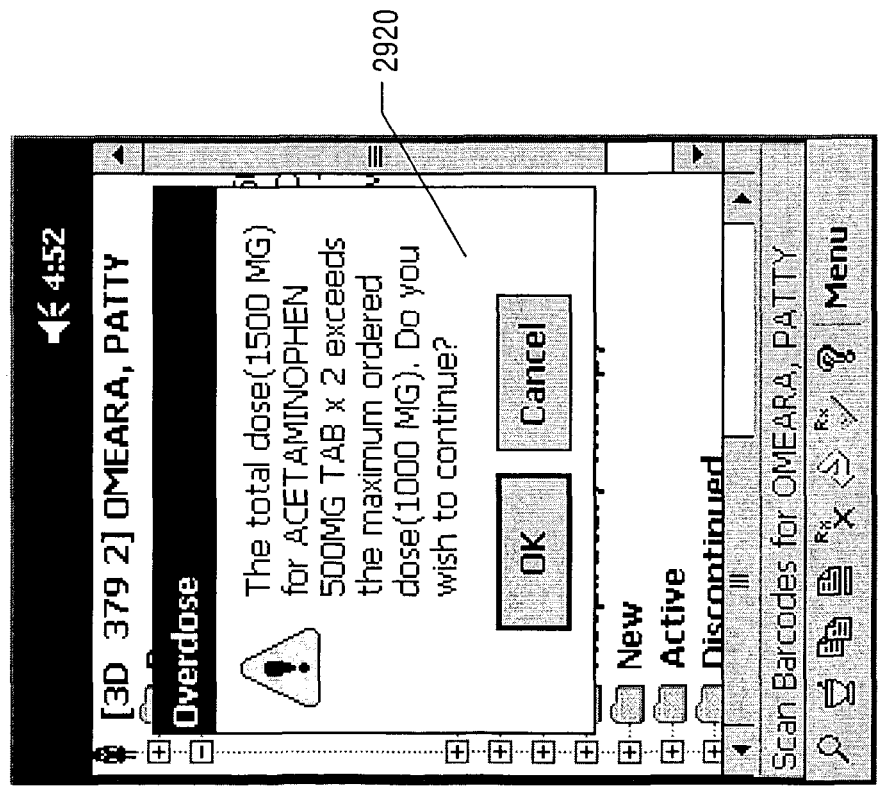
FIG. 29 shows a screen shot from a wireless scanner display of a potential medication overdose warning to the nurse administrator after he scans the medication bar code.

Returning now to FIG. 24B, the nurse first scans the medications to be administered to the patient 424. Alternatively, medications may be selected from a list of medications received from the medication information DB 30. In one embodiment of the invention, based on information received from the patient information DB 20 and the prescription order DB 40, the administering module 400, determines if the "five rights" of medication administration have been satisfied 426, the right patient, right medication, right dose, right route and right time. If any of the "five rights" have not been satisfied, a subroutine 425 provides an error message, such as a warning of a potential medication overdose 2920, as depicted in FIG. 29, or a warning that the scanned bar code is not the correct patient 3020, as depicted in FIG. 30. The subroutine 425 allows the administering nurse to correct the inaccuracy. In one embodiment of the invention, the administering module 400 can be configured to provide as few or as many attempts to correctly administer the medication, per the user's guidelines.

Figure 28:
FIG. 28 shows a nurse administrator scanning the patient's bar code.
Figure 27:
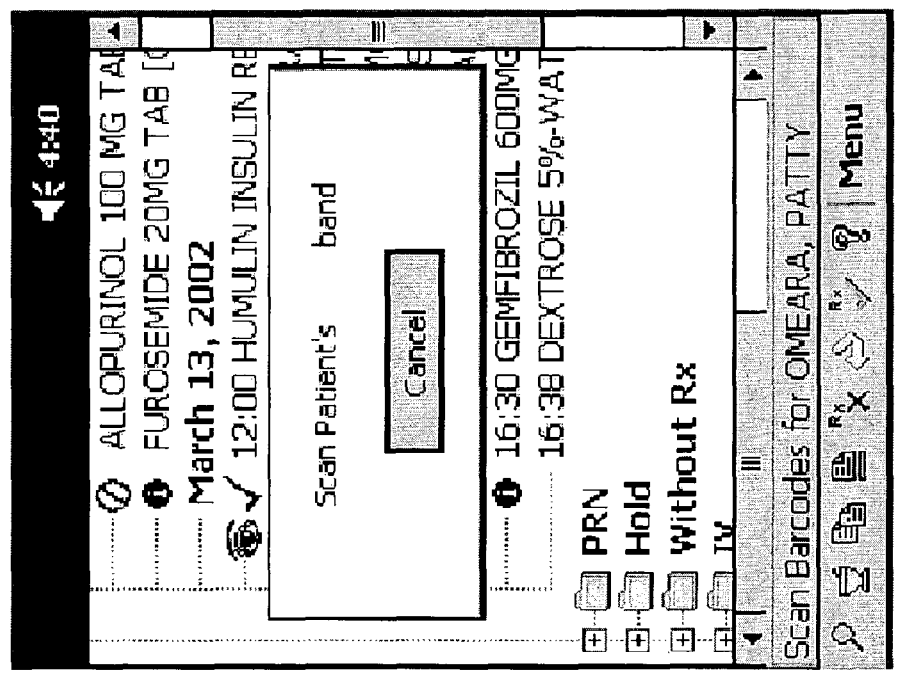
FIG. 27 shows a screen shot from a wireless scanner display that prompts the nurse administrator to scan the patient's bar-coded band.
Figure 31:
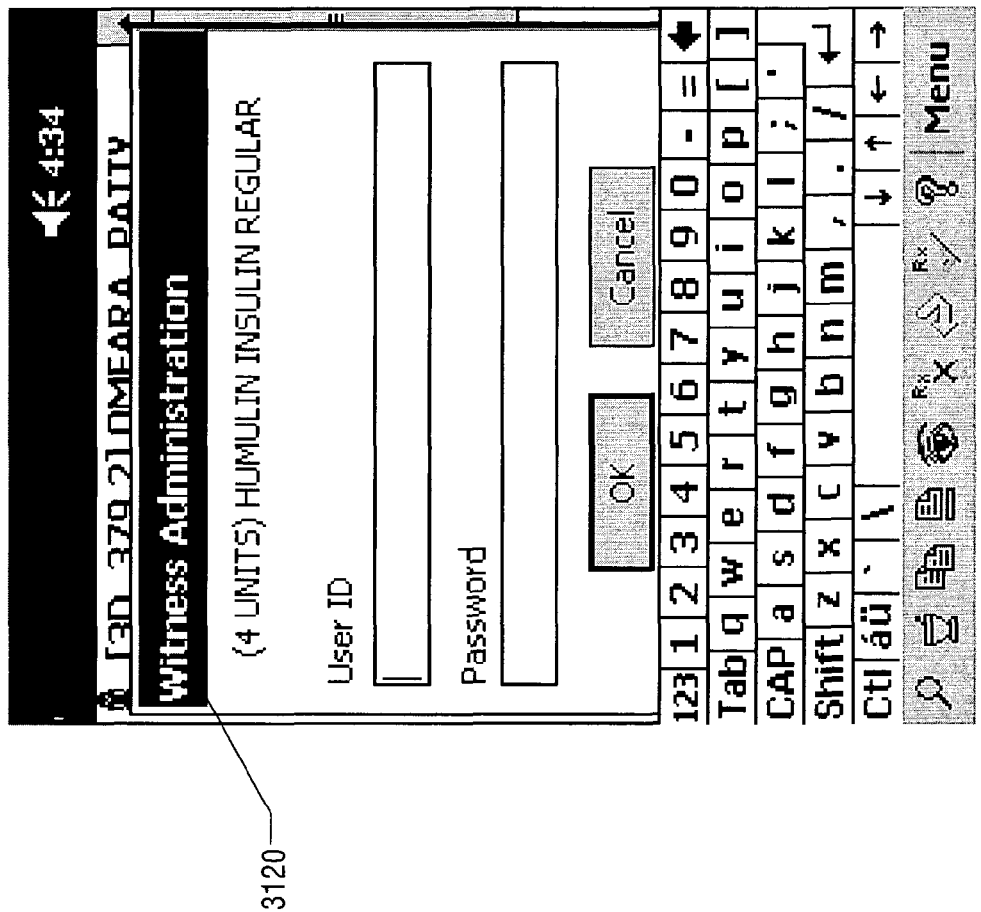
FIG. 31 shows prior to administration of a medication that requires a witness, a wireless scanner display screen shot asking for a witness administrator to enter his user id and password.

If the "five rights" have been satisfied, any warnings, cautions, or alerts are displayed to the administering nurse. For example, referring back to FIG. 26, the administration of 4 units of humulin insulin regular type, triggers the requirement of a witness prior to the administration 3120, as depicted in FIG. 31. In this instance, once the witness enters his/her user ID and password, a message is displayed indicating to scan the patient's wristband 427 as indicated in FIG. 24B. Next, the nurse scans the patient's bar coded wristband 423 for example as illustrated in FIG. 28. The patient may also be identified to the administering clinician by an electronic chip, integrated circuit, or other unique identifier. A determination 426 of the "five rights" is performed, and if any have not been satisfied, a subroutine 425 alerts the nurse and allows the nurse to correct the inaccuracies.

If the five rights have been satisfied, in step 428, the nurse proceeds to administer the medication. In one embodiment, the system then prompts the nurse to indicate if the medication has been administered 429. If the medication has not been administered, the nurse is prompted to enter comments 430. After the comments are entered, as shown in FIG. 24B, alerts 432 are sent to the transcribing module 200 and monitoring module 500 by outputs 436 and 437 respectively. In one embodiment of the invention, from the transcribing and monitoring modules, the alerts are relayed to the prescribing module 100, in order to alert the physician of the administering comments. If the medication has been administered, the nurse is prompted to select the option of viewing the next administering task 433, logging out of the system 434, or entering comments 435. If the nurse chooses to enter comments 435, the comments are entered 430 and alerts 432 are sent to the transcribing 100 and monitoring 500 modules for the physician's, pharmacist's, or other clinician's review.

In another embodiment of the invention, after the nurse selects a patient, the nurse may select a medication to administer to the patient that has not yet been electronically ordered (i.e. gone through the steps of Prescribing, Transcribing, and Dispensing). Thus, input 95 to the Administering module, as shown in FIG. 1, permits the nurse to administer a medication ordered non-electronically (i.e. paper-based) and record this administering event. Situations in which administering of medicines without going through the Prescribing, Transcribing and Dispensing steps include emergency administrations by the doctor or nurse because of unpredicted deterioration in patient condition and if the CLMUSM is temporarily inaccessible because of hardware or software failures.

Figure 32:
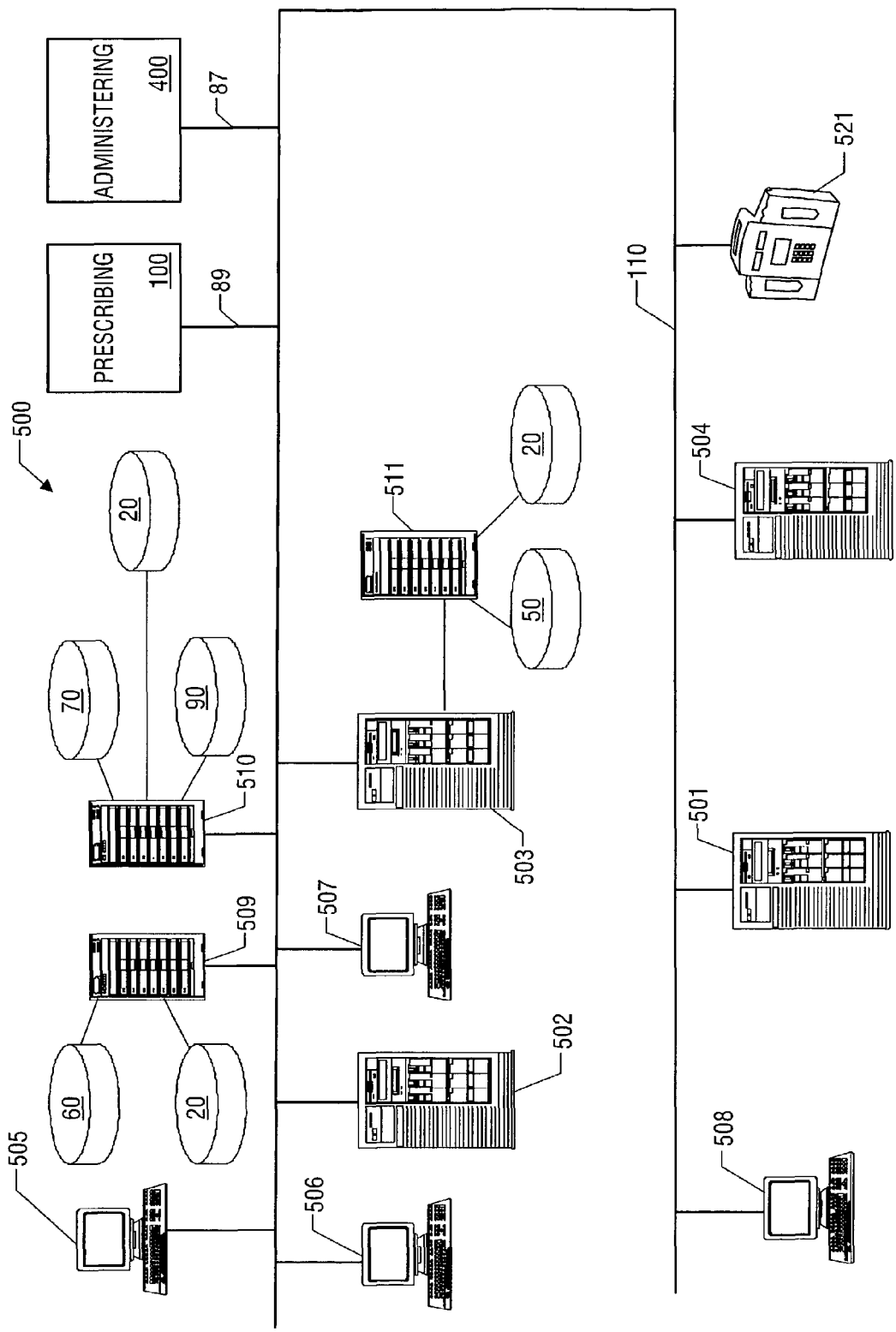
FIG. 32 shows an embodiment of the hardware interconnection of the monitoring portion of the closed loop medication use system.

Turning now to FIG. 32, this figure shows one embodiment of a monitoring module 500 connected to the patient-care site's LAN 110. In the CLMUSM, the monitoring module 500 continuously monitors the patient's condition and reaction to administered medication. In one embodiment, an expert system rules-based decision support system continually monitors patient data to inform the clinician at any point in the CLMUSM, when the patients condition and pending orders, prescriptions, and laboratory tests should be altered, re-examined, or even cancelled. Other embodiments for implementation of the decision support system may include any heuristic artificial intelligence system capable of continually monitoring patient data and making decisional conclusions to inform the clinician of patient condition and other critical data.

As shown in FIG. 32, the monitoring module 500 includes a monitoring application server 501 and a patient-care site's application server 502, a laboratory application server 503, and a radiology application server 504 connected to the LAN 110. As shown, radiology DB server 509 is also connected to the LAN 110, and receives data from radiology DB 60 and patient information DB 20. Patient-care site DB server 510 is connected to the LAN 110, and receives data from a patient-care site's clinical standard of care DB 70, a patient-care site cost factor DB input 90, and patient information DB 20. Laboratory DB server 511 is connected to the LAN 110 via laboratory application server 503, and receives data from laboratory DB 50 and patient information DB 20. For illustrative purposes, radiology terminal 505, laboratory terminal 506, emergency room terminal 507, and patients records terminal 508 are all shown connected the LAN 110.

Figure 33:
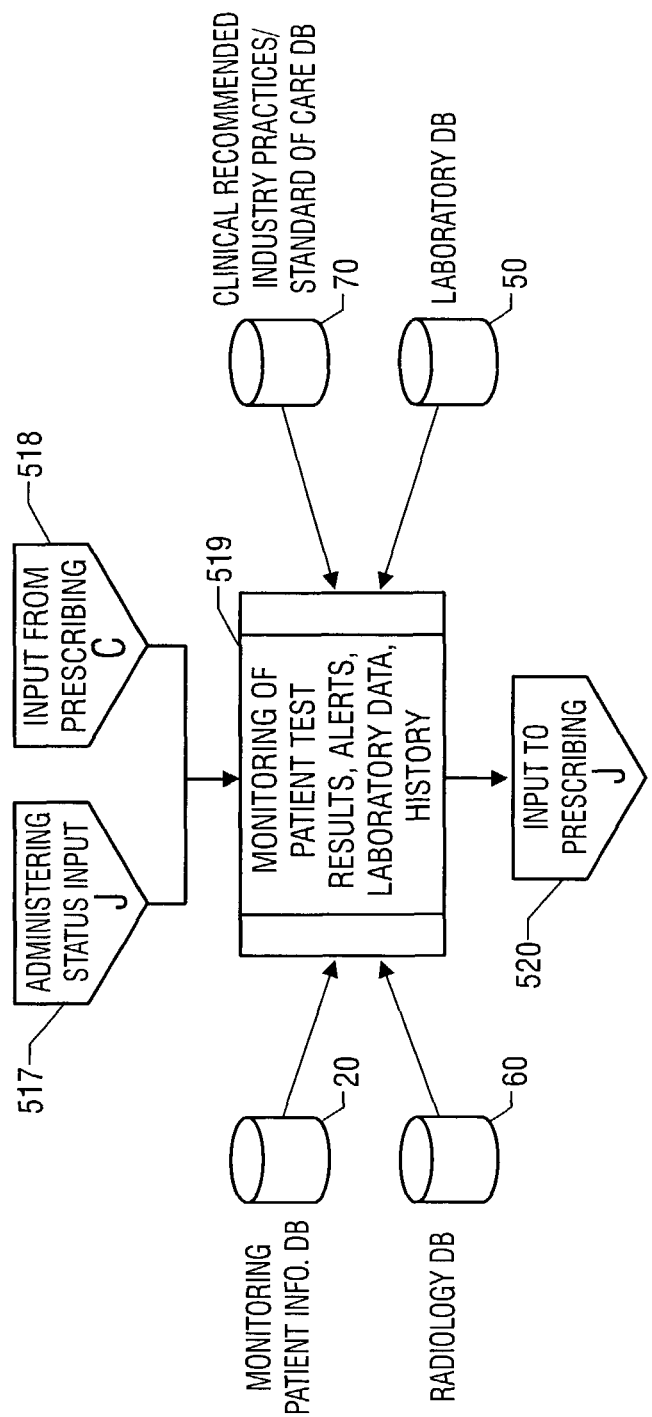
FIG. 33 is a flow diagram of the monitoring portion of the closed loop medication use method showing continuous monitoring and evaluation of patient medical data.

The monitoring module 500 as shown in FIG. 32 receives and sends information to the prescribing module 100 through communication interface 89. As shown in FIG. 33, the information sent to the prescribing module 100 through output 520 includes laboratory results, radiology results, dispensing and administration information, current hospital standard of care procedures and costs of medications or other treatment and alerts. In alternative embodiments, these alerts can be communicated to the physician through mobile messaging, so that the physician is kept up to date about critical changes or alerts regarding their patients. The information received from the prescribing module 100 is received at input 518 in FIG. 33. As shown in FIGS. 32 and 33, the monitoring module includes a radiology DB input 60, a laboratory DB input 50, a patient information DB input 20, a patient-care site's clinical standard of care DB input 70, and a patient-care site cost factor DB input 90, that are all connected to the patient-care site network 110 via their respective database or application servers. Other embodiments of the invention may include the information stored on each of the databases 20, 50, 60, 70, and 90 shown in FIGS. 2 and 2A combined into one database located on a hardware storage medium such as a disk array. Another embodiment may include the database information stored together in any combination of databases (i.e. radiology DB 60 and laboratory DB 50 combination, patient information DB 20 and patient-care site cost factor DB 90 combination), each combination located on a separate hardware storage medium.

As shown in FIG. 32, the monitoring module 500 also receives information from the administering module 400 through communication interface 87 (input 517 in FIG. 33), regarding the status of administered medication, and any alerts or comments made by the administering nurse. In still another aspect of the present invention, the monitoring module 500 includes the monitoring of a patient's IV infusion. In this aspect, a smart intravenous ("IV") fluid infusion pump 521, utilizes Ethernet, and/or wireless communication technology to connect to the LAN 110 and communicates information, such as the amount of IV fluid administered to a given patient at specific times, thereby updating the patient info DB 20 and providing any associated alerts. Hence using the CLMUSM, both the administering module 400 and monitoring module 500 are updated with patient IV use information. For a general disclosure of an infusion pump capable of communicating with the a network on a continuous basis in order to provide data on the amount of fluid that has been administered to a patient via IV, see U.S. Non-Provisional patent application Ser. No. 09/860,865, Pub. No. US 2001/0044731 filed on May 18, 2001, entitled "Distributed Remote Asset and Medication Management Drug Delivery System," which is incorporated by reference herein in its entirety.

Figure 34:
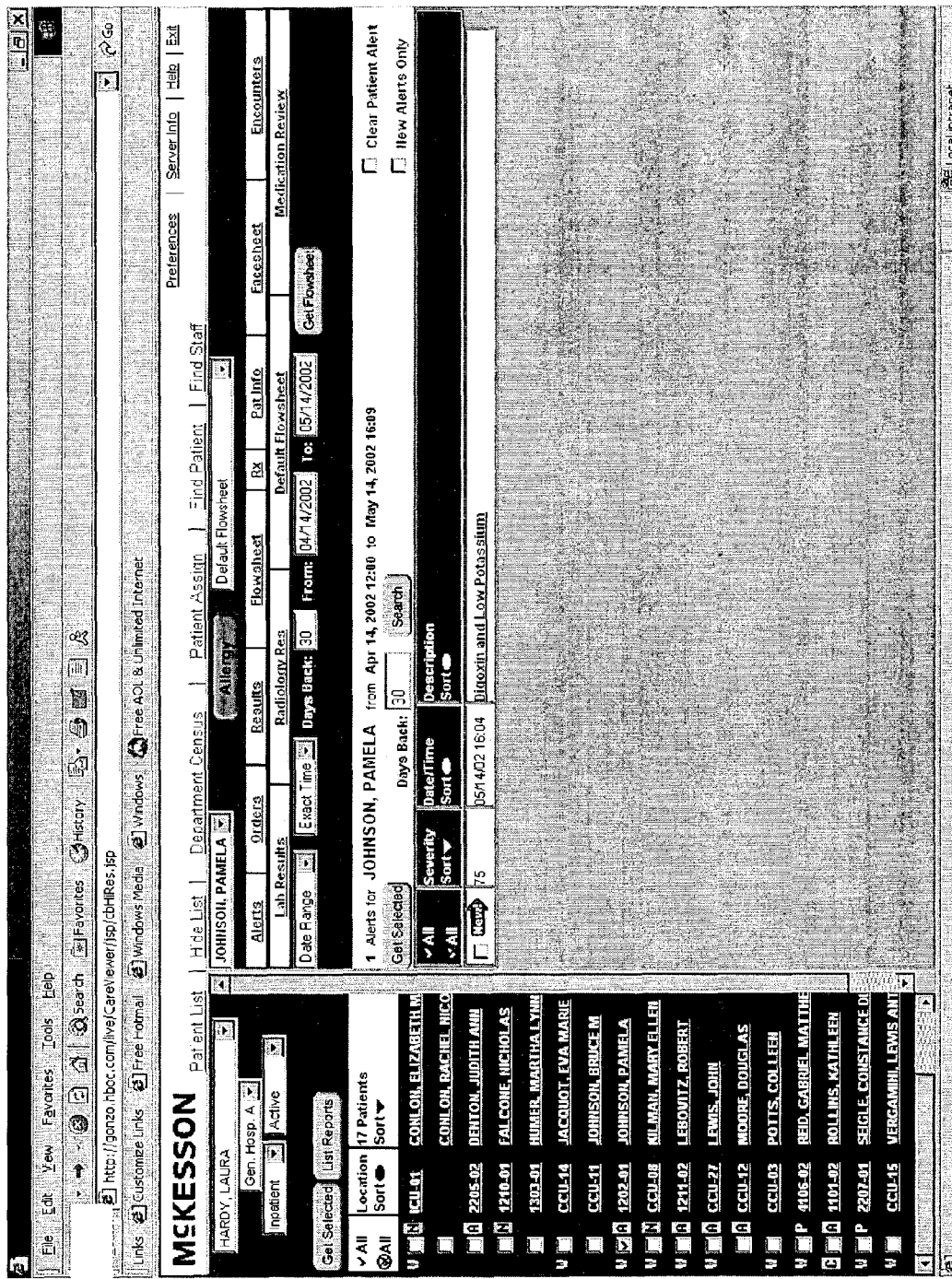
FIG. 34 shows a screen shot generated by the monitoring application that displays using a WWW physician portal a variety of real-time patient information to alert a clinician or physician.
Figure 35:
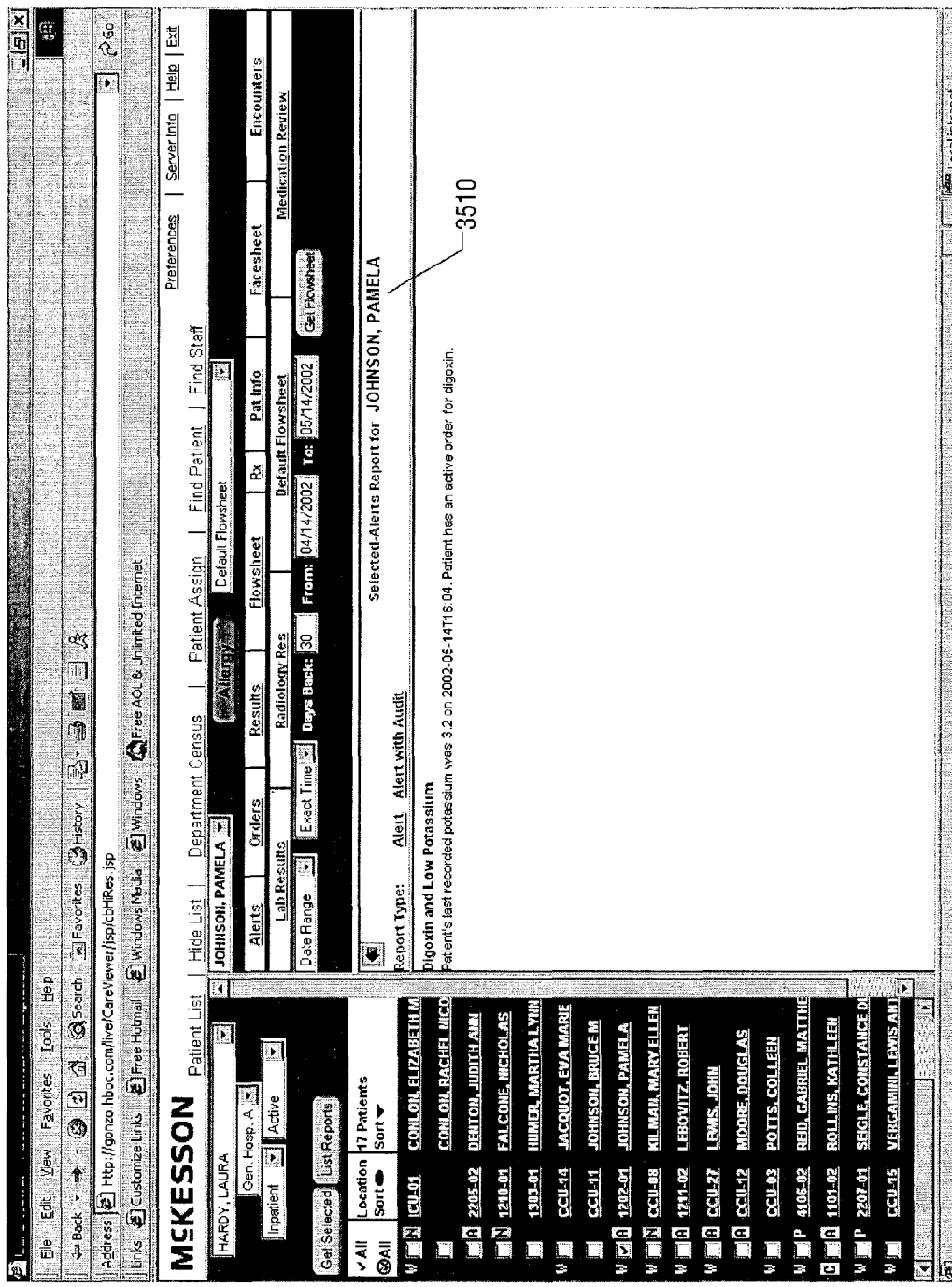
FIG. 35 shows use of the WWW physician portal to alert a clinician or physician about a patient's condition.
Figure 37:
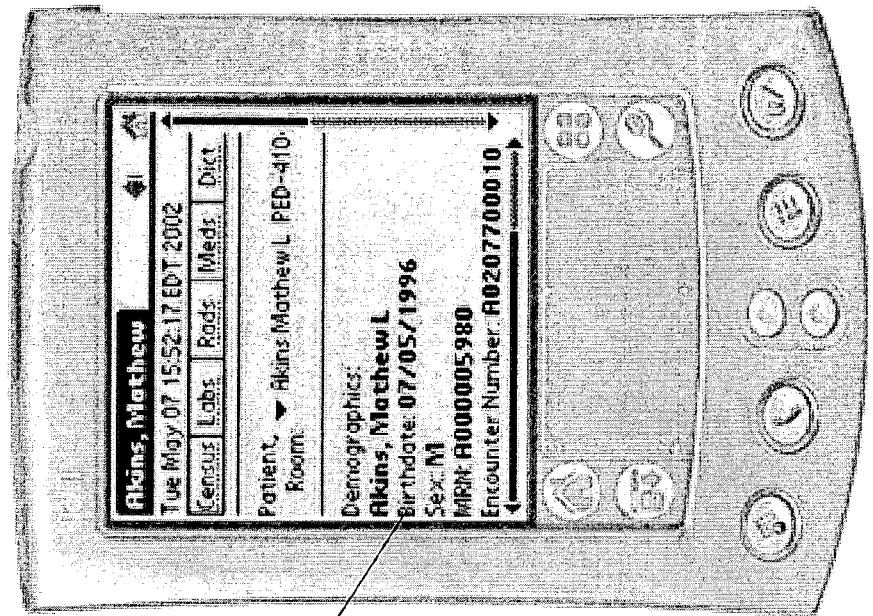
FIG. 37 shows a PDA displaying real time clinical data such as medication administered sent from the monitoring module.
Figure 36:
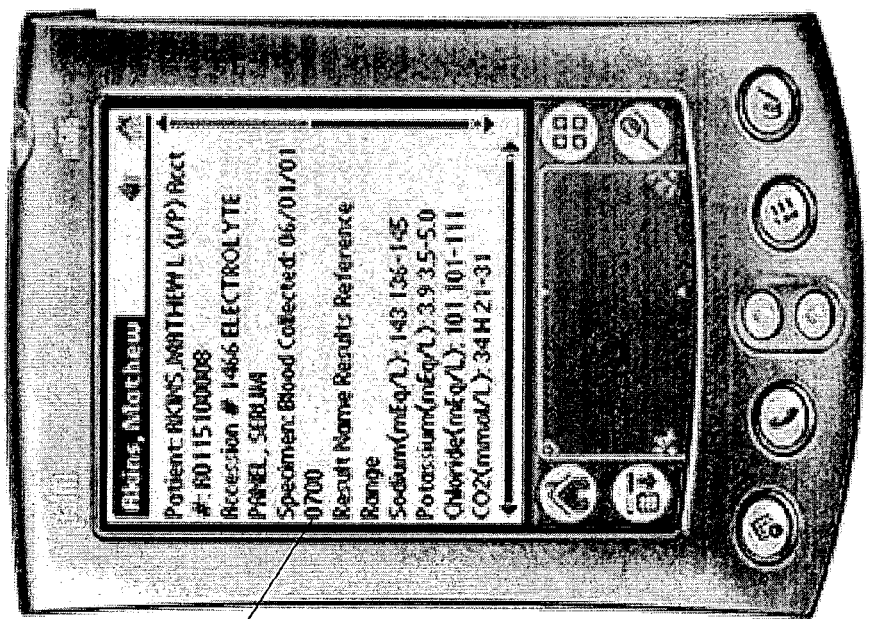
FIG. 36 shows a PDA displaying an alert about a patient's current lab values sent from the monitoring module.

Referring to the screen shots depicted in FIGS. 34 through 37 the interaction of the monitoring module 500 with the prescribing module 100 is shown. FIG. 34 shows a variety of real-time patient information displayed using a WWW physician portal to alert a clinician or physician. The clinician or physician user can review alerts 3510 as shown in FIG. 35 through the physician portal. Furthermore, an alert can be sent from the monitoring module to the user's PDA to display a patient's newest lab values 3630 as shown in FIG. 36 or present real time clinical data such as medications administered 3740 as shown in FIG. 37.

A direct communication connection is not present in one embodiment of the invention of FIG. 1 between the monitoring module 500 and the transcribing 200, dispensing 300 and administering 400 modules. Communication of real time patient data between these modules occurs through the storage and retrieval of information in the patient information DB 20. For example, the monitoring module 500 provides updates directly to the patient information DB 20 and the transcribing 200, dispensing 300 and administering 400 modules all retrieve patient information from the patient information DB 20. Thus, alerts and other real-time data can be relayed from the monitoring module 500 to the transcribing 200, dispensing 300 and administering 400 modules.

Figure 38:
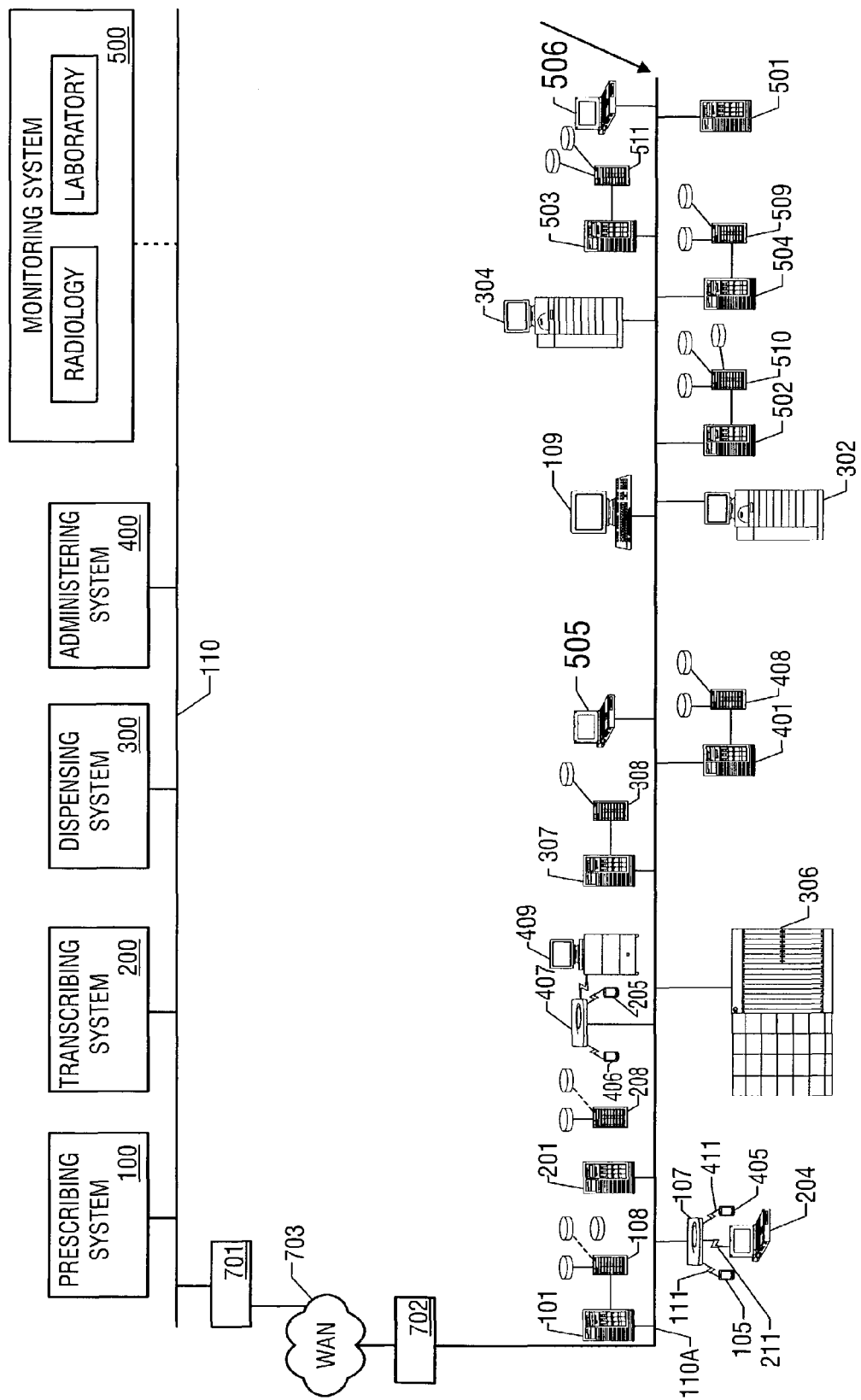
FIG. 38 is an embodiment of the hardware interconnection of two distant patient-care sites communicating over a WAN, each patient-care site having the closed loop medication use system of the present invention.

Referring now to FIG. 38, the CLMUSM can be implemented over a WAN that connects several patient-care site network systems. For simplicity purposes, Patient-Care Site One's LAN 110 is considered to be the exact equivalent of Patient-Care Site Two's LAN 110a. Referring to Patient-Care Site One, the prescribing 100, transcribing 200, dispensing 300, administering 400, and monitoring modules 500 are all connected to LAN 110. Each of these modules 100-500 operate and interface as previously described above in reference to FIGS. 1 through 37. Patient-Care Site One's LAN 110 is connected to router 701, and router 701 is then connected to WAN 703.

Referring to Patient-Care Site Two, the LAN 110a is connected to router 702, and router 702 is connected to WAN 703. In this embodiment, a physician that has patients at both patient-care sites can access patient information, clinical knowledge, and patient alerts on multiple patients from either of the patient-care sites. Moreover, this embodiment allows clinicians access to the patient information of a patient admitted previously to Patient-Care Site One, and later admitted to Patient-Care Site Two. The clinician or physician can retrieve a patients medical history, including current medication, allergies, and previous treatments with the embodiment shown in FIG. 38.

Exemplary embodiments of hardware used in the CLMUSM are shown in FIG. 38 connected to the LAN 110a of Patient-Care Site Two. In one embodiment of Patient-Care Site Two, prescribing DB server 108 is connected to prescribing application server 101, which is connected to network 110a. Wireless access point 107 couples to physician's PDA 105 through communication link 111. Wireless access point 107 also couples to the pharmacist laptop 204 through communication link 211. Additionally, wireless access point 107 also couples to the administering nurse's bar code scanner 405 through communication link 411. Other hardware associated with the prescribing module 100 of FIG. 38 includes a physician's patient-care site terminal 109. Terminal 109 enables the physician to enter a patient's medication and view alerts. In one embodiment of the invention shown in FIG. 38, a robotic medication dispenser 306 is also connected to the LAN 110a, as well as UBCs 302 and 304.

Also connected to the LAN 110a as shown in FIG. 38 and described previously in FIGS. 3, 11, 17; 23, and 32, are an administering application server 401, administering DB server 408, wireless access point 407, administering scanner 406, and administering mobile medication cart with laptop and scanner 409. Included in dispensing module 300 or transcribing module 200 and coupled to LAN 110a of Patient-Care Site Two are a dispensing application server 307, dispensing DB server 308, transcribing application server 201, transcribing DB server 208, pharmacist's PDA 205, patient-care site general application server 502, and patient-care site DB server 510. As part of the monitoring module 500 and coupled to LAN 110a of Patient-Care Site Two are a radiology application server 504, radiology DB server 509, radiology terminal 505, monitoring application server 501, laboratory application server 503, laboratory DB server 511, and laboratory terminal 506.

Figure 39:
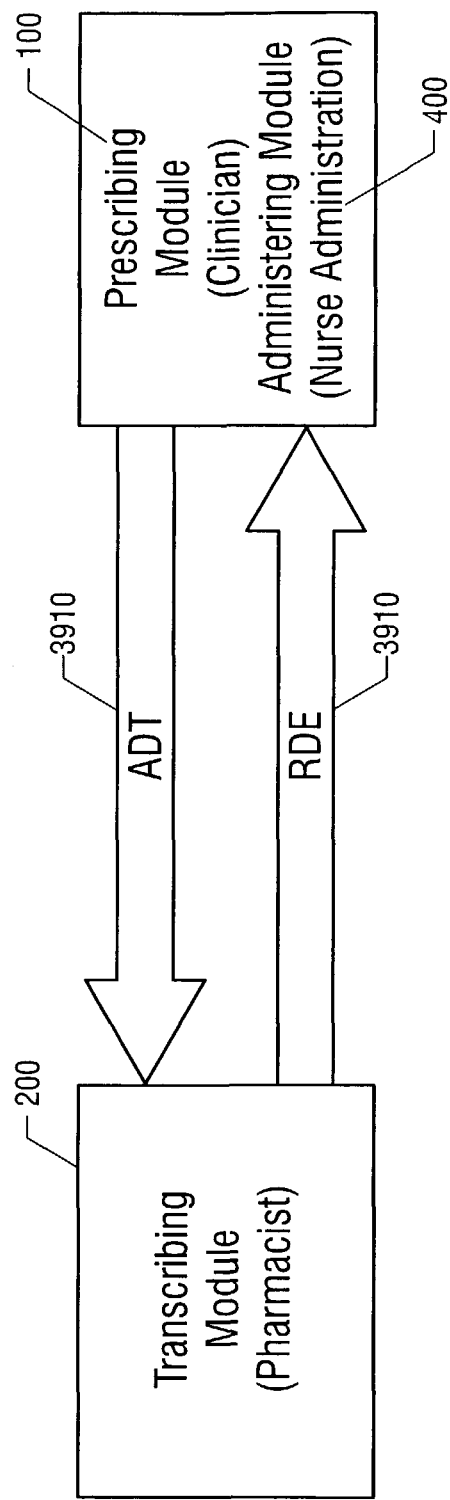
FIG. 39 shows in accordance with one embodiment of the invention a message-passing scheme based on the HL7 messaging protocol.

Referring now to FIG. 39, one embodiment of a message-passing scheme using the HL7 messaging protocol is shown. The HL7 messaging system standardizes the format and protocol for the exchange of sets of data among healthcare computer application systems. In another embodiment, the data is placed in a message packet that is then transmitted over a communication medium. The communication medium may be wired-based such as a coaxial cable or transmitted by open-air wireless transmission or a combination of wire based and open air transmission.

A message packet is comprised of a group of segments in a defined sequence. Each message has a message type that defines its purpose. For example as shown in FIG. 39, in one embodiment, the ADT message type is used to transmit portions of a patient's Patient Administration Data from one module to another. A three-character code 3910 contained within each message identifies its type. The three character codes for HL7 version 2.3 message types are listed in Table 1.

TABLE 1

HL7 MESSAGE TYPES

| Message | Description |
|---------|-------------|
| ACK | General acknowledgment message |
| ADR | ADT response |
| ADT | ADT message |
| BAR | Add/change billing account |
| CRM | Clinical study registration message |
| CSU | Unsolicited study data message |
| DFT | Detail financial transactions |
| DOC | Document response |
| DSR | Display response |
| EDR | Enhanced display response |
| EQQ | Embedded query language query |
| ERP | Event replay response |
| MDM | Medical document management |
| MFD | Master files delayed application acknowledgment |
| MFK | Master files application acknowledgment |
| MFN | Master files notification |
| MFQ | Master files query |
| MFR | Master files response |
| OMD | Dietary order |
| OMN | Nonstock requisition order message |
| OMS | Stock requisition order message |
| ORD | Dietary order - General order acknowledgment message |
| ORF | Query for results of observation |
| ORM | Pharmacy/treatment order message |
| ORN | Nonstock requisition - General order acknowledgment message |
| ORR | General order response message response to any ORM |
| ORS | Stock requisition - General order acknowledgment message |
| ORU | Unsolicited transmission of an observation message |
| OSQ | Query response for order status |
| OSR | Query response for order status |
| PEX | Product experience message |
| PGL | Patient goal message |
| PIN | Patient insurance information |
| PPG | Patient pathway message (goal-oriented) |
| PPP | Patient pathway message (problem-oriented) |
| PPR | Patient problem message |
| PPT | Patient pathway goal-oriented response |
| PPV | Patient goal response |
| PRR | Patient problem response |
| PTR | Patient pathway problem-oriented response |
| QCK | Deferred query |
| QRY | Query, original mode |
| ROR | Pharmacy/treatment order response |
| RAR | Pharmacy/treatment administration information |
| RAS | Pharmacy/treatment administration message |
| RCI | Return clinical information |
| RCL | Return clinical list |
| RDE | Pharmacy/treatment encoded order message |
| RDO | Pharmacy/treatment order message |
| RDR | Pharmacy/treatment dispense information |
| RDS | Pharmacy/treatment dispense message |
| REF | Patient referral |
| RER | Pharmacy/treatment encoded order information |
| RGR | Pharmacy/treatment dose information |
| RGV | Pharmacy/treatment give message |
| RPA | Return patient authorization |
| RPI | Return patient information |
| RPL | Return patient display list |
| RPR | Return patient list |
| RQA | Request patient authorization |
| RQC | Request clinical information |
| RQI | Request patient information |
| RQP | Request patient demographics |
| RQQ | Event replay query |
| RRA | Pharmacy/treatment administration acknowledgement message |
| RRD | Pharmacy/treatment dispense acknowledgment message |
| RRE | Pharmacy/treatment encoded order acknowledgment message |
| RRG | Pharmacy/treatment give acknowledgment message |
| RRI | Return referral information |
| RRO | ORR message for pharmacy/treatment |
| SIU | Schedule information unsolicited |
| SPQ | Stored procedure request |
| SQM | Schedule query message |
| SQR | Schedule query response |
| SRM | Schedule request message |

TABLE 1-continued

HL7 MESSAGE TYPES

| Message | Description |
|---|---|
| SRR | Scheduled request response |
| SUR | Summary product experience report |
| TBR | Tabular data response |
| UDM | Unsolicited display update message |
| VQQ | Virtual table query |
| VXQ | Query for vaccination record |
| VXR | Vaccination record response |
| VXU | Unsolicited vaccination record update |
| VXX | Response for vaccination query with multiple PID matches |

In one embodiment of the invention, a HL7 based message passing protocol can be used to pass messages between modules of the CLMUSM as shown in FIG. 39 or for message passing within a module. The HL7 messaging protocol is described in the Health Level Seven Standard Developing Organization's "HL7 Version 3," "HL7 Version 2.4," "HL7 Version 2.3.1," and "HL7 Version 2.3" specifications, all of which are herein incorporated by reference in their entireties. The following description of exemplary embodiments of the invention shown in FIGS. 1-42 will be more particularly described with reference to a modified "HL7 Version 2.3" specification. As is known to one of ordinary skill in the art, any version of the HL7 messaging protocol as well as generic message passing schemes may be used to implement communication between the modules. Thus, the description of the figures below using the modified "HL7. Version 2.3" specification is not meant to narrow the scope of the invention, but is for illustrative purposes only.

Referring still to FIG. 39, a message flow diagram shows the transfer of messages between the transcribing module 200, prescribing module 100, and administering module 400. A physician or other clinician in prescribing module 100 inputs demographic information about a new patient and the patients visit history and next visit. The prescribing module codes this information into an ADT type message using the HL7 protocol. As shown in FIG. 39, the message is transmitted 3910 to transcribing module 200 and to a patient information DB (not shown). Next, the physician or clinician certified to prescribe medications submits information for a pharmacy prescription order into the prescribing module 100. The prescribing module codes this information into an ORM message type using the HL7 protocol. In one embodiment of the invention, the ORM message type includes a trigger event type that has a code of O01. Thus, the event of the physician submitting a prescription order into the prescribing module 100 generates a trigger event of O01. The O01 trigger event in HL7 is a request to the prescribing module to generate an ORM message type. This ORM message is sent to the transcribing module 200 for review and verification. In one embodiment of the invention, the ORM message type may mimic a prescription slip, taking the form of a string of text identifying a preferred medication. In an alternative embodiment, it may include all the relevant data necessary to complete the encoded, verified order after review by a pharmacist and the transcribing module 200. An ORM message order is considered verified after receipt of the pharmacy encoded order message RDE. The pharmacy prescription order message ORM is used by the physician or clinician to place new orders, cancel existing orders, update existing orders and similar tasks for modifying prescription orders. The information contained in an ORM message is given below in Table 2.

TABLE 2

| ORM^O01 | Pharmacy Prescription Order Message |
|---|---|
| MSH | Message Header |
| [{NTE}] | Notes and Comments (for MSH) |
| [ | |
| PID | Patient Identification |
| [PD1] | Additional Demographics |
| [{NTE}] | Notes and Comments (for PID) |
| [PV1 | Patient Visit |
| [PV2]] | Patient Visit - Additional Info |
| [{IN1 | Insurance |
| [IN2] | Insurance Additional Info |
| [IN3] | Insurance Add'l Info - Cert. |
| }] | |
| [GT1] | Guarantor |
| [{AL1}] | Allergy Information |
| ] | |
| { | |
| ORC | Common Order |
| [ | |
| RXO | Pharmacy/Treatment Order |
| [{NTE}] | Notes and Comments (for RXO) |
| {RXR} | Pharmacy/Treatment Route |
| [ | |
| {RXC} | Pharmacy/Treatment Component |
| [{NTE}] | Notes and Comments (for Results) |
| ] | |
| [ | |
| { | |
| OBX | Observation/Result |
| [{NTE}] | Notes and Comments (for OBX) |
| } | Billing Segment |
| ] | |

In one embodiment of the invention, the transcribing module 200 sends an ORR message type (not shown in FIG. 39) after receiving an unverified ORM pharmacy order message from the prescribing module 100. After the ORR message is sent to the prescribing module 100 to acknowledge receipt of the ORM message, the ORM message is stored in an inactive pending state by the transcribing module 200. The ORR message is generated by the transcribing module without any pharmacist-activated input or event. As described in greater detail below, in one embodiment of the invention, after the pharmacist reviews and verifies the unverified pharmacy order message ORM, the transcribing module then generates a RDE encoded pharmacy order message. Table 3 shows the information present in the ORR message type.

TABLE 3

| ORR | General Order Acknowledgment Message |
|---|---|
| MSH | Message Header |
| MSA | Message Acknowledgment |
| [ERR] | Error |
| [{NTE}] | Notes and Comments (for Header) |
| [ | |
| [ | |
| PID | Patient Identification |
| [{NTE}] | Notes and Comments (for Patient ID) |
| ] | |
| { | |
| ORC | Common Order |
| [ | |
| RXO | Pharmacy/Treatment Order |
| [{NTE}] | Notes and Comments (for RXO) |
| {RXR} | Pharmacy/Treatment Route |
| [{RXC}] | Pharmacy/Treatment Component |
| [{NTE}] | Notes and Comments (for RXC) |
| ] | |
| } | |
| ] | |

As shown in FIG. 39, after the transcribing module 200 receives an ORM message, the pharmacist reviews the prescription order in the ORM message. Once the pharmacist has reviewed the unverified prescription order, the pharmacist then performs the appropriate actions in the transcribing module 200 to verify the order. Verification of the prescription order includes reviewing the appropriateness of the unverified prescription order and approving the order as is, modifying the order or sending an alert to the prescribing module 100. In one embodiment of the invention, the pharmacists verification of the order generates a RDE trigger event with a code of Z01 (medication order), Z02 (small volume ("Piggyback") IV order), or Z03 (large volume prescription ("LVP") IV order) within the transcribing module 200. The transcribing module 200 in response to the trigger event generates an RDE pharmacy encoded order message that includes the pharmacist's response to the ORM prescription order and other information as shown in Table 4. In one aspect of an embodiment of the invention, each ORM message received by the transcribing module 200 results in an RDE message being generated and transmitted to the prescribing module 100 and administering module 400. An RDE message may also be sent as an unsolicited message that is not in response to an ORM message to report on either a single order or multiple pharmacy orders for a patient.

TABLE 4

| RDE^Znn | Pharmacy Encoded Order Message |
|---|---|
| MSH | Message Header |
| [{NTE}] | Notes and Comments (for Header) |
| [ | |
| PID | Patient Identification |
| [PD1] | Additional Demographics |
| [{NTE}] | Notes and Comments (for PID) |
| [ | |
| PV1 | Patient Visit |
| [PV2] | Patient Visit - Additional Info |
| ] | |
| [ | |
| {IN1 | Insurance |
| [IN2] | Insurance Additional Info |
| [IN3] | Insurance Add'l Info - Cert. |
| } | |
| ] | |
| [GT1] | Guarantor |
| [{AL1}] | Allergy Information |
| ] | |
| { | |
| ORC | Common Order |
| [ | |
| RXO | Pharmacy/Treatment Prescription Order |
| [{NTE}] | Notes and Comments (for RXO) |
| {RXR} | Pharmacy/Treatment Route |
| [ | |
| {RXC} | Pharmacy/Treatment Component (for RXO) |
| [{NTE}] | Notes and Comments (for RXC) |
| ] | |
| ] | |
| RXE | Pharmacy/Treatment Encoded Order |
| {RXR} | Pharmacy/Treatment Route |
| [{RXC}] | Pharmacy/Treatment Component (for RXE) |
| { | |
| [OBX] | Results |
| [{NTE}] | Notes and Comments (for OBX) |
| } | |
| {[CTI]} | Clinical Trial Identification |
| } | |

After the transcribing module 200 sends an RDE message to the prescribing module 100, the prescribing module 100 acknowledges the RDE message with an RRE pharmacy encoded order acknowledgment message type (not shown in FIG. 39). The RRE message is sent to the transcribing module 200 and includes information on whether the physician agreed to the pharmacist's actions in the RDE message. Thus, if the pharmacist in the RDE message states that the frequency of administering the medication should be changed, the RRE message acknowledges whether the physician has agreed to this change. Table 5 shows the information present in the RRE message type.

TABLE 5

| RRE | Pharmacy Encoded Order Acknowledgment Message |
|---|---|
| MSH | Message Header |
| MSA | Message Acknowledgment |
| [ERR] | Error |
| [{NTE}] | Notes and Comments (for Header) |
| [ | |
| [ | |
| PID | Patient Identification |
| [{NTE}] | Notes and Comments (for PID) |
| ] | |
| { | |
| ORC | Common Order |
| [ | |
| RXE | Pharmacy/Treatment Encoded Order |
| {RXR} | Pharmacy/Treatment Route |
| [{RXC}] | Pharmacy/Treatment Component |
| ] | |
| } | |
| ] | |

In one embodiment of the invention, after receiving an RRE acknowledgment message from the prescribing module 100, the transcribing module 200 transmits a RDS pharmacy dispense message type to the dispensing module 300 and administering module 400. An RDS message is generated by the transcribing module 200 for each instance of dispensing a medication to fill a new order or for refill of an existing order. The information present in the RDS message type is shown in Table 6.

TABLE 6

| RDS^O01 | Pharmacy Dispense Message |
|---|---|
| MSH | Message Header |
| [{NTE}] | Notes and Comments (for MSH) |
| [ | |
| PID | Patient Identification |
| [PD1] | Additional Demographics |
| [{NTE}] | Notes and Comments (for PID) |
| [{AL1}] | Allergy |
| [ | |
| PV1 | Patient Visit |
| [PV2] | Patient Visit - Additional Info |
| ] | |
| ] | |
| { | |
| ORC | Common Order |
| [ | |
| RXO | Pharmacy/Treatment Order |
| [{NTE}] | Notes and Comments (for RXO) |
| {RXR} | Pharmacy/Treatment Route (for RXO) |
| [ , | |
| {RXC} | Pharmacy/Treatment Component |
| [{NTE}] | Notes and Comments (for RXC) |
| ] | |
| ] | |
| [ | |
| RXE | Pharmacy/Treatment Encoded Order |
| {RXR} | Pharmacy/Treatment Route (for RXE) |
| [{RXC}] | Pharmacy/Treatment Component (for RXE) |
| { | |
| RXD | Pharmacy/Treatment Dispense |
| {RXR} | Pharmacy/Treatment Route (for RXD) |
| [{RXC}] | Pharmacy/Treatment Component (for RXD) |
| { | |

TABLE 6-continued

| RDS^O01 | Pharmacy Dispense Message |
|---|---|
| OBX | Results |
| [{NTE}] | Notes and Comments (for OBX) |
| } | |
| } | |

The dispensing module 300 acknowledges receipt of a RDS message by transmitting an RRD pharmacy dispense acknowledgment message type to the transcribing module 200. The information present in the RRD message type is shown in Table 7.

TABLE 7

| RRD^O02 | Pharmacy Dispense Acknowledgment Message |
|---|---|
| MSH | Message Header |
| MSA | Message Acknowledgment |
| [ERR] | Error |
| [{NTE}] | Notes and Comments (for MSA) |
| [ | |
| [ | |
| PID | Patient Identification |
| [{NTE}]] | Notes and Comments (for Patient ID) |
| { | |
| ORC | Common Order |
| [ | |
| RXD | Pharmacy/Treatment Dispense |
| {RXR} | Pharmacy/Treatment Route (for RXD) |
| [{RXC}] | Pharmacy/Treatment Component (for RXD) |
| ] | |
| } | |
| ] | |

In one embodiment of the invention, after receiving an RDS acknowledgment message from the dispensing module, the transcribing module 200 sends an RGV pharmacy give message type to the administering module 400. The pharmacy give message RGV provides explicit schedule information for a specific pharmacy encoded order message RDE. A RGV message uses a RXG segment to record medication or treatment administration instructions. It may carry information about a single scheduled administration on a medication or treatment, or it may carry information about multiple administrations. The information present in the RGV message type is shown in Table 8.

TABLE 8

| RGV | Pharmacy Give Message |
|---|---|
| MSH | Message Header |
| [{NTE}] | Notes and Comments (for MSH) |
| [ | (begin optional patient data) |
| PID | Patient Identification |
| [PD1] | Additional Demographics |
| [{NTE}] | Notes and Comments (for PID) |
| [{AL1}] | Allergy |
| [ | |
| PV1 | Patient Visit |
| [PV2] | Patient Visit - Additional Info |
| ] | |
| { | |
| ORC | Common Order |
| [ | |
| RXO | Pharmacy/Treatment Order |
| [ | |
| {NTE} | Notes and Comments (for RXO) |
| {RXR} | Pharmacy/Treatment Route |
| [ | |
| {RXC} | Pharmacy/Treatment Component |
| [{NTE}] | Notes and Comments (for RXC) |

TABLE 8-continued

| RGV | Pharmacy Give Message |
|---|---|
| ] | |
| ] | |
| ] | |
| [ | |
| RXE | Pharmacy/Treatment Encoded Order |
| {RXR} | Pharmacy/Treatment Route (for RXE) |
| [{RXC}] | Pharmacy/Treatment Component (for RXE) |
| ] | |
| { | |
| RXG | Pharmacy/Treatment Give |
| {RXR} | Pharmacy/Treatment Route (for RXG) |
| [{RXC}] | Pharmacy/Treatment Component (for RXG) |
| { | |
| [OBX] | Observation/Results |
| [{NTE}] | Notes and Comments (for OBX) |
| } | |
| } | |
| } | |

After the transcribing module 200 sends an RGV message to the administering module 400, the administering module 400 acknowledges the RGV message with an RRG pharmacy give acknowledgment message type. The RRG message is sent to the transcribing module 200 and includes information on whether the nurse administrator agreed to the pharmacist's actions in the RGV message. Thus, if the pharmacist in the RGV message states that the frequency of administering the medication should be changed, the RRG message acknowledges whether the nurse administrator has agreed to this change. Table 9 shows the information present in the RRG message type.

TABLE 9

| RRG^O02 | Pharmacy Give Acknowledgment Message |
|---|---|
| MSH | Message Header |
| MSA | Message Acknowledgment |
| [ERR] | Error |
| [{NTE}] | Notes and Comments (for MSH) |
| [ | |
| [ | |
| PID | Patient Identification |
| [{NTE}] | Notes and Comments (for PID) |
| ] | |
| { | |
| ORC | Common Order |
| [ | |
| RXG | Pharmacy/Treatment Give |
| {RXR} | Pharmacy/Treatment Route |
| [{RXC}] | Pharmacy/Treatment Component |
| ] | |
| } | |
| ] | |

After the nurse administrator completes administration of a prescription order, the administering module creates a RAS pharmacy administration message type. The administering module 400 can report several administrations of medication for a given order with a single RAS message, with each administration reported by a separate (repeating) RXA segment.

In one embodiment of the invention, RAS messages are sent from the administering module 400 to the transcribing module 200 and monitoring module 500 that then use the information in the message to generate alerts and medication administration reports. The alerts and reports are forwarded to the prescribing module 100 and transcribing module 200 for display to the clinician, physician, pharmacist, or other interested persons. Table 10 shows the information present in the RAS message type.

TABLE 10

| RAS | Pharmacy Administration Message |
|---|---|
| MSH | Message Header |
| [{NTE}] | Notes and Comments (for MSH) |
| [ | |
| PID | Patient Identification |
| [PD1] | Additional Demographics |
| [{NTE}] | Notes and Comments (for PID) |
| [{AL1}] | Allergy Information |
| [ | |
| PV1 | Patient Visit |
| [PV2]] | Patient Visit - Additional Info |
| ] | |
| ] | |
| { | |
| ORC | Common Order |
| [ | |
| RXO | Pharmacy/Treatment Order |
| [ | |
| {NTE} | Notes and Comments (for RXO) |
| {RXR} | Pharmacy Route (for RXO) |
| [ | |
| {RXC} | Pharmacy Component (for RXO) |
| [{NTE}] | Notes and Comments (for RXC) |
| ] | |
| ] | |
| ] | |
| [ | |
| RXE | Pharmacy/Treatment Encoded Order |
| {RXR} | Pharmacy/Treatment Route (for RXE) |
| [{RXC}] | Pharmacy/Treatment Component (for RXE) |
| ] | |
| {RXA} | Pharmacy/Treatment Administration |
| RXR | Pharmacy/Treatment Route (for RXA) |
| { | |
| [ | |
| OBX | Observation/Result |
| {[NTE]} | Notes and Comments (for OBX) |
| ] | |
| } | |
| {[CTI]} | Clinical Trial Identification |
| } | |

The transcribing 200 and monitoring modules acknowledge receipt of a RAS message by transmitting an RRA pharmacy administration acknowledgment message type to the administering module. The information present in the RRA message type is shown in Table 11.

TABLE 11

| RRA^O02 | Pharmacy Administration Acknowledgment Message |
|---|---|
| MSH | Message Header |
| MSA | Message Acknowledgment |
| [ERR] | Error |
| [{NTE}] | Notes and Comments (for MSA) |
| [ | |
| [ | |
| PID | Patient Identification |
| [{NTE}] | Notes and Comments (for PID) |
| ] | |
| { | |
| ORC | Common Order |
| [ | |
| {RXA} | Pharmacy/Treatment Administration |
| RXR | Pharmacy/Treatment Route |
| ] | |
| } | |
| ] | |

Figure 40:
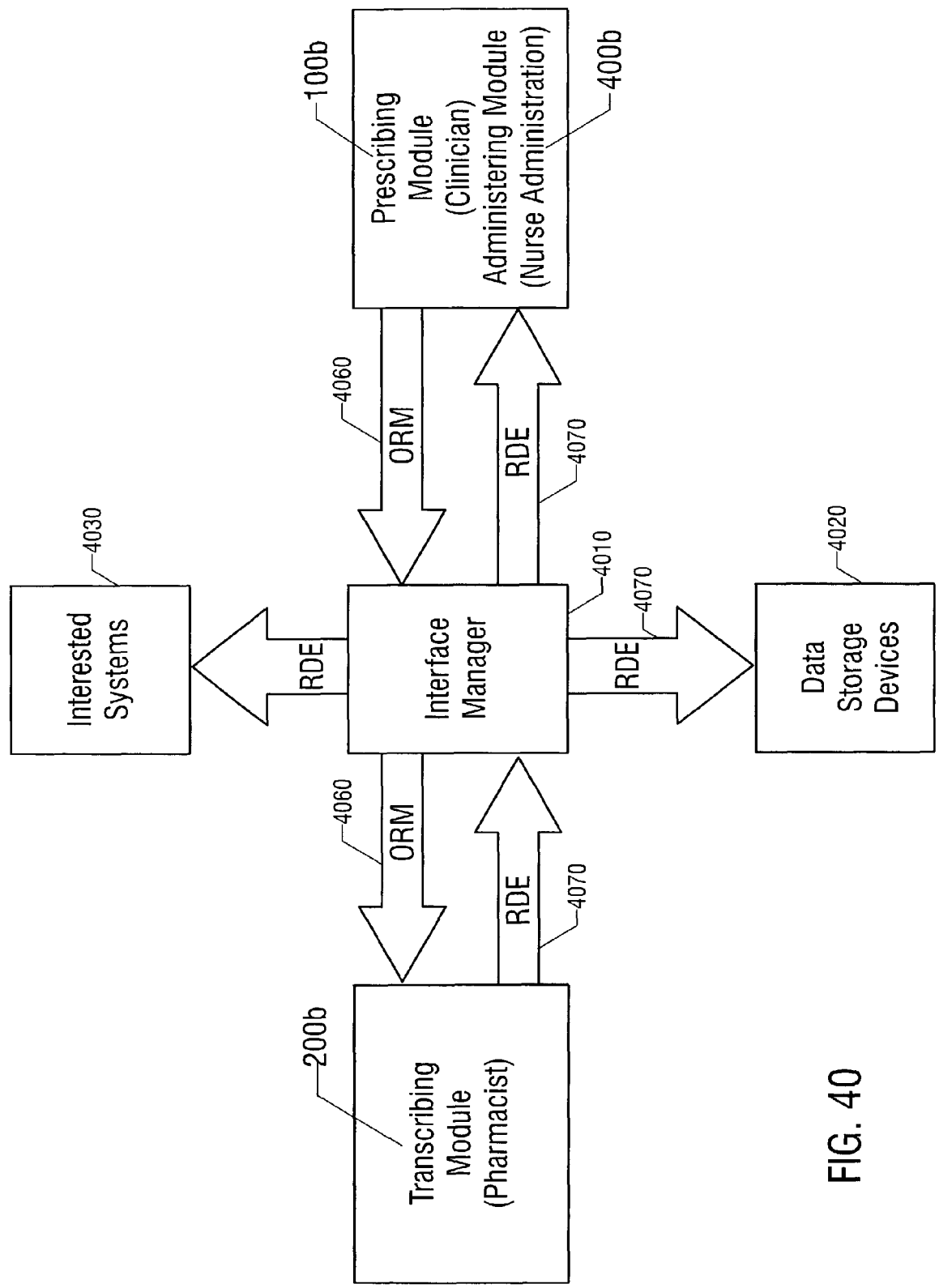
FIG. 40 shows an alternative embodiment of the closed loop medication use system incorporating a centralized interface manager and based on the HL7 messaging protocol.

Referring now to FIG. 40, an alternative embodiment of the CLMUSM is shown that implements the messaging system described above. The centralized server model shown in FIG. 40 is similar to FIG. 2A. Interface manager 4010 includes one or more application servers interconnected to create a high performance computer server system. Data storage devices 4020 shown in FIG. 40 may include the databases 10b, 20b, 21b, 30b, 40b, 50b, 60b, 70b, 90b shown in FIG. 2A coupled to interface manager 4010. The prescribing 100b, transcribing 200b, and administering 400b modules do not directly communicate with each other. Interested systems 4030 that includes the dispensing module and monitoring module (not shown) are also connected to the other modules and the data storage devices through the interface manager 4010. As shown in FIG. 40, modules are interconnected through network connections and message passing between the modules and data storage devices processed using interface manager 4010.

In one embodiment of the invention shown in FIG. 40, a clinician or physician in the prescribing module 100b creates a prescription order. The prescription order is sent in an ORM pharmacy prescription order message type to the interface manager that processes and sends the ORM message 4060 to the transcribing module 200b. The interface manager may directly send (not shown in FIG. 40) the ORM message 4060 received from the prescribing and administering modules to interested systems 4030 or data storage devices 4020 based on the message passing protocol implementation. After the transcribing module 200b receives the ORM message, the pharmacist reviews the prescription order in the ORM message. The pharmacist then performs the appropriate actions in the transcribing module to verify the order. The transcribing module in response to the pharmacist's verification generates a RDE pharmacy encoded order message type. As illustrated in FIG. 40, the RDE message 4070 is sent to the interface manager 4010 which then broadcasts the RDE message to interested systems 4030, data storage devices 4020 and to prescribing 100b and administering 400b modules.

Figure 41:
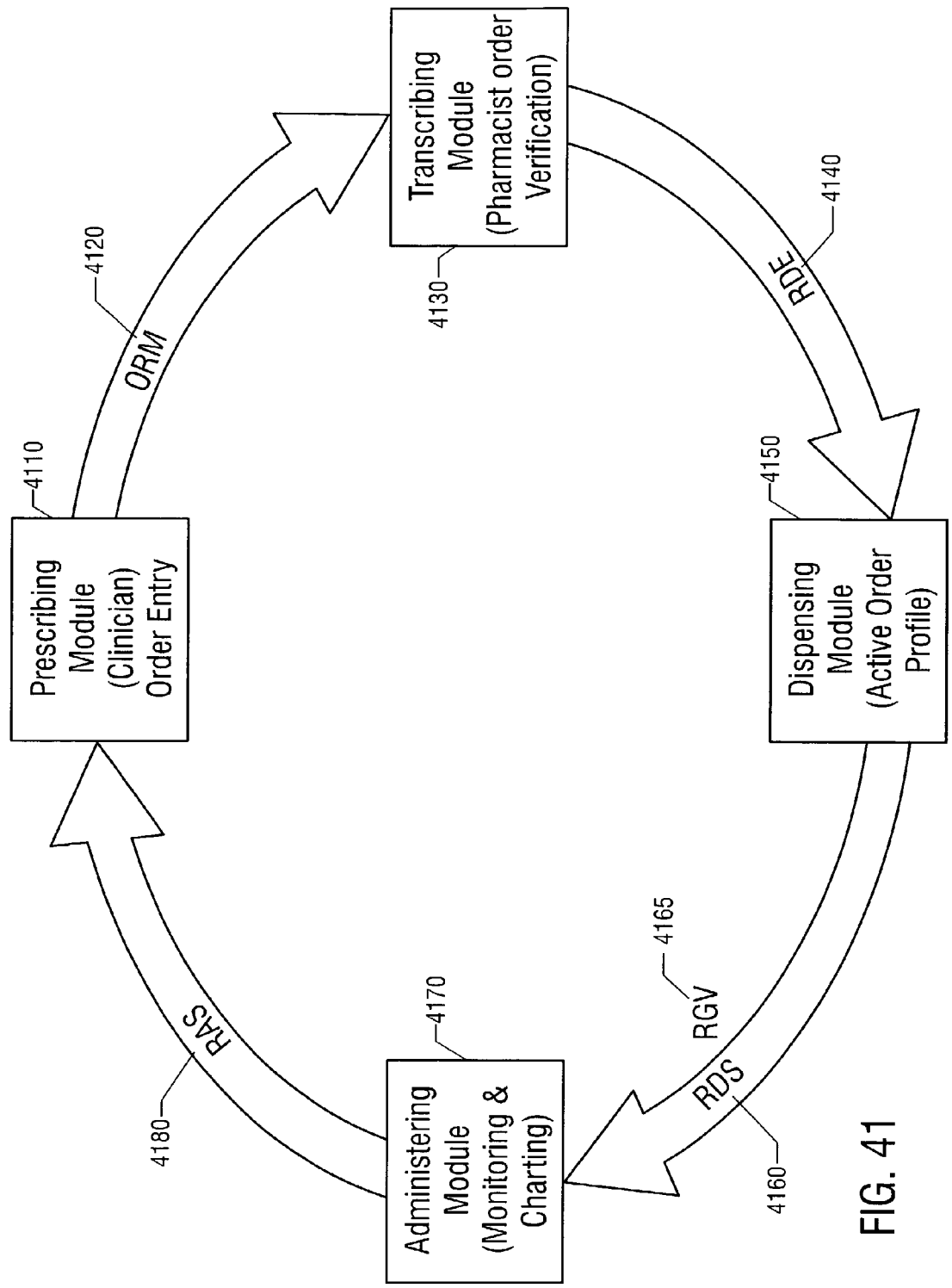
FIG. 41 shows a HL7 based messaging system in accordance with one embodiment of the CLMUSM invention.

Turning now to FIG. 41, a HL7 based messaging system in accordance with one embodiment of the CLMUSM invention is shown. FIG. 41 shows the underlying message passing for the exemplary systems shown in FIGS. 1 and 2. Prescribing module 4110 permits a clinician or physician to enter a prescription order that is transmitted in an ORM pharmacy prescription order message 4120 to a transcribing module 4130. The transcribing module 4130 allows a pharmacist to view and verify the ORM prescription order message 4120. The transcribing module in response to the pharmacist's verification of the ORM message generates a RDE 4140 pharmacy encoded order message type. In one embodiment, RDE message 4140 is sent to a dispensing module 4150 in which it is placed in an active order profile queue. In another embodiment shown in FIG. 41, the RDE message 4140 is not transmitted to any other module. The RDE message indicates to the dispensing module the medications to dispense. After receiving an RDE message from the transcribing module 4130, the dispensing module 4150 transmits a RDS pharmacy dispense message type 4160 to the administering module 4170. The RDS message informs the nurse or medication administrator that the prescription order is ready to dispense. Referring to FIG. 41, after transmitting an RDS message to the administering module 4170, the dispensing module sends an RGV pharmacy give message type 4165 to the administering module 4170. The RGV message provides explicit schedule information for a prescription order to the nurse. After retrieving the medications from the dispensing module 4150, the nurse or medication administrator verifies the five "rights" of medication administration as described above with the assistance of administering module 4170. In one embodiment of the invention shown in FIG. 41, administering module 4170 continuously monitors, stores and charts the patient's condition. Administering module 4170 communicates information on the patient's condition including medication alerts (i.e. allergic reactions, adverse medication events) to the prescribing module 4110 thus, allowing the clinician immediate and continuous access to the patient's condition. As shown in FIG. 41, after the nurse or medication administrator completes administration of a prescription order, the administering module 4170 generates a RAS pharmacy administration message 4180 type. The RAS message 4180 communicates patient information and alerts to the prescribing module 4110.

Figure 42:
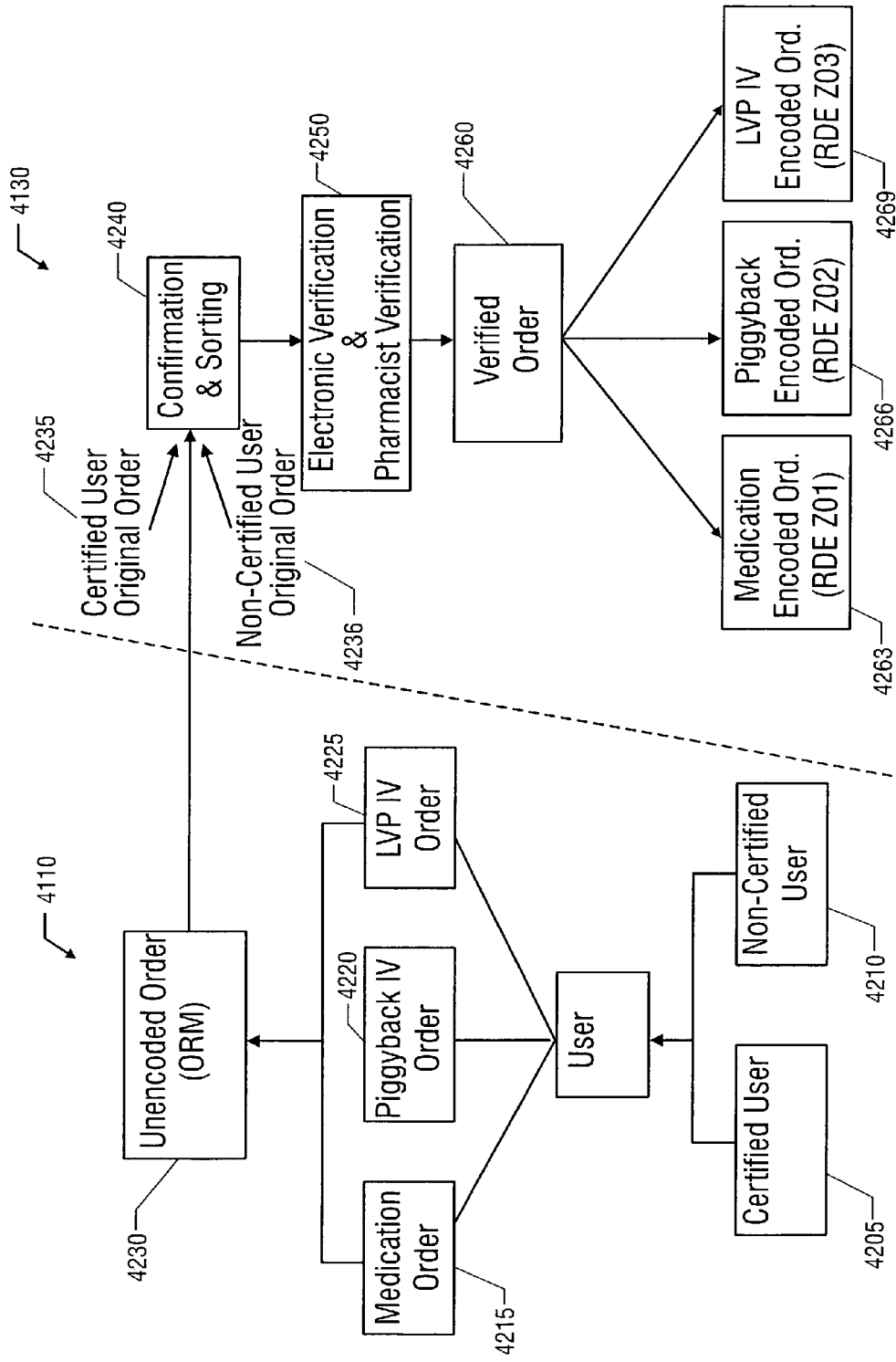
FIG. 42 is a flow diagram showing the steps involved in message passing for the prescribing and transcribing of prescription orders.

Referring now to FIG. 42, a flow diagram of the steps of message passing for the prescribing and transcribing of prescription orders for the system of FIG. 41 is shown. A certified user 4205 or non-certified user 4210 may submit a prescription order to the prescribing module 4110. A certified user 4205 is a physician or clinician authorized to prescribe medications to patients in a patient-care environment. A non-certified user 4210 is a person who is not certified to prescribe medications to patients. Examples of non-certified users 4210 include ward secretaries, licensed practical nurses ("LPN"), registered nurses ("RN"), pharmacists or any other person approved by the patient-care site to enter prescription orders into the prescribing module 4110 from a certified user's written orders. In one embodiment of the invention, prescription orders entered into the prescribing module 4110 by a non-certified user 4210 must be accompanied by an original copy of the written order (NCR copy, faxed copy or fax viewed copy). The order entered by the user is categorized into a medication order 4215, piggyback IV order 4220, or a LVP IV order 4225. The prescribing module 4110 takes the categorized order and generates an unencoded pharmacy prescription order message ORM 4230. ORM message 4230 is sent to the transcribing module 4130 where it is verified.

The transcribing module 4130 includes a pharmacist selected parameter "Certified User Original Order" ("CUOO") 4235 and "Non-Certified User Original Order" ("NCUOO") 4236 that indicates the source of the order. An ORM message contains information on whether the prescription order was entered into the prescribing module 4110 by a certified user 4205 or a non-certified user 4210. If both the CUOO parameter and NCUOO parameter is set for "verification," all ORM message prescription orders must be confirmed 4240 against the original written order. Alternatively, if only the NCUOO parameter is set for "verification," ORM messages that contain a prescription order entered by a non-certified user must be confirmed against an original written order 4240.

After confirmation against an original written order, the prescription order is sorted 4240 based on whether the order was entered into the prescribing module 4110 by a certified user 4205 or a non-certified user 4210. Prescription order messages from non-certified users 4210 are distinctly displayed in the pharmacy work queue for comparison with the original copy of the written order by the pharmacist. The transcribing module 4130 also performs electronic verification 4250 of the order by reviewing the appropriateness of the unverified prescription order, examining real-time patient information, such as allergies, and current diet and medications the patient is taking, and by examining medication information for possible adverse medication interactions and any administering guidelines or requirements. With the assistance of information provided by the transcribing module 4130, the pharmacist assesses and verifies the appropriateness of the prescription order. The verified order 4260, based on the category of prescription order, is placed into a medication encoded order message 4263 (RDE^Z01), piggyback IV encoded order message 4266 (RDE^Z02), or a LVP IV encoded order message 4269 (RDE^Z03) as shown in FIG. 42.

The particular embodiments disclosed above are illustrative only, as the invention may be modified and practiced in different but equivalent manners apparent to those skilled in the art having the benefit of the teachings herein. It is therefore evident that the particular embodiments disclosed above may be altered or modified and all such variations are considered within the scope and spirit of the invention. It is intended that the following claims be interpreted to enhance all such variations and modifications.

What is claimed is:

1. A method comprising:
    receiving a prescription order for prescribing medication to a patient from a prescribing computing apparatus at a first computing apparatus;
    placing, by the first computing apparatus, the prescription order in a queue including one or more other prescription orders using a scheduling technique, wherein placing the prescription order in a queue comprises (1) prioritizing the queue based on one or more scheduled follow-up medication interventions, (2) receiving selection of a prescription order from the queue, (3) receiving input at the first computing apparatus to indicate verification of an appropriateness of the selected prescription order, and (4) generating a verified prescription order by the first computing apparatus in response thereto;
    sending the verified prescription order to one or more other computing apparatuses to facilitate (1) dispensing the medication, (2) providing a medication administration task to direct administering the medication to the patient, and (3) monitoring status reports submitted, electronically by medical personnel, regarding the patient after administering the medication, wherein sending the verified prescription comprises sending the verified prescription to a dispensing location selected based on an availability of a medication inventory of a medication identified by the verified prescription at one or more dispensing locations associated with the one or more other computer apparatuses, wherein information related to the dispensing, administering and monitoring is recorded and made available for a subsequent verification of the appropriateness of a prescription order for a subsequent prescribing of medication to the patient, and
    receiving and presenting by the first computing apparatus clinical information related to one or more of the dispensing, administering or monitoring for a previous prescribing of medication to the patient before receiving input to indicate verification to thereby facilitate the verification, said clinical information including real-time patient information, medication information that includes possible adverse medication interactions, or administering guidelines, the clinical information being presented to thereby facilitate a comparison of the prescription order and the clinical information;
    receiving in at least one instance an indication of an error based upon the comparison of the prescription order and the clinical information; and in response thereto,
    receiving input at the computing apparatus modifying the prescription order; and
    sending a message including the modified prescription order to the prescribing computing apparatus.

2. The method of claim 1, wherein receiving a prescription order, sending the verified prescription order and receiving information related to the dispensing, administering and monitoring include communicating information over an electronic medium, wherein the electronic medium is a network, World Wide Web, or intranet.

3. The method of claim 2, wherein receiving a prescription order comprises receiving an electronic prescription order, the electronic prescription order having been converted from a non-electronic prescription order into the electronic prescription order by scanning or faxing the non-electronic prescription.

4. The method of claim 2, wherein communicating information comprises communicating information using a communications protocol.

5. The method of claim 4, wherein the communications protocol is a health level seven messaging protocol.

6. The method of claim 1, further comprising prescribing the medication on the prescription order before receiving the prescription order at the computing apparatus, wherein prescribing comprises:
   receiving information generated from monitoring the patient;
   comparing the generated information to medication selection criteria; and
   determining at least one recommended medication based on the comparing.

7. The method of claim 6, wherein the medication selection criteria is from the group consisting of patient specific information, medication information, laboratory and radiology information, standard of care information, healthcare industry recommended treatment information, verified prescription orders, and alerts.

8. The method of claim 7, wherein the operation of comparing comprises:
   suggesting a plurality of recommended medications; and
   calculating an individual cost for each of the plurality of recommended medications.

9. The method of claim 1, wherein the message is an alert.

10. The method of claim 1, further comprising:
    determining at the computing apparatus the dispensing location based on a plurality of dispensing requirements, the dispensing location being determined from one or more dispensing locations available for dispensing the medication.

11. The method of claim 10, wherein the dispensing requirement includes patient location, type of medication, medication location, or quantity of medication needed.

12. The method of claim 10, wherein the one or more dispensing locations available for dispensing the medication include one or more of a robotic dispensing system, an automated storage and retrieval system, or medication dispensing cabinets.

13. The method of claim 1, further comprising receiving the verified prescription order and dispensing the medication from the verified prescription order, wherein the step of dispensing the medication comprises electronically verifying the dispensed medication is the correct medication for the patient.

14. The method of claim 1, further comprising receiving the verified prescription order and dispensing the medication from the verified prescription order, wherein the dispensing of the medication generates one or more alerts.

15. The method of claim 1, further comprising receiving the verified prescription order and dispensing the medication from the verified prescription order, wherein dispensing the medication comprises electronically updating a location's on-hand quantity of the dispensed medication.

16. The method of claim 15, wherein electronically updating a location's on-hand quantity of the dispensed medication generates alerts.

17. The method of claim 1, further comprising receiving the verified prescription order and administering the medication dispensed from the verified prescription order to the patient, wherein administering the medication comprises:
    identifying the medication to be administered; and
    identifying the receiving patient.

18. The method of claim 17, wherein the medication is identified by scanning a medication bar code.

19. The method of claim 17, wherein the medication is identified by selecting medication from a list.

20. The method of claim 17, wherein the patient is identified by scanning a patient bar code.

21. The method of claim 17, wherein the patient is identified by an electronic chip.

22. The method of claim 17, wherein administering the medication further comprises:
    performing checks to determine if this is the right patient, right medication, right dosage, right route and right time of administration; and
    wherein recording of the administration includes recording observations about the patient, wherein the observations include blood pressure, pain scale, or sugar level.

23. The method of claim 1, further comprising monitoring the patient, wherein monitoring the patient includes continuously analyzing information generated from one or more of the prescription order, verification of the prescription order, dispensing the medication or administering the medication.

24. The method of claim 23, wherein continuously analyzing information comprises continuously analyzing one or more of laboratory results, radiology results, unverified prescription order, verified prescription orders, scheduled tests, administered medication, adverse medication reactions, allergies, intravenous infusion rates, patient vital signs, patient observations, or cost of patient's treatment.

25. The method of claim 1, wherein monitoring the patient generates information that is communicated to prescribing.

26. The method of claim 25, wherein the information generated is in graph form, chart form, tabular data, or text.

27. The method of claim 1, wherein placing the prescription order in a queue by the computing apparatus using the scheduling technique includes prioritizing the prescription orders based on the medications' scheduled administration time.

28. The method of claim 27, wherein the scheduling technique includes prioritizing the prescription orders based on the location of the medication.

29. A medication use apparatus comprising:
    a processor configured to receive a prescription order for prescribing medication to a patient from a prescribing computing apparatus,
    the processor being further configured to place the prescription order in a queue including one or more other prescription orders using a scheduling technique, wherein the processor being configured to place the prescription order in a queue comprises the processor being configured to prioritize the queue based on one or more scheduled follow-up medication interventions,
    wherein the processor is configured to receive selection of a prescription order from the queue, receive input to indicate verification of an appropriateness of the selected prescription order, and generate a verified prescription order in response thereto,
    wherein the processor is configured to send the verified prescription order to one or more other apparatuses to facilitate dispensing the medication, providing a medication administration task to direct administering the medication to the patient, and monitoring status reports submitted, electronically by medical personnel, regarding the patient after administering the medication, wherein information related to the dispensing, administering and monitoring is recorded and made available for a subsequent verification of the appropriateness of a prescription order for a subsequent prescribing of medication to the patient, wherein the processor is configured to send the verified prescription order by sending the verified prescription order to a dispensing location selected based on an availability of a medication inventory of a medication identified by the verified prescription order at one or more dispensing locations associated with the one or more other apparatuses, and wherein the processor is further configured to receive and present information related to one or more of the dispensing, administering or monitoring for a previous prescribing of medication to the patient before receiving input to indicate verification to thereby facilitate the verification, wherein the processor being configured to receive and present information includes being configured to receive and present clinical information including real-time patient information, medication information that includes possible adverse medication interactions, or administering guidelines, the clinical information being presented to thereby facilitate a comparison of the prescription order and the clinical information, and wherein the processor is configured to receive in at least one instance an indication of an error based upon the comparison of the prescription order and the clinical information; and in response thereto, the processor is configured to receive input modifying the prescription order; and the processor is configured to send a message including the modified prescription order to the prescribing computing apparatus.

30. The medication use apparatus of claim 29 embodied as a personal digital assistant or computer system, the personal digital assistant or computer system including the processor.

31. The medication use apparatus of claim 29, wherein the processor being configured to receive a prescription order, send the verified prescription order and receive information related to the dispensing, administering and monitoring include being configured to communicate over an electronic medium, wherein the electronic medium is a network, World Wide Web, or Intranet.

32. The medication use apparatus of claim 31, wherein the processor is configured to communicate using a health level seven messaging protocol.

33. The medication use apparatus of claim 29, wherein the message is an alert.

34. The medication use apparatus of claim 29, wherein the processor is further configured to determine the dispensing location based on a plurality of dispensing requirements, the dispensing location being determined from one or more dispensing locations available for dispensing the medication.

35. The medication use apparatus of claim 34, wherein the dispensing requirement is patient location, type of medication, or quantity of medication needed.

36. The medication use apparatus of claim 34, wherein the one or more dispensing locations available for dispensing the medication include one or more of a robotic dispensing system, an automated storage and retrieval system, or medication dispensing cabinets.

37. A closed loop medication use system for patient care, comprising:

one or more centralized servers coupled to a plurality of databases, the databases stored on one or more storage devices;

a prescribing module coupled to the centralized servers, wherein the prescribing module is configured to generate a prescription order for prescribing medication to a patient;

a transcribing module coupled to the centralized servers, wherein the prescribing module is configured to place the prescription order in a queue including one or more other prescription orders using a scheduling technique, receive selection of a prescription order from the queue, receive input to indicate verification of an appropriateness of the selected prescription order, and generate a verified prescription order in response thereto, wherein the transcribing module is configured to prioritize the queue based on one or more scheduled follow-up medication interventions;

a dispensing module coupled to the centralized servers, wherein the dispensing module is configured to dispense or facilitate dispensing of one or more medications prescribed on the prescription order;

an administering module coupled to the centralized servers; and a monitoring module coupled to the centralized servers, wherein the monitoring module is configured to monitor information generated by the closed loop medication use system, wherein the transcribing module is configured to send the verified prescription order to the dispensing module, administering module and monitoring module to facilitate dispensing the medication, providing a medication administration task to direct administering the medication to the patient, and monitoring status reports submitted, electronically by medical personnel, regarding the patient after administering the medication, wherein the transcribing module is configured to send the verified prescription order to a dispensing location selected based on a determination as to a quantity of a medication identified by the verified prescription order in inventory at one or more dispensing locations associated with the dispensing module, the selected dispensing location comprising a selected type of dispenser from among a plurality of different types of dispensers, and wherein information related to the dispensing, administering and monitoring is recorded and made available for a subsequent verification of the appropriateness of a prescription order for a subsequent prescribing of medication to the patient wherein making the information available for the subsequent verification includes receiving and presenting clinical information including real-time patient information, medication information that includes possible adverse medication interactions, or administering guidelines, the clinical information being presented to thereby facilitate a comparison of the prescription order and the clinical information, and wherein receiving a prescription order includes receiving the prescription order from the prescribing module, and wherein the transcribing module is further configured for:

receiving in at least one instance an indication of an error based upon the comparison of the prescription order and the clinical information; and in response thereto, receiving input at the transcribing module modifying the prescription order; and sending a message including the modified prescription order to the prescribing module.

38. The closed loop medication use system of claim 37, wherein the prescribing module sends the prescription order to the centralized servers, wherein the prescription order prescribes the medication for a patient.

39. The closed loop medication use system of claim 38, wherein the centralized server sends the prescription order to the transcribing module to verify appropriateness.

40. The closed loop medication use system of claim 39, wherein the transcribing module sends the verified prescription order to the centralized server, wherein the centralized server informs the dispensing module of the medication to dispense.

41. The closed loop medication use system of claim 40, wherein an administering clinician receives the dispensed medication from the dispensing module, wherein the administering module receives information from the centralized server for administering the medication to a patient.

42. The closed loop medication use system of claim 41, wherein the administering clinician uses the information received by the administering module to check if this is the right patient, right medication, right dosage, right route and right time of administration.

43. The closed loop medication use system of claim 42, wherein after the administering clinician administers the medication, the administering module informs the application server of the medication administration, wherein the administration is recorded.

44. The closed loop medication use system of claim 43, wherein information on the medication administration is communicated from the server to the monitoring module.

45. The closed loop medication use system of claim 44, wherein the prescribing module, transcribing module, dispensing module, administering module and monitoring module communicate using a health level seven messaging protocol.

46. The closed loop medication use system of claim 37, wherein the storage device is an redundant array of inexpensive disks, hard disk drive, compact disc jukebox, or tape drive.

47. The closed loop medication use system of claim 37, wherein the database is a medication information database, radiology database, prescription order database, patient-care site financial database, laboratory database, clinical recommended healthcare industry practices database, standard of care database, patient information database, physician's database, or recommended prescribing healthcare industry practices database.

48. The closed loop medication use system of claim 47, wherein one or more database is coupled to the prescribing module through one or more database servers.

49. The closed loop medication use system of claim 47, wherein one or more database is coupled to the transcribing module through one or more database servers.

50. The closed loop medication use system of claim 47, wherein one or more database is coupled to the dispensing module through one or more database servers.

51. The closed loop medication use system of claim 47, wherein one or more database is coupled to the administering module through one or more database servers.

52. The closed loop medication use system of claim 47, wherein one or more database is coupled to the monitoring module through one or more database servers.

53. A system for use of medication, the system comprising:

means for generating a prescription order for prescribing medication to a patient;

means for transcribing the prescription order including placing in a queue including one or more other prescription orders using a scheduling technique, receiving selection of a prescription order from the queue, receiving input to indicate verification of an appropriateness of the selected prescription order, and generating a verified prescription order in response thereto, wherein placing in a queue comprises prioritizing the queue based on one or more scheduled follow-up medication interventions;

means for dispensing the medication from the verified prescription order, wherein dispensing the medication comprises sending the verified prescription order to a dispensing location associated with a selected one of one or more computer apparatuses based on an availability of a medication inventory of a medication identified by the verified prescription order at one or more dispensing locations associated with the one or more computer apparatuses;

means for providing a medication administration task to direct administering the medication to the patient, wherein the administration of the medication is recorded; and means for monitoring status reports submitted, electronically by medical personnel, regarding the patient, wherein verification of the prescription order in the means for transcribing comprises: means for comparing the prescription order to clinical information, wherein clinical information is real-time patient information, medication information that includes possible adverse medication interactions, or administering guidelines, wherein comparison of the prescription order in at least one instance produces an error, the system further comprising:

means for modifying the prescription order when comparison of the prescription order produces error; and means for sending a message including the modified prescription order to the means for prescribing.

54. The system of claim 53, wherein the means for prescribing, transcribing, dispensing, administering, and monitoring communicate information over a medium.

55. The method of claim 54, wherein information is communicated between the prescribing means, transcribing means, dispensing means, administering means and monitoring means using a health level seven messaging protocol.

56. The system of claim 53, wherein the means for prescribing comprises:

means for receiving information generated from monitoring the patient;

means for comparing the generated information to medication selection criteria; and means for determining at least one recommended medication based on the comparison.

57. The system of claim 56, wherein the medication selection criteria is from the group consisting of patient specific information, medication information, laboratory and radiology information, standard of care information, healthcare industry recommended treatment information, verified prescription orders, and alerts.

58. The system of claim 56, wherein the means for comparing comprises:

means for suggesting a plurality of recommended medications; and means for calculating an individual cost for each of the plurality of recommended medications.

59. The system of claim 53, wherein the message is an alert.

60. The system of claim 53, wherein the means for dispensing comprises: means for determining the optimal dispensing approach based on a plurality of dispensing requirements.

61. The system of claim 60, wherein the dispensing requirement is patient location, type of medication, or quantity of medication needed.

62. The system of claim 53, wherein means for administering the medication comprises:
means for selecting a patient;
means for identifying the medication to be administered; and
means for identifying the receiving patient.

63. The system of claim 62, wherein the medication is identified by scanning a medication bar code.

64. The system of claim 62, wherein the medication is identified by selecting the medication from a list.

65. The system of claim 62, wherein the patient is identified by scanning a patient bar code.

66. The system of claim 62, wherein the patient is identified by an electronic chip.

67. The system of claim 62, wherein means for administering the medication further comprises:
means for performing checks to determine if this is the right patient, right medication, right dosage, right route and right time of administration; and
wherein recording of the administration includes recording observations about the patient, wherein the observation is blood pressure, pain scale, or sugar level.

68. The system of claim 53, wherein means for monitoring the patient includes continuously analyzing information generated from the means for prescribing, transcribing, dispensing and administering.

69. The system of claim 68, wherein the information generated is laboratory results, radiology results, unverified prescription order, verified prescription orders, scheduled tests, administered medication, adverse medication reactions, allergies, intravenous infusion rates, patient vital signs, patient observations, or cost of patient's treatment.

70. The system of claim 53, wherein the means for monitoring the patient generates information that is communicated to the means for prescribing.

71. The method of claim 70, wherein the information generated is in graph form, chart form, tabular data, or text.

72. The method of claim 1, wherein sending the prescription based on an availability of a medication inventory of a medication identified by the prescription comprises receiving an input of the availability of the medication inventory of the various dispensing locations.

73. The method of claim 1, further comprising providing access to medication stored in one or more unit-based medication-dispensing cabinets in response to successful authentication of a user requesting access to the one or more unit-based medication-dispensing cabinets to at least retrieve a medication identified by the prescription.

* * * * *